(12) United States Patent
Anderson

(10) Patent No.: US 7,893,204 B2
(45) Date of Patent: Feb. 22, 2011

(54) ATTRACTIN/MAHOGANY-LIKE POLYPEPTIDES

(75) Inventor: Dirk M. Anderson, Port Townsend, WA (US)

(73) Assignee: Immunex Corporation, Thousand Oaks, CA (US)

( * ) Notice: Subject to any disclaimer, the term of this patent is extended or adjusted under 35 U.S.C. 154(b) by 0 days.

(21) Appl. No.: 12/148,929

(22) Filed: Apr. 22, 2008

(65) Prior Publication Data

US 2009/0022724 A1    Jan. 22, 2009

Related U.S. Application Data

(62) Division of application No. 10/154,670, filed on May 23, 2002, now Pat. No. 7,411,055.

(60) Provisional application No. 60/324,626, filed on Sep. 24, 2001, provisional application No. 60/293,608, filed on May 25, 2001.

(51) Int. Cl.
  *G01N 33/00* (2006.01)
  *C07K 14/00* (2006.01)
  *C07K 17/00* (2006.01)
(52) U.S. Cl. .......................... 530/350; 436/86; 436/87
(58) Field of Classification Search .................. None
  See application file for complete search history.

(56) References Cited

U.S. PATENT DOCUMENTS

| 6,933,132 B1 | 8/2005 | Duke-Cohan et al. | |
|---|---|---|---|
| 2004/0023219 A1* | 2/2004 | Sun et al. ...................... | 435/6 |

FOREIGN PATENT DOCUMENTS

| WO | WO 00/05373 | | 2/2000 |
|---|---|---|---|
| WO | WO 00/15651 | | 3/2000 |
| WO | WO 01/16156 A1 | | 3/2001 |
| WO | WO 03/064599 | * | 8/2003 |

OTHER PUBLICATIONS

Lazar article (Molecular and Cellular Biology 8(3): 1247-1252, Mar. 1988).*
Duke-Cohan JS, et al., "Attractin (DPPT-L), a member of the CUB family of cell adhesion and guidance proteins, is secreted by activated human T lymphocytes and modulates immune cell interactions," *Proc. Natl.Acad. Sci. USA*, 95:11336-11341, Sep. 1998.
GenCore database alignment between Applicants' SEQ ID No. 1 and nucleic acid sequence of Nagase et al., 3 sheets, 1998.
GenCore database alignment between Applicants' SEQ ID No. 1 and sequence 11 of U.S. Patent No. 6,933,132, 3 sheets, 1998.
Gen Core nucleic acid databases. Alignment between Applicant's SEQ ID No. 1 and sequence 13 of U.S. Patent No. 6,933,132 (effective filed Sep. 14, 1998), 3 pages.
GenCore nucleic acid databases. Alignment between Applicant's SEQ ID No. 1 and sequence 14 of U.S. Patent No. 6,274,339 (filed Feb. 5, 1999), 3 pages.
GenCore nucleic acid databases. Alignment between Applicant's SEQ ID No. 1 and sequence of WO 200015651 A1 (published Mar. 23, 2000), 3 pages.
GenCore database alignment between Applicants' SEQ ID No. 1 and SEQ ID No. 18, 3 sheets, 2002.
Gunn TM, et al., "The mouse *mahogany* locus encodes a transmembrane form of human attractin," *Nature* 398:152-156, Mar. 1999.
He L., et al., "A biochemical function for attractin in agouti-induced pigmentation and obesity," *Nature Genetics* 27:40-47, Jan. 2001.
Kuramoto T, et al., Attractin/Mahogany/Zitter plays a critical role in myelination of the central nervous system, *PNAS* 98(2):559-564, Jan. 16, 2001.
Lazar, et al., "Transforming Growth Factor alpha: Mutation of Aspartic Acid 47 and Leucine 48 Results in Difference Biological Activities," *Molecular and Cellular Biology* 8:3):1247-1252, Mar. 1988.
Malik R, et al., "Expression of Attractin and Its Differential Enzyme Activity in Glioma Cells," *Biochem. and Biophysical Research Communications* 284:289-294, 2001.
Nagase, et al., "Prediction of the Coding Sequences of Unidentified Human Genes. IX. The Complete Sequences of 100 New cDNA Clones from Brain Which Can Code for Large Proteins in vitro," *DNA Res* 5:31-39, 1998.
Nagle DL, et al., "The *mahogany* protein is a receptor involved in suppression of obesity," *Nature* 398:148-152, Mar. 11, 1999.
Tang W, et al., "Secreted and membrane attractin result from alternative splicing of the human ATRN gene," *PNAS* 97(11):6025-6030, May 23, 2000.
EBI Database EMBL Accession No. 060283, Aug. 1, 1998.
EBI Database EMBL Accession No. AB011106, Apr. 10, 1998.

* cited by examiner

*Primary Examiner*—Alana M Harris
(74) *Attorney, Agent, or Firm*—Christina M. Bellas

(57) ABSTRACT

The present disclosure provides attractin/mahogany-like polypeptides and fragments thereof, polynucleotides encoding such polypeptides and fragments, processes for production of recombinant forms of such polypeptides, antibodies generated against these polypeptides or fragments, and assays and methods employing these polypeptides, antibodies, and polynucleotides.

7 Claims, 14 Drawing Sheets

FIGURE 1(a)

Sequence of full-length human homolog of attractin/mahogany:

```
━━━━━━━▶
        ATGGAGACTGGGGGCCGGGCCCGCACTGGTACCCCGCAGCCAGCGGCCCCGGGGGTGTGG
        MetGluThrGlyGlyArgAlaArgThrGlyThrProGlnProAlaAlaProGlyValTrp

AGGGCTCGGCCGGCGGGCGGCGGCGGCGGGGGCGCCTCCTCCTGGCTGCTGGACGGGAAC
        ArgAlaArgProAlaGlyGlyGlyGlyGlyAlaSerSerTrpLeuLeuAspGlyAsn

AGCTGGCTGCTGTGCTATGGCTTCCTCTACCTGGCGCTCTACGCGCAGGTGTCCCAGTCC
        SerTrpLeuLeuCysTyrGlyPheLeuTyrLeuAlaLeuTyrAlaGlnValSerGlnSer

AAGCCGTGCGAGAGGACCGGCTCCTGCTTCTCGGGCCGCTGTGTCAACTCCACCTGCCTC
        LysProCysGluArgThrGlySerCysPheSerGlyArgCysValAsnSerThrCysLeu

TGCGACCCGGGCTGGGTGGGGGACCAGTGCCAGCACTGCCAGGGCAGGTTCAAGTTAACA
        CysAspProGlyTrpValGlyAspGlnCysGlnHisCysGlnGlyArgPheLysLeuThr
━━━━━━━▶
        GAACCTTCTGGATATTTAACAGATGGCCCAATTAACTATAAATATAAAACTAAATGTACT
        GluProSerGlyTyrLeuThrAspGlyProIleAsnTyrLysTyrLysThrLysCysThr

TGGCTCATTGAAGGCTATCCAAATGCAGTGTTAAGATTAAGATTCAATCATTTTGCTACA
        TrpLeuIleGluGlyTyrProAsnAlaValLeuArgLeuArgPheAsnHisPheAlaThr
                                       ◀━━━━━━━
        GAATGTAGCTGGGATCATATGTATGTTTATGATGGAGATTCAATATATGCACCTTTAATA
        GluCysSerTrpAspHisMetTyrValTyrAspGlyAspSerIleTyrAlaProLeuIle

GCTGTACTTAGTGGTTTGATAGTCCCTGAAATAAGGGGCAATGAAACTGTGCCTGAAGTT
        AlaValLeuSerGlyLeuIleValProGluIleArgGlyAsnGluThrValProGluVal

GTTACTACATCTGGCTATGCACTGTTACATTTTTTTAGTGATGCTGCGTATAATCTAACT
        ValThrThrSerGlyTyrAlaLeuLeuHisPhePheSerAspAlaAlaTyrAsnLeuThr

GGTTTCAACATTTTCTATTCAATCAATTCTTGTCCTAACAATTGCTCTGGTCATGGGAAG
        GlyPheAsnIlePheTyrSerIleAsnSerCysProAsnAsnCysSerGlyHisGlyLys

TGTACAACTAGTGTCTCTGTTCCAAGTCAAGTATATTGTGAATGTGATAAATACTGGAAG
        CysThrThrSerValSerValProSerGlnValTyrCysGluCysAspLysTyrTrpLys

GGTGAAGCTTGTGATATTCCTTACTGTAAAGCCAATTGCGGCAGTCCAGATCACGGTTAC
        GlyGluAlaCysAspIleProTyrCysLysAlaAsnCysGlySerProAspHisGlyTyr

TGTGACCTGACTGGAGAAAAATTATGTGTCTGCAATGATAGTTGGCAAGGTCCTGATTGT
        CysAspLeuThrGlyGluLysLeuCysValCysAsnAspSerTrpGlnGlyProAspCys

TCTTTGAATGTTCCCTCTACTGAGTCTTACTGGATTCTGCCAAACGTTAAACCCTTCAGT
        SerLeuAsnValProSerThrGluSerTyrTrpIleLeuProAsnValLysProPheSer

CCTTCTGTAGGTCGGGCTTCACATAAAGCAGTTTTACACGGGAAATTTATGTGGGTGATT
        ProSerValGlyArgAlaSerHisLysAlaValLeuHisGlyLysPheMetTrpValIle

GGTGGATATACTTTTAACTACAGTTCTTTTCAAATGGTCCTAAATTACAATTTAGAAAGC
        GlyGlyTyrThrPheAsnTyrSerSerPheGlnMetValLeuAsnTyrAsnLeuGluSer

AGTATATGGAATGTAGGAACTCCATCAAGGGGACCTCTCCAGAGATATGGACACTCTCTT
        SerIleTrpAsnValGlyThrProSerArgGlyProLeuGlnArgTyrGlyHisSerLeu

GCTTTATATCAGGAAAACATCTTTATGTATGGAGGCAGAATTGAAACAAATGATGGCAAT
        AlaLeuTyrGlnGluAsnIlePheMetTyrGlyGlyArgIleGluThrAsnAspGlyAsn

GTCACAGATGAATTATGGGTTTTTAACATACATAGTCAGTCATGGAGTACAAAAACTCCT
        ValThrAspGluLeuTrpValPheAsnIleHisSerGlnSerTrpSerThrLysThrPro
```

FIGURE 1(b)

```
ACTGTTCTTGGACATGGTCAGCAGTATGCTGTGGAGGGACATTCAGCACATATTATGGAG
ThrValLeuGlyHisGlyGlnGlnTyrAlaValGluGlyHisSerAlaHisIleMetGlu

TTGGATAGTAGAGATGTTGTCATGATCATAATATTTGGATATTCTGCAATATATGGTTAT
LeuAspSerArgAspValValMetIleIleIlePheGlyTyrSerAlaIleTyrGlyTyr

ACAAGCAGCATACAGGAATACCATATCTCATCAAACACTTGGCTTGTTCCAGAAACTAAA
ThrSerSerIleGlnGluTyrHisIleSerSerAsnThrTrpLeuValProGluThrLys

GGAGCTATTGTACAAGGTGGATATGGCCATACTAGTGTGTATGATGAAATAACAAAGTCC
GlyAlaIleValGlnGlyGlyTyrGlyHisThrSerValTyrAspGluIleThrLysSer

ATTTATGTTCATGGAGGGTATAAAGCATTGCCAGGGAACAAATATGGATTGGTTGATGAT
IleTyrValHisGlyGlyTyrLysAlaLeuProGlyAsnLysTyrGlyLeuValAspAsp

CTTTATAAATATGAAGTTAACACTAAGACTTGGACTATTTTGAAAGAAAGTGGGTTTGCC
LeuTyrLysTyrGluValAsnThrLysThrTrpThrIleLeuLysGluSerGlyPheAla

AGATACCTTCATTCAGCTGTTCTTATCAATGGAGCTATGCTTATTTTTGGAGGAAATACC
ArgTyrLeuHisSerAlaValLeuIleAsnGlyAlaMetLeuIlePheGlyGlyAsnThr

CATAATGACACTTCCTTGAGTAACGGTGCAAAATGTTTTTCTGCCGATTTCCTGGCATAT
HisAsnAspThrSerLeuSerAsnGlyAlaLysCysPheSerAlaAspPheLeuAlaTyr

GACATAGCTTGTGATGAATGGAAAATACTACCAAAACCAAATCTTCATAGAGATGTCAAC
AspIleAlaCysAspGluTrpLysIleLeuProLysProAsnLeuHisArgAspValAsn

AGATTTGGACACTCTGCAGTAGTCATTAACGGGTCCATGTATATATTTGGGGGATTTTCT
ArgPheGlyHisSerAlaValValIleAsnGlySerMetTyrIlePheGlyGlyPheSer

AGTGTACTCCTTAATGATATCCTTGTATACAAGCCTCCAAATTGCAAGGCTTTCAGAGAT
SerValLeuLeuAsnAspIleLeuValTyrLysProProAsnCysLysAlaPheArgAsp

GAAGAACTTTGTAAAAATGCTGGTCCAGGGATAAAATGTGTTTGGAATAAAAATCACTGT
GluGluLeuCysLysAsnAlaGlyProGlyIleLysCysValTrpAsnLysAsnHisCys

GAATCTTGGGAATCTGGGAATACTAATAATATTCTTAGAGCAAAGTGCCCTCCTAAAACA
GluSerTrpGluSerGlyAsnThrAsnAsnIleLeuArgAlaLysCysProProLysThr

GCTGCTTCTGATGACAGATGTTACAGATATGCAGATTGTGCCAGCTGTACTGCCAATACA
AlaAlaSerAspAspArgCysTyrArgTyrAlaAspCysAlaSerCysThrAlaAsnThr

AATGGGTGCCAATGGTGTGATGACAAGAAATGCATTTCGGCAAATAGTAACTGCAGTATG
AsnGlyCysGlnTrpCysAspAspLysLysCysIleSerAlaAsnSerAsnCysSerMet

TCTGTCAAGAACTACACCAAATGTCATGTGAGAAATGAGCAGATTTGTAACAAACTTACC
SerValLysAsnTyrThrLysCysHisValArgAsnGluGlnIleCysAsnLysLeuThr

AGCTGTAAAAGCTGTTCACTAAACTTGAATTGCCAGTGGGATCAGAGACAGCAAGAATGC
SerCysLysSerCysSerLeuAsnLeuAsnCysGlnTrpAspGlnArgGlnGlnGluCys

CAGGCTTTACCAGCTCATCTTTGTGGAGAAGGATGGAGTCATATTGGGGATGCTTGTCTT
GlnAlaLeuProAlaHisLeuCysGlyGluGlyTrpSerHisIleGlyAspAlaCysLeu

AGAGTCAATTCCAGTAGAGAAAACTATGACAATGCAAAACTTTATTGCTATAATCTTAGT
ArgValAsnSerSerArgGluAsnTyrAspAsnAlaLysLeuTyrCysTyrAsnLeuSer

GGAAATCTTGCTTCATTAACAACCTCAAAAGAAGTAGAATTTGTTCTGGATGAAATACAG
GlyAsnLeuAlaSerLeuThrThrSerLysGluValGluPheValLeuAspGluIleGln

AAGTATACACAACAGAAAGTATCACCTTGGGTAGGCTTGCGCAAGATCAATATATCCTAT
```

FIGURE 1(c)

LysTyrThrGlnGlnLysValSerProTrpValGlyLeuArgLysIleAsnIleSerTyr

TGGGGATGGGAAGACATGTCTCCTTTTACAAACACAACACTACAGTGGCTTCCTGGCGAA
TrpGlyTrpGluAspMetSerProPheThrAsnThrThrLeuGlnTrpLeuProGlyGlu

CCCAATGATTCTGGGTTTTGTGCATATCTGGAAAGGGCTGCAGTGGCAGGCTTAAAAGCT
ProAsnAspSerGlyPheCysAlaTyrLeuGluArgAlaAlaValAlaGlyLeuLysAla

AATCCTTGTACATCTATGGCAAATGGCCTTGTCTGTGAAAAACCTGTTGTTAGTCCAAAT
AsnProCysThrSerMetAlaAsnGlyLeuValCysGluLysProValValSerProAsn

CAAAATGCGAGGCCGTGCAAAAAGCCATGCTCTCTGAGGACATCATGTTCCAACTGTACA
GlnAsnAlaArgProCysLysLysProCysSerLeuArgThrSerCysSerAsnCysThr

AGCAATGGCATGGAGTGTATGTGGTGCAGCAGTACGAAACGATGTGTTGACTCTAATGCC
SerAsnGlyMetGluCysMetTrpCysSerSerThrLysArgCysValAspSerAsnAla

TATATCATCTCTTTTCCATATGGACAATGTCTAGAGTGGCAAACTGCCACCTGCTCCCCT
TyrIleIleSerPheProTyrGlyGlnCysLeuGluTrpGlnThrAlaThrCysSerPro

CAAAATTGTTCTGGATTGAGAACCTGTGGACAGTGTTTGGAACAGCCTGGATGTGGCTGG
GlnAsnCysSerGlyLeuArgThrCysGlyGlnCysLeuGluGlnProGlyCysGlyTrp

TGCAATGATCCTAGTAATACAGGAAGAGGACATTGCATTGAAGGTTCTTCACGGGGACCA
CysAsnAspProSerAsnThrGlyArgGlyHisCysIleGluGlySerSerArgGlyPro

ATGAAGCTTATTGGAATGCACCACAATGAGATGGTTCTTGACACCAATCTTTGCCCCAAA
MetLysLeuIleGlyMetHisHisAsnGluMetValLeuAspThrAsnLeuCysProLys

GAAAAGAACTATGAGTGGTCCTTTATCCAGTGTCCAGCTTGCCAGTGTAATGGACATAGC
GluLysAsnTyrGluTrpSerPheIleGlnCysProAlaCysGlnCysAsnGlyHisSer

ACTTGCATCAATAATAATGTGTGCGAACAGTGTAAAAATCTCACCACAGGAAAGCAGTGT
ThrCysIleAsnAsnAsnValCysGluGlnCysLysAsnLeuThrThrGlyLysGlnCys

CAAGATTGTATGCCAGGTTATTATGGAGATCCAACCAATGGTGGACAGTGCACAGCTTGT
GlnAspCysMetProGlyTyrTyrGlyAspProThrAsnGlyGlyGlnCysThrAlaCys

ACATGCAGTGGCCATGCAAATATCTGTCATCTGCACACAGGAAAATGTTTCTGCACAACT
ThrCysSerGlyHisAlaAsnIleCysHisLeuHisThrGlyLysCysPheCysThrThr

AAAGGAATAAAAGGTGACCAATGCCAATTATGTGACTCTGAAAATCGCTATGTTGGTAAT
LysGlyIleLysGlyAspGlnCysGlnLeuCysAspSerGluAsnArgTyrValGlyAsn

CCACTTAGAGGAACATGTTATTACAGCCTTTTGATTGATTATCAATTTACCTTCAGCTTA
ProLeuArgGlyThrCysTyrTyrSerLeuLeuIleAspTyrGlnPheThrPheSerLeu

TTACAGGAAGATGATCGCCACCATACTGCCATAAACTTTATAGCAAACCCAGAACAGTCG
LeuGlnGluAspAspArgHisHisThrAlaIleAsnPheIleAlaAsnProGluGlnSer

AACAAAAATCTGGATATATCAATTAATGCATCAAACAACTTTAATCTCAACATTACGTGG
AsnLysAsnLeuAspIleSerIleAsnAlaSerAsnAsnPheAsnLeuAsnIleThrTrp

TCTGTCGGTTCAACAGCTGGAACAATATCTGGGGAAGAGACTTCTATAGTTTCCAAGAAT
SerValGlySerThrAlaGlyThrIleSerGlyGluGluThrSerIleValSerLysAsn

AATATAAAGGAATACAGAGATAGTTTTTCCTATGAAAAATTTAACTTTAGAAGCAATCCT
AsnIleLysGluTyrArgAspSerPheSerTyrGluLysPheAsnPheArgSerAsnPro

AACATTACGTTCTATGTGTACGTCAGCAACTTTTCCTGGCCTATTAAAATACAGATTGCA
AsnIleThrPheTyrValTyrValSerAsnPheSerTrpProIleLysIleGlnIleAla

FIGURE 1(d)

```
TTCTCACAACACAATACAATCATGGACCTTGTGCAGTTTTTTGTCACCTTCTTCAGTTGT
PheSerGlnHisAsnThrIleMetAspLeuValGlnPhePheValThrPhePheSerCys

TTCCTATCCTTATTGCTGGTGGCTGCTGTGGTATGGAAGATCAAACAAACTTGTTGGGCT
PheLeuSerLeuLeuLeuValAlaAlaValValTrpLysIleLysGlnThrCysTrpAla

TCTCGACGGAGAGAGCAACTGCTTCGAGAACGACAGCAGATGGCCAGCCGTCCCTTTGCT
SerArgArgArgGluGlnLeuLeuArgGluArgGlnGlnMetAlaSerArgProPheAla

TCTGTTGATGTAGCTCTGGAAGTGGGAGCTGAACAAACAGAGTTTCTGCGAGGGCCATTA
SerValAspValAlaLeuGluValGlyAlaGluGlnThrGluPheLeuArgGlyProLeu

GAGGGGGCACCCAAGCCAATTGCCATTGAACCATGTGCTGGGAACAGAGCTGCTGTTCTG
GluGlyAlaProLysProIleAlaIleGluProCysAlaGlyAsnArgAlaAlaValLeu

ACTGTGTTTCTTTGTCTACCACGAGGATCATCAGGTGCCCCTCCCCCTGGGCAGTCAGGC
ThrValPheLeuCysLeuProArgGlySerSerGlyAlaProProProGlyGlnSerGly

CTTGCAATTGCCAGTGCCCTAATAGATATTTCACAACAGAAAGCTTCAGATAGTAAAGAT
LeuAlaIleAlaSerAlaLeuIleAspIleSerGlnGlnLysAlaSerAspSerLysAsp

AAGACTTCTGGAGTCCGGAATCGAAAACACCTTTCAACACGTCAAGGAACTTGTGTCTGA
LysThrSerGlyValArgAsnArgLysHisLeuSerThrArgGlnGlyThrCysVal
```

FIGURE 2(a)

```
              1                                                             50
   Attractin  ~~~~~~~~~~ ~~~~~~~~~~ ~~~~~~~~~~ ~~~~~~~~~~ ~~~~~~~~~~
    Mahogany  mvavaaaaat earlrgsttt taapagrkgr qhrpctatga wrpgprarlc
  HAMprotein  ~~~~~~~~~~ ~~~~~~~~~~ ~~~~~~~~~~ ~~~~~~~~~~ METGGRARTG
   Consensus  ~~~~~~~~~~ ~~~~~~~~~~ ~~~~~~~~~~ ~~~~~~~~~~ ~~~~~~~~~~

51                                                           100
   Attractin  ~~~~~~~~~~ ~~~~~~~~~~ ~~~~~~~~~~ ~mvaaaaate arlrrrtaat
    Mahogany  lprvls.... ralppppllp llfsllllpl preaeaaava aavsgsaaae
  HAMprotein  TPQPAAPGVW RARPAGGGGG GASSWLLDGN SWLLCYGFLY LALYAQ.VSQ
   Consensus  ~~~~~~~~~~ ~~~~~~~~~~ ~~~~~~~~~~ ---------- ----------

101                                                          150
   Attractin  aalagrsggp hCvnggrCnp gtgqCvCpag wvgeqCqhCg grfrltgssg
    Mahogany  akecdr...p .CvnggrCnp gtgqCvCptg wvgeqCqhCg grfrltgssg
  HAMprotein  SKPCERTGS. .CFS.GRCVN ST..CLCDPG WVGDQCQHCQ GRFKLTEPSG
   Consensus  -----R---- -C---GRC-- -T--C-C--G WVG-QCQHC- GRF-LT--SG 151                                                          200
   Attractin  fvtdgpgnyk yktkCtwlie gqpnrimrlr fnhfateCsw dhlyvydgds
    Mahogany  fvtdgpgnyk yktkCtwlie gqpnrimrlr fnhfateCsw dhlyvydgds
  HAMprotein  YLTDGPINYK YKTKCTWLIE GYPNAVLRLR FNHFATECSW DHMYVYDGDS
   Consensus  --TDGP-NYK YKTKCTWLIE G-PN---RLR FNHFATECSW DH-YVYDGDS 201                                                          250
   Attractin  iyaplvaafs glivperdgn etvpevvats gyallhffsd aaynltgfni
    Mahogany  iyapliaafs glivperdgn etapevtvts gyallhffsd aaynltgfni
  HAMprotein  IYAPLIAVLS GLIVPEIRGN ETVPEVVTTS GYALLHFFSD AAYNLTGFNI
   Consensus  IYAPL-A--S GLIVPE--GN ET-PEV--TS GYALLHFFSD AAYNLTGFNI 251                                                          300
   Attractin  tysfdmCpnn CsgrgeCkis ns.sdtveCe CsenwkgeaC diphCtdnCg
    Mahogany  tynfdmCpnn CsgrgeCkss ns.ssaveCe CsenwkgesC diphCtdnCg
  HAMprotein  FYSINSCPNN CSGHGKCTTS VSVPSQVYCE CDKYWKGEAC DIPYCKANCG
   Consensus  -Y----CPNN CSG-G-C--S -S----V-CE C---WKGE-C DIP-C--NCG 301                                                          350
   Attractin  fphrgiCnss dvrgCsCfsd wqgpgCsvpv panqsfwtre eysnl..klp
    Mahogany  fphrgiCnas dtrgCsCfph wqgpgCsipv panqsfwtre eysdl..klp
  HAMprotein  SPDHGYCDLT GEKLCVCNDS WQGPDCSLNV PSTESYWILP NVKPFSPSVG
   Consensus  -P--G-C--- ----C-C--- WQGP-CS--V P---S-W--- ----------

351                                                          400
   Attractin  rashkavvng nimwvvggym fnhsdynmvl aydlasrewl plnrsvnnvv
    Mahogany  rashkavvng nimwvvggym fnhsdysmvl aydltsrewl plnhsvnsvv
  HAMprotein  RASHKAVLHG KFMWVIGGYT FNYSSFQMVL NYNLESSIW. NVGTPSRGPL
   Consensus  RASHKAV--G --MWV-GGY- FN-S---MVL -Y-L-S--W- ----------

401                                                          450
   Attractin  vryghslaly kdkiymyggk idst.gnvtn elrvfhihne swvlltpka.
    Mahogany  vryghslalh kdkiymyggk idst.gnvtn elrvfhihne swvlltpka.
  HAMprotein  QRYGHSLALY QENIFMYGGR IETNDGNVTD ELWVFNIHSQ SWSTKTPTVL
   Consensus  -RYGHSLAL- ---I-MYGG- I----GNVT- EL-VF-IH-- SW---TP---

451                                                          500
   Attractin  ..keqyavvg hsahivtlkn grvvmlvifg hcplygyisn vqeydldknt
    Mahogany  ..kdqyavvg hsahivtlas grvvmlvifg hcplygyisv vqeydleknt
  HAMprotein  GHGQQYAVEG HSAHIMELDS RDVVMIIIFG YSAIYGYTSS IQEYHISSNT
   Consensus  ----QYAV-G HSAHI--L-- --VVM--IFG ----YGY-S- -QEY----NT
```

FIGURE 2(b)

```
            501                                                                          550
Attractin   wsilhtqgal  vqggyghssv  ydhrtralyv  hggykafsan  kyrladdlyr
Mahogany    wsilhtqgal  vqggyghssv  yddrtkalyv  hggykafsan  kyrladdlyr
HAMprotein  WLVPETKGAI  VQGGYGHTSV  YDEITKSIYV  HGGYKALPGN  KYGLVDDLYK
Consensus   W----T-GA-  VQGGYGH-SV  YD--T---YV  HGGYKA---N  KY-L-DDLY- 551                                                                          600
Attractin   ydvdtqmwti  lkdsrffryl  htavivsgtm  lvfggnthnd  tsmshgakCf
Mahogany    ydvdtqmwti  lkdsrffryl  htavivsgtm  lvfggnthnd  tsmshgakCf
HAMprotein  YEVNTKTWTI  LKESGFARYL  HSAVLINGAM  LIFGGNTHND  TSLSNGAKCF
Consensus   Y-V-T--WTI  LK-S-F-RYL  H-AV---G-M  L-FGGNTHND  TS-S-GAKCF 601                                                                          650
Attractin   ssdfmaydia  Cdrwsvlprp  dstmmstdla  ipavlhnstm  yvfggfnsll
Mahogany    ssdfmaydia  Cdrwsvlprp  elhhdvnrfg  hsavlynstm  yvfggfnsll
HAMprotein  SADFLAYDIA  CDEWKILPKP  NLHRDVNRFG  HSAVVINGSM  YIFGGFSSVL
Consensus   S-DF-AYDIA  CD-W--LP-P  ----------  --AV--N--M  Y-FGGF-S-L 651                                                                          700
Attractin   lsdilvftse  qCdahrseaa  Claagpgirc  vwntgssqCi  swalatdeqe
Mahogany    lsdvlvftse  qCdahrseaa  Cvaagpgirc  lwdtqssrCt  swelateeqa
HAMprotein  LNDILVYKPP  NCKAFRDEEL  CKNAGPGIKC  VWN..KNHCE  SWESGNTNNI
Consensus   L-D-LV----  -C-A-R-E--  C--AGPGI-C  -W------C-  SW--------

701                                                                          750
Attractin   eklkseCfsk  rtldhdrCdq  htdCysCtan  tndChwCnd.  hCvprnhsCs
Mahogany    eklkseCfsk  rtldhdrCdq  htdCysCtan  tndChwCnd.  hCvpvnhsCt
HAMprotein  ..LRAKCPPK  TAASDDRCYR  YADCASCTAN  TNGCQWCDDK  KCISANSNCS
Consensus   --L---C--K  -----DRC--  --DC-SCTAN  TN-C-WC-D-  -C---N--C-

751                                                                          800
Attractin   egqisifrye  nCpkdnpmyy  CnkktsCrsC  aldqnCqwep  rnqeCialpe
Mahogany    egqisiakye  sCpkdnpmyy  CnkktsCrsC  aldqnCqwep  rnqeCialpe
HAMprotein  ...MSVKNYT  KCHVRNEQ.I  CNKLTSCKSC  SLNLNCQWDQ  RQQECQALPA
Consensus   ----S---Y-  -C---N----  CNK-TSC-SC  -L--NCQW--  R-QEC-ALP- 801                                                                          850
Attractin   niCgigwhlv  gnsClkitta  kenydnaklf  Crnhnallas  lttqkkvefv
Mahogany    niCgngwhlv  gnsClkitta  kenydnakls  Crnhnaflas  ltsqkkvefv
HAMprotein  HLCGEGWSHI  GDACLRVNSS  RENYDNAKLY  CYNLSGNLAS  LTTSKEVEFV
Consensus   --CG-GW---  G--CL-----  -ENYDNAKL-  C-N----LAS  LT--K-VEFV 851                                                                          900
Attractin   lkqlrimqss  qsmskltltp  wvglrkinvs  ywcwedmspf  tnsllqwmps
Mahogany    lkqlrlmqss  qsmskltltp  wvglrkinvs  ywcwedmspf  tnsllqwmps
HAMprotein  LDEI......  QKYTQQKVSP  WVGLRKINIS  YWGWEDMSPF  TNTTLQWLPG
Consensus   L---------  Q-------P  WVGLRKIN-S  YW-WEDMSPF  TN--LQW-P-

901                                                                          950
Attractin   epsdagfCgi  lsepstrglk  aatCinplng  svCerpa...  nhsakqCrtp
Mahogany    epsdagfCgi  lsepstrglk  aatCinplng  svCerpa...  nhsakqCrtp
HAMprotein  EPNDSGFCAY  LERAAVAGLK  ANPCTSMANG  LVCEKPVVSP  NQNARPCKKP
Consensus   EP-D-GFC--  L------GLK  A--C----NG  -VCE-P----  N--A--C--P 951                                                                          1000
Attractin   CalrtaCgdC  tsgsseCmwC  snmkqCvdsn  ayvasfpfgq  CmewytmstC
Mahogany    CalrtaCgeC  tsssseCmwC  snmkqCvdsn  ayvasfpfgq  CmewytmssC
HAMprotein  CSLRTSCSNC  TSNGMECMWC  SSTKRCVDSN  AYIISFPYGQ  CLEWQT.ATC
Consensus   C-LRT-C--C  TS---ECMWC  S--K-CVDSN  AY--SFP-GQ  C-EW-T---C
```

FIGURE 2(c)

```
               1001                                                    1050
    Attractin  ppenCsgyct  CshCleqpgC  gwCtdpsntg  kgkCiegsyk  gpvkmpsqap
    Mahogany   ppenCsgyct  CshCleqpgC  gwCtdpsntg  kgkCiegsyk  gpvkmpsqas
   HAMprotein  SPQNCSGLRT  CGQCLEQPGC  GWCNDPSNTG  RGHCIEGSSR  GPMKL.....
    Consensus  -P-NCSG--T  C--CLEQPGC  GWC-DPSNTG  -G-CIEGS--  GP-K------

1051                                                    1100
    Attractin  tgnfypqpll  nssmCledsr  ynwsfihCpa  CqCnghskCi  nqsiCekCen
    Mahogany   agnvypqpll  nssmCledsr  ynwsfihCpa  CqCnghskCi  nqsiCekCed
   HAMprotein  IGMHHNEMVL  DTNLCPKEKN  YEWSFIQCPA  CQCNGHSTCI  NNNVCEQCKN
    Consensus  -G-------L  ----C-----  Y-WSFI-CPA  CQCNGHS-CI  N---CE-C--

1101                                                    1150
    Attractin  lttgkhCetC  isgfygdptn  ggkCqpCkCn  ghaslCntnt  gkCfCttkgv
    Mahogany   lttgkhCetC  isgfygdptn  ggkCqpCkCn  ghaslCntnt  gkCfCttkgv
   HAMprotein  LTTGKQCQDC  MPGYYGDPTN  GGQCTACTCS  GHANICHLHT  GKCFCTTKGI
    Consensus  LTTGK-C--C  --G-YGDPTN  GG-C--C-C-  GHA--C---T  GKCFCTTKG- 1151                                                    1200
    Attractin  kgdeCqlCev  enryqgnplr  gtCyytllid  yqftfslsqe  ddryytainf
    Mahogany   kgdeCqlCev  enryqgnplk  gtCyytllid  yqftfslsqe  ddryytainf
   HAMprotein  KGDQCQLCDS  ENRYVGNPLR  GTCYYSLLID  YQFTFSLLQE  DDRHHTAINF
    Consensus  KGD-CQLC--  ENRY-GNPL-  GTCYY-LLID  YQFTFSL-QE  DDR--TAINF 1201                                                    1250
    Attractin  vatpdeqnrd  ldmfinaskn  fnlnitwaas  fsagtqagee  mpvvsktnik
    Mahogany   vatpdeqnrd  ldmfinaskn  fnlnitwats  fpagtqtgee  vpvvsktnik
   HAMprotein  IANPEQSNKN  LDISINASNN  FNLNITWSVG  STAGTISGEE  TSIVSKNNIK
    Consensus  -A-P---N--  LD--INAS-N  FNLNITW---  --AGT--GEE  ---VSK-NIK 1251                                                    1300
    Attractin  eykdsfsnek  fdfrnhpnit  ffvyvsnftw  pikiqvqteq  ~~~~~~~~~~
    Mahogany   eykdsfsnek  fdfrnhpnit  ffvyvsnftw  pikiqiafsq  hsnfmdlvqf
   HAMprotein  EYRDSFSYEK  FNFRSNPNIT  FYVYVSNFSW  PIKIQIAFSQ  HNTIMDLVQF
    Consensus  EY-DSFS-EK  F-FR--PNIT  F-VYVSNF-W  PIKIQ----Q  ~~~~~~~~~~

1301                                                    1350
    Attractin  ~~~~~~~~~~  ~~~~~~~~~~  ~~~~~~~~~~  ~~~~~~~~~~  ~~~~~~~~~~
    Mahogany   fvtffscfls  lllvaavvwk  ikqscwasrr  reqllremqq  masrpfasvn
   HAMprotein  FVTFFSCFLS  LLLVAAVVWK  IKQTCWASRR  REQLLRERQQ  MASRPFASVD
    Consensus  ~~~~~~~~~~  ~~~~~~~~~~  ~~~~~~~~~~  ~~~~~~~~~~  ~~~~~~~~~~

1351                                                    1400
    Attractin  ~~~~~~~~~~  ~~~~~~~~~~  ~~~~~~~~~~  ~~~~~~~~~~  ~~~~~~~~~~
    Mahogany   valetdeepp  dliggsiktv  pkpialepcf  gnkaavlsvf  vrlprglggi
   HAMprotein  VALEVGAEQT  EFLRGPLEGA  PKPIAIEPCA  GNRAAVLTVF  LCLPRGSSGA
    Consensus  ~~~~~~~~~~  ~~~~~~~~~~  ~~~~~~~~~~  ~~~~~~~~~~  ~~~~~~~~~~

1401                                                    1450
    Attractin  ~~~~~~~~~~  ~~~~~~~~~~  ~~~~~~~~~~  ~~~~~~~~~~  ~~~~~~~~~~
    Mahogany   pppgqsrsrc  gqcpgghfsa  dansvqgevr  sckkpeaaaa  ctawnlhlil
   HAMprotein  PPPGQSGLAI  ASALIDISQQ  KASDSKDKTS  GVRNRKHLST  RQGTCV~~~~
    Consensus  ~~~~~~~~~~  ~~~~~~~~~~  ~~~~~~~~~~  ~~~~~~~~~~  ~~~~~~~~~~

1451             1491
    Attractin  ~~~~~~~~~~  ~~~~~~~~~~  ~~~~~~~~~~  ~~~~~~~~~~  ~
    Mahogany   gqefaltegv  wstklstgea  agrkqawgrr  lgtleasnsc  a
   HAMprotein  ~~~~~~~~~~  ~~~~~~~~~~  ~~~~~~~~~~  ~~~~~~~~~~  ~
    Consensus  ~~~~~~~~~~  ~~~~~~~~~~  ~~~~~~~~~~  ~~~~~~~~~~  ~
```

FIGURE 3(a)

Underlined = signal domain
Bold = EGF-like domains
Italics = CUB domain
Dotted Underlined = KELCH motif
Inverse text = C-type lectin (CTL) or carbohydrate-recognition domain
Wavy Underline = putative ligand binding motif of the common gamma cytokine chain
Bar = Laminin EGF-like Domain
Double Underlined = Transmembrane Domain

```
   1    METGGRARTG TPQPAAPGVW RARPAGGGGG GASSWLLDGN SWLLCYGFLY LALYAQVSQS

61    KPCERTGSCF SGRCVNSTCL CDPGWVGDQC QHCQGRFKLT EPSGYLTDGP INYKYKTKCT

121    WLIEGYPNAV LRLRFNHFAT ECSWDHMYVY DGDSIYAPLI AVLSGLIVPE IRGNETVPEV

181    VTTSGYALLH FFSDAAYNLT GFNIFYSINS CPNNCSGHGK CTTSVSVPSQ VYCECDKYWK

241    GEACDIPYCK ANCGSPDHGY CDLTGEKLCV CNDSWQGPDC SLNVPSTESY WILPNVKPFS

301    PSVGRASHKA VLHGKFMWVI GGYTFNYSSF QMVLNYNLES SIWNVGTPSR GPLQRYGHSL

361    ALYQENIFMY GGRIETNDGN VTDELWVFNI HSQSWSTKTP TVLGHGQQYA VEGHSAHIME

421    LDSRDVVMII IFGYSAIYGY TSSIQEYHIS SNTWLVPETK GAIVQGGYGH TSVYDEITKS

481    IYVHGGYKAL PGNKYGLVDD LYKYEVNTKT WTILKESGFA RYLHSAVLIN GAMLIFGGNT

541    HNDTSLSNGA KCFSADFLAY DIACDEWKIL PKPNLHRDVN RFGHSAVVIN GSMYIFGGFS

601    SVLLNDILVY KPPNCKAFRD EELCKNAGPG IKCVWNKNHC ESWESGNTNN ILRAKCPPKT

661    AASDDRCYRY ADCASCTANT NGCQWCDDKK CISANSNCSM SVKNYTKCHV RNEQICNKLT

721    SCKSCSLNLN CQWDQRQQEC QALPAHLCGE GWSHIGDACL RVNSSRENYD NAKLYCYNLS

781    GNLASLTTSK EVEFVLDEIQ KYTQQKVSPW VGLRKINISY WGWEDMSPFT NTTLQWLPGE

841    PNDSGFCAYL ERAAVAGLKA NPCTSMANGL VCEKPVVSPN QNARPCKKPC SLRTSCSNCT

901    SNGMECMWCS STKRCVDSNA YIISFPYGQC LEWQTATCSP QNCSGLRTCG QCLEQPGCGW

961    CNDPSNTGRG HCIEGSSRGP MKLIGMHHNE MVLDTNLCPK EKNYEWSFIQ CPACQCNGHS

1021    TCINNNVCEQ CKNLTTGKQC QDCMPGYYGD PTNGGQCTAC TCSGHANICH LHTGKCFCTT

1081    KGIKGDQCQL CDSENRYVGN PLRGTCYYSL LIDYQFTFSL LQEDDRHHTA INFIANPEQS
```

FIGURE 3(b)

```
1141    NKNLDISINA SNNFNLNITW SVGSTAGTIS GEETSIVSKN NIKEYRDSFS YEKFNFRSNP

1201    NITFYVYVSN FSWPIKIQIA FSQHNTIMDL VQFFVTFFSC FLSLLLVAAV VWKIKQTCWA

1261    SRRREQLLRE RQQMASRPFA SVDVALEVGA EQTEFLRGPL EGAPKPIAIE PCAGNRAAVL

1321    TVFLCLPRGS SGAPPPGQSG LAIASALIDI SQQKASDSKD KTSGVRNRKH LSTRQGTCV*
```

FIGURE 4(a)

```
  1 METGGRARTGTPQPAAPGVWRARPAGGGGGGASSW.LLDGNSWLLCYGFL  49
    ||  |  |||.|  ||||.| .||||||  |||||||| ||||||||||||
  1 MEPGVRARSGAPQPASPVLWRARPA..GGGGASSWLLLDGNSWLLCYGFL  48

50 YLALYAQVSQSKPCERTGSCFSGRCVNSTCLCDPGWVGDQCQHCQGRFKL  99
    ||||||||||||||||||||||||||||||||||||||||||||||||||
 49 YLALYAQVSQSKPCERTGSCFSGRCVNSTCLCDPGWVGDQCQHCQGRFKL  98

100 TEPSGYLTDGPINYKYKTKCTWLIEGYPNAVLRLRFNHFATECSWDHMYV 149
    ||||||||||||||||||||||||||||||||||||||||||||||||||
 99 TEPSGYLTDGPINYKYKTKCTWLIEGYPNAVLRLRFNHFATECSWDHMYV 148

150 YDGDSIYAPLIAVLSGLIVPEIRGNETVPEVVTTSGYALLHFFSDAAYNL 199
    |||||||||:|||||||||||:||||||||||||||||||||||||||||
149 YDGDSIYAPLVAVLSGLIVPEVRGNETVPEVVTTSGYALLHFFSDAAYNL 198

200 TGFNIFYSINSCPNNCSGHGKCTTSVSVPSQVYCECDKYWKGEACDIPYC 249
    ||||||||||||||||||||||||||||| ||||||||||||||||||||
199 TGFNIFYSINSCPNNCSGHGKCTTSVSVASQVYCECDKYWKGEACDIPYC 248

250 KANCGSPDHGYCDLTGEKLCVCNDSWQGPDCSLNVPSTESYWILPNVKPF 299
    ||||||||||||||||||||||||||||||||||||||||||||||||||
249 KANCGSPDHGYCDLTGEKLCVCNDSWQGPDCSLNVPSTESYWILPNVKPF 298

300 SPSVGRASHKAVLHGKFMWVIGGYTFNYSSFQMVLNYNLESSIWNVGTPS 349
    ||||||||||||||||||||||||||||||||||||||||||||||  |
299 SPSVGRASHKAVLHGKFMWVIGGYTFNYSSFQMVLNYNLESSIWNVGAVS 348

350 RGPLQRYGHSLALYQENIFMYGGRIETNDGNVTDELWVFNIHSQSWSTKT 399
    ||||||||||||||||||||||||.||.||||||||||||:  |||||||
349 RGPLQRYGHSLALYQENIFMYGGRMETSDGNVTDELWVFNVRSQSWSTKT 398

400 PTVLGHGQQYAVEGHSAHIMELDSRDVVMIIIFGYSAIYGYTSSIQEYHI 449
    ||||||  ||||||||||||||||||||||:|||||||||||||||||||
399 PTVLGHSQQYAVEGHSAHIMELDSRDVVMIVIFGYSAIYGYTSSIQEYHI 448

450 SSNTWLVPETKGAIVQGGYGHTSVYDEITKSIYVHGGYKALPGNKYGLVD 499
    ||||||||||||||||||||||||||||:|||||||||||||||||||||
449 SSNTWLVPETKGAIVQGGYGHTSVYDEVTKSIYVHGGYKALPGNKYGLVD 498

500 DLYKYEVNTKTWTILKESGFARYLHSAVLINGAMLIFGGNTHNDTSLSNG 549
    ||||||||:|||||||||||||||||||||||||||||||||||||||||
499 DLYKYEVNTRTWTILKESGFARYLHSAVLINGAMLIFGGNTHNDTSLSNG 548

550 AKCFSADFLAYDIACDEWKILPKPNLHRDVNRFGHSAVVINGSMYIFGGF 599
    |||||||||||||||||||:||||||||||||||||||||||||||||||
549 AKCFSADFLAYDIACDEWKTLPKPNLHRDVNRFGHSAVVINGSMYIFGGF 598

600 SSVLLNDILVYKPPNCKAFRDEELCKNAGPGIKCVWNKNHCESWESGNTN 649
    |||||||||||||||||||||||||:||||||||||||||||||||||||
599 SSVLLNDILVYKPPNCKAFRDEELCRNAGPGIKCVWNKNHCESWESGNTN 648

650 NILRAKCPPKTAASDDRCYRYADCASCTANTNGCQWCDDKKCISANSNCS 699
    ||||||||||||.|||||||||||||||||||||||||||||||.||||
649 NILRAKCPPKTAATDDRCYRYADCASCTANTNGCQWCDDKKCISASSNCS 698

700 MSVKNYTKCHVRNEQICNKLTSCKSCSLNLNCQWDQRQQECQALPAHLCG 749
    ||:||||||:||||||||||||||||||||||||||||||||||||||||
699 TSVRNYTKCHIRNEQICNKLTSCKSCSLNLNCQWDQRQQECQALPAHLCG 748

750 EGWSHIGDACLRVNSSRENYDNAKLYCYNLSGNLASLTTSKEVEFVLDEI 799
    |||.|:||||||:|||||.|||||||||||||||||||||||||||||||
749 EGWNHVGDACLRINSSRESYDNAKLYCYNLSGNLASLTTSKEVEFVLDEI 798
```

FIGURE 4(b)

```
 800 QKYTQQKVSPWVGLRKINISYWGWEDMSPFTNTTLQWLPGEPNDSGFCAY  849
     ||:|||||||||||||||||||||||||||||.|||||||||||||||||
 799 QKFTQQKVSPWVGLRKINISYWGWEDMSPFTNTSLQWLPGEPNDSGFCAY  848

850 LERAAVAGLKANPCTSMANGLVCEKPVVSPNQNARPCKKPCSLRTSCSNC  899
     ||||||||||||||||.|||||||||||||||||||||||||||||.||
 849 LERAAVAGLKANPCTSMADGLVCEKPVVSPNQNARPCKKPCSLRTSCANC  898

900 TSNGMECMWCSSTKRCVDSNAYIISFPYGQCLEWQTATCSPQNCSGLRTC  949
     ||.|||||||||||||||||||||||||||||||||||||||||||||||
 899 TSSGMECMWCSSTKRCVDSNAYIISFPYGQCLEWQTATCSPQNCSGLRTC  948

950 GQCLEQPGCGWCNDPSNTGRGHCIEGSSRGPMKLIGMHHNEMVLDTNLCP  999
     ||||||||||||||||||||||:|||||||||||:|.|..:.||||.|||
 949 GQCLEQPGCGWCNDPSNTGRGYCIEGSSRGPMKLVGVHNSDVVLDTSLCP  998

1000 KEKNYEWSFIQCPACQCNGHSTCINNNVCEQCKNLTTGKQCQDCMPGYYG 1049
     |||||||||||||||||||||||||||||||||||||:|||:||||||||
 999 KEKNYEWSFIQCPACQCNGHSTCINNNVCEQCKNLTTGRQCQECMPGYYG 1048

1050 DPTNGGQCTACTCSGHANICHLHTGKCFCTTKGIKGDQCQLCDSENRYVG 1099
     ||||||||||||| ||||:|||||||||||||||||||||||||||||||
1049 DPTNGGQCTACTCGGHANVCHLHTGKCFCTTKGIKGDQCQLCDSENRYVG 1098

1100 NPLRGTCYYSLLIDYQFTFSLLQEDDRHHTAINFIANPEQSNKNLDISIN 1149
     ||||||||||||||||||||||||||||||||||||||||||||||||||
1099 NPLRGTCYYSLLIDYQFTFSLLQEDDRHHTAINFIANPEQSNKNLDISIN 1148

1150 ASNNFNLNITWSVGSTAGTISGEETSIVSKNNIKEYRDSFSYEKFNFRSN 1199
     |||||||||||||||| ||||||| |||| ||||||||||||||||||||
1149 ASNNFNLNITWSVGSTGGTISGEETPIVSKTNIKEYRDSFSYEKFNFRSN 1198

1200 PNITFYVYVSNFSWPIKIQIAFSQHNTIMDLVQFFVTFFSCFLSLLLVAA 1249
     ||||||||||||||||||||||||||||||||||||||||||||||||||
1199 PNITFYVYVSNFSWPIKIQIAFSQHNTIMDLVQFFVTFFSCFLSLLLVAA 1248

1250 VVWKIKQTCWASRRREQLLRERQQMASRPFASVDVALEVGAEQTEFLRGP 1299
     ||||||||||||||||||||||||||||||||||||||||||||:|||||
1249 VVWKIKQTCWASRRREQLLRERQQMASRPFASVDVALEVGAEQTDFLRGP 1298

1300 LEGAPKPIAIEPCAGNRAAVLTVFLCLPRGSSGAPPPGQSGLAIASALID 1349
     ||||||||||||||||||||||||||||||||||||||||||||||||||
1299 LEGAPKPIAIEPCAGNRAAVLTVFLCLPRGSSGAPPPGQSGLAIASALID 1348

1350 ISQQKASDSKDKTSGVRNRKHLSTRQGTCV 1379
     |||||||.||||||||||||||||||||||
1349 ISQQKPSDNKDKTSGVRNRKHLSTRQGTCV 1378
```

FIGURE 5(a)

```
ATGGAGCCGGGGGTCCGGGCCCGCTCGGGTGCCCCGCAGCCGGCCTCCCCGGTGCTGTGG    (SEQ ID NO:18)
 M   E   P   G   V   R   A   R   S   G   A   P   Q   P   A   S   P   V   L   W   (SEQ ID NO:19)

AGGGCTCGGCCGGCGGGCGGTGGGGGCGCCTCCTCCTGGCTGCTGCTGGACGGGAACAGC
 R   A   R   P   A   G   G   G   G   A   S   S   W   L   L   L   D   G   N   S

TGGCTGCTGTGCTATGGCTTCCTCTACCTGGCGCTCTATGCTCAGGTGTCCCAGTCCAAG
 W   L   L   C   Y   G   F   L   Y   L   A   L   Y   A   Q   V   S   Q   S   K

CCCTGCGAGAGGACTGGCTCCTGCTTCTCCGGTCGCTGTGTCAACTCCACCTGCCTGTGC
 P   C   E   R   T   G   S   C   F   S   G   R   C   V   N   S   T   C   L   C

GACCCGGGCTGGGTTGGGGACCAGTGCCAGCACTGCCAGGGCAGGTTCAAGTTAACAGAA
 D   P   G   W   V   G   D   Q   C   Q   H   C   Q   G   R   F   K   L   T   E

CCTTCTGGATATTTAACAGATGGACCAATTAACTATAAATATAAAACAAAGTGTACATGG
 P   S   G   Y   L   T   D   G   P   I   N   Y   K   Y   K   T   K   C   T   W

CTAATTGAAGGCTATCCAAATGCAGTGCTAAGGTTAAGATTCAATCATTTTGCTACAGAA
 L   I   E   G   Y   P   N   A   V   L   R   L   R   F   N   H   F   A   T   E

TGCAGCTGGGATCATATGTATGTTTATGATGGAGATTCTATATACGCACCTTTAGTAGCT
 C   S   W   D   H   M   Y   V   Y   D   G   D   S   I   Y   A   P   L   V   A

GTACTTAGTGGCTTGATCGTTCCTGAAGTGAGGGGTAACGAGACCGTGCCTGAGGTGGTC
 V   L   S   G   L   I   V   P   E   V   R   G   N   E   T   V   P   E   V   V

ACGACGTCTGGCTACGCGCTGCTCCACTTTTTCAGCGATGCTGCATATAACCTAACTGGC
 T   T   S   G   Y   A   L   L   H   F   F   S   D   A   A   Y   N   L   T   G

TTCAACATTTTTTATTCGATCAATTCCTGTCCTAACAACTGCTCTGGTCATGGAAAGTGT
 F   N   I   F   Y   S   I   N   S   C   P   N   N   C   S   G   H   G   K   C

ACAACCAGTGTCTCTGTTGCAAGTCAAGTGTATTGTGAATGCGACAAATACTGGAAAGGG
 T   T   S   V   S   V   A   S   Q   V   Y   C   E   C   D   K   Y   W   K   G

GAAGCATGTGACATTCCTTACTGTAAAGCCAATTGTGGGAGTCCAGATCATGGCTACTGT
 E   A   C   D   I   P   Y   C   K   A   N   C   G   S   P   D   H   G   Y   C

GACCTAACAGGAGAGAAACTCTGTGTCTGCAACGATAGTTGGCAAGGCCCAGATTGTTCT
 D   L   T   G   E   K   L   C   V   C   N   D   S   W   Q   G   P   D   C   S

CTGAATGTCCCTTCTACTGAGTCTTACTGGATTTTGCCAAATGTTAAACCCTTCAGCCCT
 L   N   V   P   S   T   E   S   Y   W   I   L   P   N   V   K   P   F   S   P

TCCGTAGGTCGGGCCTCACATAAAGCAGTTTTACATGGGAAATTCATGTGGGTGATTGGA
 S   V   G   R   A   S   H   K   A   V   L   H   G   K   F   M   W   V   I   G

GGATATACTTTTAACTACAGTTCTTTTCAAATGGTTCTGAATTACAATTTAGAAAGCAGT
 G   Y   T   F   N   Y   S   S   F   Q   M   V   L   N   Y   N   L   E   S   S

ATATGGAATGTAGGTGCTGTATCAAGGGGCCCTCTTCAGAGATACGGACATTCTCTTGCC
 I   W   N   V   G   A   V   S   R   G   P   L   Q   R   Y   G   H   S   L   A

CTCTATCAGGAAAACATCTTTATGTACGGAGGCAGAATGGAGACCAGTGATGGCAACGTC
 L   Y   Q   E   N   I   F   M   Y   G   G   R   M   E   T   S   D   G   N   V

ACCGATGAATTATGGGTGTTTAACGTACGCAGTCAATCATGGAGCACGAAAACCCCCACT
 T   D   E   L   W   V   F   N   V   R   S   Q   S   W   S   T   K   T   P   T

GTCCTTGGCCACAGTCAGCAGTACGCTGTGGAGGGACACTCGGCACACATCATGGAGCTG
 V   L   G   H   S   Q   Q   Y   A   V   E   G   H   S   A   H   I   M   E   L

GACAGTAGAGACGTGGTCATGATTGTCATATTTGGATATTCTGCAATATATGGCTATACC
 D   S   R   D   V   V   M   I   V   I   F   G   Y   S   A   I   Y   G   Y   T

AGCAGCATACAGGAATACCATATCTCCTCAAACACTTGGCTAGTTCCAGAAACGAAAGGA
 S   S   I   Q   E   Y   H   I   S   S   N   T   W   L   V   P   E   T   K   G

GCCATTGTGCAAGGTGGATATGGCCACACAAGTGTGTATGACGAAGTGACCAAGTCCATC
 A   I   V   Q   G   G   Y   G   H   T   S   V   Y   D   E   V   T   K   S   I
```

FIGURE 5(b)

```
TATGTTCACGGAGGCTACAAAGCATTGCCTGGCAATAAGTACGGGCTGGTGGACGACCTC
 Y  V  H  G  G  Y  K  A  L  P  G  N  K  Y  G  L  V  D  D  L

TATAAGTACGAAGTCAACACCAGGACTTGGACTATTTTGAAAGAAAGTGGGTTTGCCAGA
 Y  K  Y  E  V  N  T  R  T  W  T  I  L  K  E  S  G  F  A  R

TACCTTCACTCAGCTGTTCTTATCAATGGAGCTATGCTTATTTTTGGAGGAAATACCCAT
 Y  L  H  S  A  V  L  I  N  G  A  M  L  I  F  G  G  N  T  H

AATGATACTTCCCTGAGTAACGGTGCAAAATGTTTTCTGCCGATTTCCTGGCATATGAC
 N  D  T  S  L  S  N  G  A  K  C  F  S  A  D  F  L  A  Y  D

ATAGCTTGTGACGAATGGAAGACATTGCCTAAACCAAATCTCCATAGAGACGTCAACCGA
 I  A  C  D  E  W  K  T  L  P  K  P  N  L  H  R  D  V  N  R

TTTGGGCATTCTGCAGTCGTCATCAATGGGTCAATGTATATATTTGGTGGATTTTCTAGT
 F  G  H  S  A  V  V  I  N  G  S  M  Y  I  F  G  G  F  S  S

GTACTCCTTAATGATATCCTTGTGTATAAACCCCCAAATTGCAAAGCTTTCCGAGATGAA
 V  L  L  N  D  I  L  V  Y  K  P  P  N  C  K  A  F  R  D  E

GAACTGTGCAGAAACGCTGGTCCAGGGATAAAATGTGTTTGGAATAAGAATCACTGTGAA
 E  L  C  R  N  A  G  P  G  I  K  C  V  W  N  K  N  H  C  E

TCTTGGGAGTCTGGGAATACAAATAATATTCTCAGAGCCAAGTGCCCTCCCAAGACAGCT
 S  W  E  S  G  N  T  N  N  I  L  R  A  K  C  P  P  K  T  A

GCTACCGATGACAGATGTTACAGATATGCTGACTGTGCCAGCTGCACAGCCAACACGAAC
 A  T  D  D  R  C  Y  R  Y  A  D  C  A  S  C  T  A  N  T  N

GGGTGCCAGTGGTGTGACGACAAGAAATGCATCTCAGCCAGCAGCAACTGCAGCACGTCT
 G  C  Q  W  C  D  D  K  K  C  I  S  A  S  S  N  C  S  T  S

GTCAGAAACTACACTAAATGTCATATAAGAAATGAGCAGATTTGTAACAAACTTACAAGC
 V  R  N  Y  T  K  C  H  I  R  N  E  Q  I  C  N  K  L  T  S

TGTAAAAGCTGTTCACTCAACTTGAATTGCCAGTGGGATCAGCGGCAGCAGGAATGTCAG
 C  K  S  C  S  L  N  L  N  C  Q  W  D  Q  R  Q  Q  E  C  Q

GCTTTGCCAGCTCACCTTTGTGGAGAAGGCTGGAATCATGTTGGGGACGCTTGTCTTCGA
 A  L  P  A  H  L  C  G  E  G  W  N  H  V  G  D  A  C  L  R

ATCAATTCCAGTCGAGAAAGCTATGATAATGCCAAACTTTATTGCTATAACCTCAGTGGA
 I  N  S  S  R  E  S  Y  D  N  A  K  L  Y  C  Y  N  L  S  G

AATCTCGCCTCCCTGACCACGTCCAAGGAGGTGGAGTTTGTGTTGGATGAAATACAGAAG
 N  L  A  S  L  T  T  S  K  E  V  E  F  V  L  D  E  I  Q  K

TTCACACAGCAGAAAGTGTCACCGTGGGTAGGCCTACGCAAGATCAACATATCCTACTGG
 F  T  Q  Q  K  V  S  P  W  V  G  L  R  K  I  N  I  S  Y  W

GGATGGGAGGACATGTCTCCTTTCACAAATACAAGCCTGCAGTGGCTTCCTGGTGAGCCA
 G  W  E  D  M  S  P  F  T  N  T  S  L  Q  W  L  P  G  E  P

AATGACTCTGGATTCTGTGCCTACTTAGAAAGGGCTGCAGTGGCAGGGTTAAAAGCAAAC
 N  D  S  G  F  C  A  Y  L  E  R  A  A  V  A  G  L  K  A  N

CCTTGCACATCCATGGCAGATGGACTCGTTTGTGAAAAGCCTGTAGTAAGCCCAAATCAG
 P  C  T  S  M  A  D  G  L  V  C  E  K  P  V  V  S  P  N  Q

AACGCGAGGCCGTGCAAGAAGCCGTGCTCCCTGAGGACCTCCTGCGCCAACTGCACGAGC
 N  A  R  P  C  K  K  P  C  S  L  R  T  S  C  A  N  C  T  S

AGCGGCATGGAGTGCATGTGGTGCAGCAGCACGAAGCGCTGTGTGGACTCCAACGCTTAC
 S  G  M  E  C  M  W  C  S  S  T  K  R  C  V  D  S  N  A  Y

ATCATCTCCTTTCCCTACGGACAGTGCCTGGAGTGGCAGACTGCCACCTGCTCGCCTCAA
 I  I  S  F  P  Y  G  Q  C  L  E  W  Q  T  A  T  C  S  P  Q

AATTGTTCTGGGTTAAGAACCTGTGGACAGTGCTTGGAGCAGCCAGGGTGTGGCTGGTGC
 N  C  S  G  L  R  T  C  G  Q  C  L  E  Q  P  G  C  G  W  C
```

FIGURE 5 (c)

```
AACGATCCTAGTAACACAGGAAGAGGCTATTGCATCGAAGGGTCTTCCCGGGGCCCAATG
 N  D  P  S  N  T  G  R  G  Y  C  I  E  G  S  S  R  G  P  M

AAACTCGTGGGGGTCCACAACAGTGACGTGGTTCTTGACACCAGCCTCTGCCCCAAGGAG
 K  L  V  G  V  H  N  S  D  V  V  L  D  T  S  L  C  P  K  E

AAGAACTACGAGTGGTCTTTTATCCAGTGTCCAGCTTGCCAGTGTAATGGACACAGCACG
 K  N  Y  E  W  S  F  I  Q  C  P  A  C  Q  C  N  G  H  S  T

TGCATCAACAACAACGTCTGTGAGCAGTGTAAGAATCTCACCACTGGGCGACAGTGTCAG
 C  I  N  N  N  V  C  E  Q  C  K  N  L  T  T  G  R  Q  C  Q

GAATGCATGCCAGGGTACTATGGAGACCCAACCAACGGTGGGCAGTGCACAGCTTGCACG
 E  C  M  P  G  Y  Y  G  D  P  T  N  G  G  Q  C  T  A  C  T

TGCGGCGGCCATGCGAACGTCTGTCACCTGCACACGGGAAAGTGTTTTTGCACAACCAAG
 C  G  G  H  A  N  V  C  H  L  H  T  G  K  C  F  C  T  T  K

GGGATCAAGGGTGACCAGTGCCAGCTATGTGACTCTGAAAATCGCTATGTTGGTAATCCA
 G  I  K  G  D  Q  C  Q  L  C  D  S  E  N  R  Y  V  G  N  P

CTTAGGGGGACATGCTATTACAGTCTTCTGATTGACTACCAGTTTACCTTCAGCTTGCTG
 L  R  G  T  C  Y  Y  S  L  L  I  D  Y  Q  F  T  F  S  L  L

CAGGAAGATGACCGGCACCACACTGCCATCAACTTCATCGCCAACCCAGAGCAGTCAAAC
 Q  E  D  D  R  H  H  T  A  I  N  F  I  A  N  P  E  Q  S  N

AAAAACTTGGACATTTCGATTAATGCTTCCAACAACTTTAATCTCAACATTACGTGGTCA
 K  N  L  D  I  S  I  N  A  S  N  N  F  N  L  N  I  T  W  S

GTTGGCTCAACAGGTGGAACCATATCTGGGGAAGAGACTCCTATAGTTTCTAAGACAAAT
 V  G  S  T  G  G  T  I  S  G  E  E  T  P  I  V  S  K  T  N

ATAAAGGAATACAGAGACAGCTTTTCCTATGAAAAATTTAACTTCAGAAGCAATCCTAAT
 I  K  E  Y  R  D  S  F  S  Y  E  K  F  N  F  R  S  N  P  N

ATCACATTTTATGTGTATGTCAGCAACTTCTCCTGGCCTATTAAAATACAGATTGCGTTT
 I  T  F  Y  V  Y  V  S  N  F  S  W  P  I  K  I  Q  I  A  F

TCACAACACAACACGATCATGGATCTCGTGCAGTTCTTTGTCACCTTCTTCAGTTGTTTT
 S  Q  H  N  T  I  M  D  L  V  Q  F  F  V  T  F  F  S  C  F

TTATCTTTACTGCTGGTGGCTGCTGTGGTCTGGAAGATCAAACAAACTTGCTGGGCTTCT
 L  S  L  L  L  V  A  A  V  V  W  K  I  K  Q  T  C  W  A  S

CGTCGGAGGGAGCAACTGCTTCGAGAACGACAGCAGATGGCCAGCCGTCCCTTTGCTTCT
 R  R  R  E  Q  L  L  R  E  R  Q  Q  M  A  S  R  P  F  A  S

GTTGATGTAGCCCTGGAAGTAGGAGCTGAACAGACAGACTTTCTGCGAGGGCCATTAGAG
 V  D  V  A  L  E  V  G  A  E  Q  T  D  F  L  R  G  P  L  E

GGTGCCCCTAAGCCAATAGCCATCGAACCCTGCGCTGGGAACAGAGCTGCTGTCCTGACT
 G  A  P  K  P  I  A  I  E  P  C  A  G  N  R  A  A  V  L  T

GTGTTTCTCTGTCTACCGAGAGGATCTTCAGGCGCCCCACCCCCTGGGCAGTCAGGCCTT
 V  F  L  C  L  P  R  G  S  S  G  A  P  P  P  G  Q  S  G  L

GCTATCGCCAGTGCCCTGATAGACATCTCACAGCAGAAGCCTTCTGATAATAAAGACAAG
 A  I  A  S  A  L  I  D  I  S  Q  Q  K  P  S  D  N  K  D  K

ACTTCTGGAGTCCGCAATCGGAAGCACCTCTCCACACGTCAAGGAACTTGTGTC
 T  S  G  V  R  N  R  K  H  L  S  T  R  Q  G  T  C  V
```

ATTRACTIN/MAHOGANY-LIKE POLYPEPTIDES

CROSS REFERENCE TO RELATED APPLICATIONS

This application is a divisional of U.S. patent application Ser. No. 10/154,670, filed May 23, 2002, which claims the benefit of priority under 35 U.S.C. §119 to U.S. Provisional Application Ser. No. 60/293,608, filed May 25, 2001, and to U.S. Provisional Application Ser. No. 60/324,626, filed Sep. 24, 2001, the disclosures of which are incorporated by reference herein.

FIELD OF THE INVENTION

The invention is directed to novel attractin/mahogany-like polypeptides and fragments thereof, polynucleotides encoding such polypeptides, processes for production of recombinant forms of such polypeptides, antibodies generated against these polypeptides or fragments, and assays and methods employing these polypeptides, antibodies, and polynucleotides.

BACKGROUND

Attractin (DPPT-L) is a human glycoprotein belonging to a family of proteins called the CUB family of cell adhesion and guidance proteins. Attractin is normally secreted by activated human T lymphocytes and modulates immune cell interactions.

Attractin is an 1198 amino acid protein containing four EGF-like domains along with other domains. Proteins with EGF-like domains typically play a role in extracellular signaling or cellular guidance. For example, purified-serum attractin and recombinant attractin enhance the proliferative response of peripheral blood mononuclear cells (PBMC) to recall antigens such as tetanus toxoid (Duke-Cohan et al., Proc. Nat. Acad. Sci., 95:11336-41, 1998). Attractin causes spreading of adherent monocytes to which lymphocytes attach (Duke-Cohan et al., supra). These adherent cells become the foci for T-lymphocyte clustering, and it is thought that attractin is involved in mediating the interactions between T-cells and macrophages, by influencing binding between the cells, antigen presentation, or by proteolytic modification. In addition attractin has also been identified as being related to the murine mahogany protein with a connection to control of pigmentation and energy metabolism (Tang et al., Proc. Nat. Acad. Sci., 97(11):6025-30, 2000).

Mahogany is a murine protein that is an ortholog of human attractin (Gunn et al., Nature, 398:152, 1999). Murine Mahogany is a transmembrane protein of 1428 amino acids, which contains a single transmembrane domain. The extracellular domain of murine mahogany has homology to attractin. Murine mahogany has been shown to be involved in suppression of obesity (Nagle et al., Nature, 398:148-152, 1999; see also U.S. Pat. No. 6,274,339, which is incorporated herein by reference in its entirety).

SUMMARY OF THE INVENTION

The invention provides a substantially pure polypeptide comprising an amino acid sequence that has at least 80%, 90% or 100% identity to a sequence as set forth in SEQ ID NO:2 or 19.

In addition, the invention provides a substantially pure polypeptide comprising an amino acid sequence that has at least 80%, 90% or 100% identity to a sequence as set forth from about amino acid 61 to 1379 of SEQ ID NO:2.

The invention also provides bioactive fragments of SEQ ID NO:2 comprising a sequence as set forth in SEQ ID NO:2 from amino acid 1 to 61, 61 to 1230, 61 to 1379, 1231 to 1252, or 1252 to 1379.

The invention further provides a substantially pure polypeptide comprising an amino acid sequence that has at least 80%, 90% or 100% identity to a sequence as set forth from about amino acid 61 to 1230 of SEQ ID NO:2.

The invention provides a substantially pure polypeptide having a sequence as set forth in SEQ ID NO:2 from amino acid 61 to amino acid 1230 operably linked to a sequence as set forth from about amino acid 1252 to 1379 of SEQ ID NO:2.

The invention also provides a fusion polypeptide comprising a first polypeptide comprising an amino acid sequence as set forth from about amino acid 61 to 1230 of SEQ ID NO:2 operably linked to a second polypeptide. In one aspect, the second polypeptide is an Fc polypeptide. In another aspect, the second polypeptide is a leucine zipper polypeptide. In yet another aspect the second polypeptide has a sequence as set forth in SEQ ID NO:2 or 19, including bioactive fragments thereof. In yet a further aspect a linker polypeptide separates the first polypeptide and the second polypeptide and is operably linked to the first and second polypeptide.

The invention further provides an isolated polynucleotide encoding the polypeptides of the invention. In one embodiment, the isolated polynucleotide comprises a sequence selected from the group consisting of: SEQ ID NO:1 or 18; SEQ ID NO:1 or 18, wherein T can also be U; sequences complementary to SEQ ID NO:1 or 18; and fragments of a), b), or c) that are at least 20 bases in length and that will hybridize under moderate to highly stringent conditions to a nucleic acid which encodes a polypeptide comprising a sequence as set forth in SEQ ID NO:2 or 19. In yet a further embodiment, the isolated polynucleotide comprising a sequence selected from the group consisting of: SEQ ID NO:1 from about nucleotide 181 to 4137; SEQ ID NO:1 from about nucleotide 181 to 3690; sequences complementary to SEQ ID NO:1 from about nucleotide 181 to 4137; sequences complementary to SEQ ID NO:1 from about nucleotide 181 to 3690; and any of a), b), c), or d) wherein T can also be U.

The invention further provides an isolated polynucleotide encoding a fusion polypeptide of the invention.

The invention provides a vector comprising a polynucleotide of the invention. In one embodiment, the vector is a is a plasmid or a viral vector.

The invention also provides a host cell comprising a vector of the invention. The invention further provides a recombinant host cell comprising a polynucleotide of the invention under the control of a heterologous regulatory sequence. The host cell can be prokaryotic or eukaryotic.

The invention further provides a method of producing a polypeptide comprising culturing a host cell or recombinant host cell of the invention under condition that promote expression of a polypeptide of the invention.

In another aspect of the invention a polypeptide is provided wherein the polypeptide is produced by culturing a host cell of the invention under conditions that promote expression of the polypeptide.

The invention also provides a purified antibody that specifically binds to a polypeptide of the invention. In one aspect the antibody is monoclonal. In another aspect the antibody is a human or humanized antibody.

The invention provides a pharmaceutical composition comprising an antibody of the invention or a polypeptide comprising an amino acid sequence selected from the group consisting of: SEQ ID NO:2 from amino acid 61 to 1379; and SEQ ID NO:2 from amino acid 61 to 1230, and a pharmaceutical carrier, excipient or diluent.

In another aspect, the invention provides a method for identifying an agent which modulates the expression of a polynucleotide comprising a sequence as set forth in SEQ ID NO:1 or 18, comprising contacting a sample containing the polynucleotide with a test agent and measuring the expression of the polynucleotide compared to a control, wherein a change in expression compared to the control is indicative of an agent that modulates expression of the polynucleotide. The agent can be a polypeptide, a peptide, a peptidomimetic, a nucleic acid, and a small molecule.

Also provided by the invention is a method for identifying an agent which modulates the activity of a polypeptide comprising a sequence selected from the group consisting of SEQ ID NO:2 or 19, SEQ ID NO:2 from about 61 to 1379, SEQ ID NO:2 from about 61 to 1230, comprising contacting a sample containing the polypeptide with a test agent and measuring the activity of the polypeptide compared to a control, wherein a change in activity compared to the control is indicative of an agent that modulates activity of the polypeptide.

The invention further provides a method of treating a HAM-associated disorder or disease comprising contacting a subject with a HAM polypeptide, HAM polynucleotide, or an antibody to a HAM polypeptide in an amount effective to treat the HAM-associated disorder or disease. The HAM-associated disorder is selected from the group consisting of a rheumatologic disorder, a bone marrow or solid organ transplant disorder, a graft-versus-host disorder, an inflammatory disorder, an autoimmune disorder, a neurologic disorder, a myelination disorder, a cell proliferative disorder, an infection, a cardiovascular disorder, a hematologic disorder, liver disorder, metabolic disorders, weight disorders, and a bone disorder. In one aspect the HAM polypeptide has a sequence as set forth in SEQ ID NO:2 or 19 or a bioactive fragment thereof.

BRIEF DESCRIPTION OF THE FIGURES

FIG. 1A-D shows a cDNA sequence and a corresponding polypeptide sequence of the invention. The arrows depict the primers used to amplify various fragments of the coding sequence.

FIG. 2A-C shows an alignment of the human Homologue of Attractin/Mahogony (HAM), human attractin and murine mahogany sequences.

FIG. 3A-B shows the putative domains of a HAM polypeptide of the invention.

FIG. 4A-B shows an alignment of a human HAM polypeptide of SEQ ID NO:2 with that of a murine HAM polypeptide of SEQ ID NO:19.

FIG. 5A-C shows the nucleotide sequence (SEQ ID NO:18) encoding the polypeptide sequence of SEQ ID NO:19.

DETAILED DESCRIPTION OF THE INVENTION

The present invention provides for the first time novel polypeptides having homology to attractin and mahogany proteins termed herein "HAM" for Homologue of Attractin and Mahogany. Also provided are polynucleotides encoding the novel HAM polypeptides as well as methods of use of the polynucleotides and polypeptides.

Attractin molecules modulate the interaction between T cells and macrophages and monocytes, permitting more rapid and/or more effective antigen presentation. The association of the three cell types is neither simultaneous nor random. Rather the antigen-presenting cell clusters first with the helper T cells, and this cluster acts as a focus for recognition by effector cells. In the absence of antigen, no proliferation occurs in soluble attractin-1-induced clusters of monocytes and T cells, but if a recall antigen such as tetanus toxoid is present; the clustering of cells maximizes the potential response to the antigen. Attractin may regulate local cytokine activity, either by influencing binding and presentation or by proteolytic modification. Soluble attractin-1 has recently been shown to cleave an N-terminal dipeptide which converts full-length RANTES 1-68 (consisting of amino acid residues 1-68), a potent monocyte chemoattractant, to RANTES 3-68, an equally potent inhibitor of monocyte chemotaxis. Soluble attractin-1 has also been found to bind to macrophages and monocytes. It is possible that it is via this binding that attractin, in any of its forms, may regulate the activity of macrophages and monocytes. For example, by providing requisite signals for the induction of spreading and subsequent enhanced T-cell clustering. Alternatively, the molecule could complement binding of another molecule to a receptor on macrophages/monocytes. Further, the molecule could form a bridge between T cells and macrophages/monocytes. Since membrane attractin-1 and -2 have a cytoplasmic domain it is likely that binding of a putative ligand to an extracellular region of the membrane attractin results in signaling to the T cell. It should be understood, however, that the invention is not limited by a particular mechanism of action.

Based upon their homology to attractins, the HAM molecules of the invention are predicted to have similar biological activity as the attractins and thus are predicted to play a role in inflammation and inflammatory responses. Other biological activities for the HAM molecules include energy metabolism and pigmentation, which activity is based upon HAM's homology to the mahogany protein and mahogany's role in the regulation of obesity (Nagle et al., Nature, 398:148-152, 1999). A correlation of the two types of activities (e.g., inflammatory and obesity) has been shown by higher white blood cell counts in obese children (Visser et al., supra) that are likely due to cytokines induced by inflammatory cell activation as well as additional cell types including preadipocytes. Preadipocytes exhibit functional features of macrophages, such as phagocytosis and anti-microbial activity, suggesting that preadipose cells could play a role in the inflammatory process or immune response (Cousin et al. J. Cell Physiol., 186:380-6, 2001).

Similar functional characteristics can be found in the ob gene product, Leptin, an adipocyte-derived peptide with circulating levels proportional to body fat mass. Serum leptin levels are correlated with adiposity and increased by as much as 3-4 fold in obese humans. The levels are lowered by fasting and increased by inflammation. Leptin, is a pleiotropic molecule that regulates food intake, metabolic and endocrine functions, and has a regulatory role in immunity, inflammation, and hematopoiesis (Fantuzzi and Faggioni, J. Leukoc Biol, 68(4):437-46, 2000). In addition to its role as a satiety signal, leptin is also pro-inflammatory: leptin receptors belong to the class I family of cytokine receptors and have been demonstrated on a variety of hematopoietic cells, including macrophages and T cells, in which leptin promotes the release of inflammatory cytokines. Thus, a link between inflammation and obesity exists (Visser et al., Pediatrics, 107(1):E13, 2001). Leptin's role in energy metabolism and inflammation is predictive of the role of HAM. Accordingly, HAM can play a role in obesity, inflammatory responses, inflammation, metabolism, pigmentation and neurological (e.g., myelination related disorders).

The HAM polypeptides, polynucleotides and antibodies provided herein find use in the treatment of inflammatory disease, obesity, energy metabolism, appetite, and the modulation of inflammatory responses.

The invention provides polypeptides referred to herein as "HAM polypeptides". As used herein a "HAM polypeptide" of the invention means a polypeptide which contains or comprises an amino acid sequence as set forth in SEQ ID NO:2 or 19; polypeptides having substantial homology or substantial identity to the sequence set forth in SEQ ID NO:2 or 19; fragments of the foregoing sequence (e.g., bioactive fragments); and conservative variants of the foregoing. The HAM polypeptides have been shown to have homology to attractin and mahogany polypeptides and thus have predicted function and biological activity similar to attractin and mahogany polypeptides.

As used herein, "polypeptide" means any chain of amino acids (including L- or D-amino acids), regardless of length or post-translational modification (e.g., glycosylation or phosphorylation), and include natural proteins, synthetic or recombinant polypeptides and fragments as well as a recombinant molecule consisting of a hybrid with a first portion, for example, having all or part of a HAM polypeptide amino acid sequence and a second portion comprising all or part of a polypeptide of interest. Typically, the HAM polypeptide is substantially pure of other components from which it is normally present in nature. The term "substantially pure" or "purified" when referring to a polypeptide, means a polypeptide that is at least 30% free from the proteins and naturally-occurring organic molecules with which it is naturally associated. Preferably the substantially pure polypeptide of the invention is at least 35-50%, preferably 60-70%, more preferably 75%, more preferably at least 90%, and most preferably at least 99% by weight purified from other naturally occurring organic molecules. A substantially pure polypeptide of the invention can be obtained, for example, by extraction from a natural source, by expression of a recombinant polynucleotide encoding the polypeptide, or by chemically synthesizing the polypeptide. Purity can be measured by any appropriate method, e.g., column chromatography, polyacrylamide gel electrophoresis, or HPLC analysis.

In general, a recombinant polypeptide or fragment can be isolated from a host cell if not secreted, or from the medium or supernatant if soluble and secreted, followed by one or more rounds of concentration, salting-out, ion exchange, hydrophobic interaction, affinity purification or size exclusion chromatography. If desired, the culture medium first can be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed, including various insoluble matrices comprising sulfopropyl or carboxymethyl groups. In addition, a chromatofocusing step or, alternatively, a hydrophobic interaction chromatography step can be employed. Suitable matrices can be phenyl or octyl moieties bound to resins. In addition, affinity chromatography with a matrix, which selectively binds the recombinant protein, can be employed. Examples of such resins employed are lectin columns, dye columns, and metal-chelating columns. Finally, one or more reversed-phase high performance liquid chromatography (RP-HPLC) steps employing hydrophobic RP-HPLC media, (e.g., silica gel or polymer resin having pendant methyl, octyl, octyldecyl or other aliphatic groups) can be employed to further purify the polypeptides. Some or all of the foregoing purification steps, in various combinations, are well known and can be employed to provide a substantially purified polypeptide of the invention.

It is also possible to utilize an affinity column comprising a polypeptide-binding protein, such as a monoclonal antibody generated against a polypeptide of the invention, to affinity-purify expressed polypeptides. These polypeptides can be removed from an affinity column using conventional techniques, e.g., in a high salt elution buffer and then dialyzed into a lower salt buffer for use or by changing pH or other components depending on the affinity matrix utilized, or be competitively removed using the naturally occurring substrate of the affinity moiety, such as a polypeptide derived from the invention.

Accordingly, polypeptide-binding proteins, such as anti-polypeptide antibodies or other proteins that may interact with a polypeptide of the invention, can be bound to a solid phase support such as a column chromatography matrix or a similar substrate suitable for identifying, separating, or purifying cells that express polypeptides of the invention on their surface. Adherence of polypeptide-binding proteins of the invention to a solid phase contacting surface can be accomplished by any means, for example, magnetic microspheres can be coated with these polypeptide-binding proteins and held in the incubation vessel through a magnetic field. Suspensions of cell mixtures are contacted with the solid phase that has such polypeptide-binding proteins thereon. Cells having polypeptides of the invention on their surface bind to the fixed polypeptide-binding protein and unbound cells then are washed away. This affinity-binding method is useful for purifying, screening, or separating such polypeptide-expressing cells from solution. The cells can be released, for example, by using a preferably non-toxic enzyme that cleaves the cell-surface binding partner, or by effecting such release by modifying the composition of the buffer.

Alternatively, mixtures of cells suspected of containing HAM polypeptide-expressing cells of the invention can be incubated with a biotinylated polypeptide-binding protein, such as an anti-HAM antibody. Sufficient binding usually occurs within about one hour, after which the mixture then is passed through a column packed with avidin-coated beads, to which the biotin moiety will bind with high affinity (see Berenson, et al. J. Cell. Biochem., 10D:239, 1986). Unbound cells are washed free of the column, and bound cells are eluted according to conventional methods. This method can be used to isolate cells expressing membrane-bound HAM polypeptides.

When purifying polypeptides, the desired degree of purity will depend on the intended use of the polypeptide. A relatively high degree of purity is desired when the polypeptide is to be administered in vivo, for example. In such a case, the polypeptides typically are purified such that no bands corresponding to other proteins are detectable by SDS-polyacrylamide gel electrophoresis (SDS-PAGE). One skilled in the art will understand that multiple bands corresponding to the polypeptide may be visualized by SDS-PAGE, due to differential glycosylation, differential post-translational processing, and the like. Most preferably, the polypeptide of the invention is purified to substantial homogeneity, as indicated by a single protein band upon analysis by SDS-PAGE. The band may be visualized by silver staining, Coomassie blue staining, or (if the protein is radiolabeled) by autoradiography.

Several distinct regions can be discerned within a human HAM polypeptide of the invention. A leader sequence, also called a signal peptide, is present in these polypeptides. For example, a leader sequence present in the full-length polypeptide of the invention is predicted to include amino acids 1-60 of SEQ ID NO:2. The signal peptide cleavage site for HAM was predicted using a computer algorithm. However, one of skill in the art will recognize that the cleavage site of the signal sequence may vary depending upon a number of factors including the organism in which the polypeptide is expressed. Accordingly, the N-terminus of a mature form of a HAM polypeptide of the invention may vary by about 2 to 5 amino acids. Thus, a mature form of the HAM polypeptide comprising SEQ ID NO:2 may include at its N-terminus amino acids 55, 56, 57, 58, 59, 60, 61, 62, 63, 64, or 65 of SEQ ID NO:2. Accordingly, a mature form can include amino acid 55, 56, 57, 58, 59, 60, 61, 62, 63, 64, or 65 to about amino acid 1379 (or, in the case of a soluble polypeptide, to amino acid 1230) of SEQ ID NO:2. The extracellular regions of the HAM polypeptide of SEQ ID NO:2 are located from about amino acids 61 to 1230 of SEQ ID NO:2. The EGF-like domains, CUB domain, C-type Lectin or carbohydrate-recognition domain (CLECT domain), KELCH motif and Laminin EGF-like domain assignments, as well as those for the transmembrane and cytoplasmic domains are based upon computer algorithms and on previous reports (Gunn et al., Nature 398: 152-157, 1999). For example, the extracellular region of human HAM putatively contains three EGF-like domains, a CUB domain, a KELCH motif, a C-type Lectin or carbohydrate-recognition domain, a putative ligand binding motif of the common gamma cytokine chain, and a Laminin EGF-like domain located at about amino acids 63-90, 211-244, 261-280, 93-208, 581-612, 749-873, 670-686, and 1014-1055 of SEQ ID NO:2, respectively (see FIG. 3). The transmembrane region for the HAM polypeptides are located at about amino acids 1231 to 1251 of SEQ ID NO:2. The intracellular regions are located at about amino acids 1252 to 1379 of SEQ ID NO:2. FIGS. 2 and 3 show the relative domains and conserved cysteine residues of HAM indicative of an attractin or mahogany polypeptide. Utilizing the alignment provided in FIG. 4A-B the putative domains of the murine HAM polypeptide (SEQ ID NO:19) based upon the corresponding domains in the human HAM polypeptide (SEQ ID NO:2) can be determined. The relative domains of the murine HAM polypeptide (SEQ ID NO:19) and the corresponding polynucleotide fragments encoding such domains (e.g., fragments of SEQ ID NO:18) are specifically encompassed by the present invention.

Accordingly, several distinct regions can be discerned within a murine HAM polypeptide of the invention. A leader sequence, also called a signal peptide, is present in these polypeptides. For example, a leader sequence present in the full-length polypeptide of the invention is predicted to include amino acids 1-59 of SEQ ID NO:19. The signal peptide cleavage site for murine HAM was predicted using a computer algorithm and alignment with human HAM. However, one of skill in the art will recognize that the cleavage site of the signal sequence may vary depending upon a number of factors including the organism in which the polypeptide is expressed. Accordingly, the N-terminus of a mature form of a murine HAM polypeptide of the invention may vary by about 2 to 5 amino acids. Thus, a mature form of a murine HAM polypeptide comprising SEQ ID NO:19 may include at its N-terminus amino acids 54, 55, 56, 57, 58, 59, 60, 61, 62, 63, or 64 of SEQ ID NO:19. Accordingly, a mature form can include amino acid 54, 55, 56, 57, 58, 59, 60, 61, 62, 63, or 64 to about amino acid 1378 (or, in the case of a soluble polypeptide, to amino acid 1229) of SEQ ID NO:2. The extracellular regions of a murine HAM polypeptide of SEQ ID NO:19 are located from about amino acids 60 to 1229 of SEQ ID NO:19. The EGF-like domains, CUB domain, C-type Lectin or carbohydrate-recognition domain (CLECT domain), KELCH motif and Laminin EGF-like domain assignments, as well as those for the transmembrane and cytoplasmic domains are based upon computer algorithms, alignments with human HAM (SEQ ID NO:2) and on previous reports (Gunn et al., Nature 398:152-157, 1999). For example, the extracellular region of murine HAM putatively contains three EGF-like domains, a CUB domain, a KELCH motif, a C-type Lectin or carbohydrate-recognition domain, a putative ligand binding motif of the common gamma cytokine chain, and a Laminin EGF-like domain located at about amino acids 62-89, 210-243, 260-279, 92-207, 580-611, 748-872, 669-685, and 1013-1054 of SEQ ID NO:19, respectively. The transmembrane region for a murine HAM polypeptide is located at about amino acids 1230 to 1250 of SEQ ID NO:19. The intracellular regions are located at about amino acids 1251 to 1378 of SEQ ID NO:19.

The invention provides both full-length and mature forms of HAM polypeptides. Full-length polypeptides are those having the complete primary amino acid sequence of the polypeptide as initially translated. The amino acid sequences of full-length polypeptides can be obtained, for example, by translation of the complete open reading frame ("ORF") of a cDNA molecule. Several full-length polypeptides may be encoded by a single genetic locus if multiple mRNA forms are produced from that locus by alternative splicing or by the use of multiple translation initiation sites. An example of a full length HAM polypeptide of the invention comprises amino acid 1 to amino acid 1379 of SEQ ID NO:2 and 1 to 1378 of SEQ ID NO:19. Such a full length polypeptide is contemplated to include, for example, the signal peptide comprising amino acids 1 to about amino acid 60 of SEQ ID NO:2 and amino acids 1 to about amino acid 59 of SEQ ID NO:19, respectively.

The "mature form" of a polypeptide refers to a polypeptide that has undergone post-translational processing steps, if any, such as, for example, cleavage of the signal sequence or proteolytic cleavage to remove a prodomain. Multiple mature forms of a particular full-length polypeptide may be produced, for example, by imprecise cleavage of the signal sequence, or by differential regulation of proteases that cleave the polypeptide. The mature form(s) of such polypeptide may be obtained by expression, in a suitable mammalian cell or other host cell, of a polynucleotide that encodes the full-length polypeptide. The sequence of the mature form of the polypeptide may also be determinable from the amino acid sequence of the full-length form, through identification of signal sequences or protease cleavage sites (e.g., a protease cleavage site is predicted between the Ser-Lys residues at positions 60 and 61 of SEQ ID NO:2). An example of a mature form of a HAM polypeptide of the invention comprises a sequence as set forth from about amino acid 61 to amino acid 1379 of SEQ ID NO:2.

The HAM polypeptides of the invention also include polypeptides that result from post-transcriptional or post-translational processing events such as alternate mRNA processing which can yield a truncated but biologically active polypeptide, for example, a naturally occurring soluble form of the polypeptide. Also encompassed within the invention are variations attributable to proteolysis such as differences in the N- or C-termini upon expression in different types of host cells, due to proteolytic removal of one or more terminal amino acids from the polypeptide (generally from 1-5 terminal amino acids).

In another embodiment, the invention provides bioactive fragments of a HAM polypeptide. By "bioactive fragment" means a fragment of SEQ ID NO:2 or 19 having a biological activity associated with an attractin and/or mahogany polypeptide and/or a biological activity associated with a full-length or mature form of a HAM polypeptide of the invention. A bioactive fragment may have one or more of the following biological activities including, for example, inducing monocyte and macrophage activation, promoting the secretion and/or expression of pro-inflammatory cytokines (e.g., IL-6), modulating metabolic activity, modulating weight gain/loss, and modulating appetite and energy consumption. Examples of bioactive fragments of a HAM polypeptide molecules include those having a sequence as set forth in SEQ ID NO:2 comprising about amino acid 61 to 1230 or as set forth in SEQ ID NO:19 comprising about amino acid 60 to 1229 and fragments of either of the foregoing. Such bioactive fragments represent potential soluble molecules lacking the predicted transmembrane domain (e.g., the domain beginning at about amino acid 1231 to amino acid 1251 of SEQ ID NO:2). Bioactive fragment of HAM polypeptides are capable of interacting, for example, with a HAM polypeptide cognate, or with an antibody developed against a HAM polypeptide of SEQ ID NO:2 or 19. Methods of determining whether a HAM polypeptide or bioactive fragment of a HAM polypeptide of the invention has a desired activity can be accomplished by assaying the polypeptide by any of the methods described below.

Accordingly, the polypeptides of the invention may be membrane-bound or they may be secreted and thus soluble. Soluble polypeptides are capable of being secreted from the cells in which they are expressed. In general, soluble polypeptides may be identified (and distinguished from non-soluble membrane-bound counterparts) by separating intact cells which express the desired polypeptide from the culture medium, e.g., by centrifugation, and assaying the medium (supernatant) for the presence of the desired polypeptide or by contacting cell-free media obtained from the culture with an antibody specific for HAM. The presence of polypeptide in the medium indicates that the polypeptide was secreted from the cells and thus is a soluble form of the polypeptide.

In one embodiment, the soluble polypeptides (e.g., a bioactive fragment of a HAM polypeptide) comprise all or part of the extracellular domain, but lack the transmembrane domain that would cause retention of the polypeptide in a cell membrane. In some embodiments the soluble polypeptide lacks a transmembrane domain in addition to one or more additional domains including, for example, the signal sequence or cytoplasmic domain. A soluble polypeptide according to the invention may include the cytoplasmic domain, or a portion thereof, so long as the polypeptide is secreted from the cell in which it is produced.

In general, the use of soluble forms is advantageous for certain applications. Purification of the polypeptides from recombinant host cells is facilitated, since the soluble polypeptides are secreted from the cells. Further, soluble polypeptides are generally more suitable for intravenous administration.

The invention also provides polypeptides and fragments of the extracellular domain that retain the capacity to modulate inflammatory responses, immune system activity weight gain/loss, and/or energy metabolism. Such a fragment may be a soluble polypeptide, as described above.

Also provided herein are polypeptide fragments comprising at least 25, or at least 30 contiguous amino acids of a sequence as set forth in SEQ ID NO:2 or 19. Fragments derived from the cytoplasmic domain find use in studies of signal transduction, and in regulating cellular processes associated with transduction of biological signals, such as inhibitory signals, and in identifying small molecule mimics or inhibitors of receptor interaction with signaling molecules. Polypeptide fragments comprising at least about 8 to 11, or more preferably 10 to 30, contiguous amino acids of SEQ ID NO:2 or 19 also may be employed as immunogens for generating antibodies, as well as larger polypeptides.

Naturally occurring variants and derived variants of the disclosed polypeptides and fragments are provided herein. Variants may exhibit amino acid sequences that are at least 80% identical to the disclosed polypeptides and fragments. Also provided are polypeptides or fragments comprising an amino acid sequence that is at least 85% identical, at least 90% identical, at least 95% identical, at least 98% identical, at least 99% identical, or at least 99.9% identical to the amino acid sequences disclosed herein. Percent identity may be determined by visual inspection and mathematical calculation. Alternatively, the percent identity of two protein sequences can be determined by comparing sequence information using a computer program, such as the GAP program, based on the algorithm of Needleman and Wunsch (J. Mol. Bio. 48:443, 1970) and available from the University of Wisconsin Genetics Computer Group (UWGCG). The preferred default parameters for the GAP program include: (1) a scoring matrix, blosum62, as described by Henikoff and Henikoff (Proc. Natl. Acad. Sci. USA 89:10915, 1992); (2) a gap weight of 12; (3) a gap length weight of 4; and (4) no penalty for end gaps. Similar comparison parameters can be implemented using other computer programs such as, for example, BESTFIT, FASTA, TFASTA (see, e.g., Wisconsin Genetics Software Package, Genetics Computer Group, 575 Science Dr., Madison, Wis.), or PILEUP (a simplification of the progressive alignment method of Feng & Doolittle, J. Mol. Evol. 35:351-360 (1987)).

The variants of the invention include, for example, those that result from alternate mRNA splicing events or from proteolytic cleavage. Alternate splicing of mRNA may, for example, yield a truncated but biologically active protein, such as a naturally occurring soluble form of the protein. Variations attributable to proteolysis include, for example, differences in the N- or C-termini upon expression in different types of host cells, due to proteolytic removal of one or more terminal amino acids from the protein (generally from 1-5 terminal amino acids). Proteins in which differences in amino acid sequence are attributable to genetic polymorphism (allelic variation among individuals producing the protein) are also contemplated herein.

Additional variants within the scope of the invention include polypeptides that may be modified to create derivatives thereof by forming covalent or aggregate conjugates with other chemical moieties, such as glycosyl groups, lipids, phosphate, acetyl groups and the like. Covalent derivatives may be prepared by linking the chemical moieties to functional groups on amino acid side chains or at the N-terminus or C-terminus of a polypeptide. Conjugates comprising diagnostic (detectable) or therapeutic agents attached thereto are contemplated herein, as discussed in more detail below.

Other derivatives include covalently bonded or aggregate conjugates of the polypeptides with other proteins or polypeptides, such as by synthesis in recombinant culture as N-terminal or C-terminal fusions. Examples of fusion polypeptides are discussed below in connection with oligomers. Further, fusion polypeptides can comprise peptides added to facilitate purification and identification. Such peptides include, for example, poly-His or the antigenic identification peptides described in U.S. Pat. No. 5,011,912 and in Hopp et al., *Bio/Technology* 6:1204, 1988. One such peptide is the FLAG® peptide, Asp-Tyr-Lys-Asp-Asp-Asp-Asp-Lys (SEQ ID NO:3), which is highly antigenic and provides an epitope reversibly bound by a specific monoclonal antibody, enabling rapid assay and facile purification of expressed recombinant protein. A murine hybridoma designated 4E11 produces a monoclonal antibody that binds the FLAG® peptide in the presence of certain divalent metal cations, as described in U.S. Pat. No. 5,011,912, hereby incorporated by reference. The 4E11 hybridoma cell line has been deposited with the American Type Culture Collection under accession no. HB 9259. Monoclonal antibodies that bind the FLAG® peptide are available from Eastman Kodak Co., Scientific Imaging Systems Division, New Haven, Conn.

Among the variant polypeptides provided herein are variants of native HAM polypeptides that retain the native binding properties or biological activity of a mature HAM polypeptide of SEQ ID NO:2 or 19 or the substantial equivalent thereof. For example a variant includes a molecule that binds its binding partner with essentially the same binding affinity as does the native form. Binding affinity can be measured by conventional procedures, e.g., as described in U.S. Pat. No. 5,512,457 and as set forth below.

Variants include polypeptides that are substantially homologous to the native form, but which have an amino acid sequence different from that of the native form because of one or more deletions, insertions or substitutions. Particular embodiments include, but are not limited to, polypeptides that comprise from one to ten deletions, insertions or substitutions of amino acid residues, when compared to a native sequence.

A given amino acid may be replaced, for example, by a residue having similar physiochemical characteristics. Examples of such conservative substitutions include substitution of one aliphatic residue for another, such as Ile, Val, Leu, or Ala for one another; substitutions of one polar residue for another, such as between Lys and Arg, Glu and Asp, or Gln and Asn; or substitutions of one aromatic residue for another, such as Phe, Trp, or Tyr for one another. Other conservative substitutions, e.g., involving substitutions of entire regions having similar hydrophobicity characteristics, are well known. Also included are the substitution of L-amino acids for D-amino acids. The presence of D-amino acids provides resistance to proteases and increases the stability of a polypeptide or fragment thereof. Amino acid substitutions and other alterations (deletions, insertions, and the like) to a HAM polypeptide of the invention is predicted to be more likely to alter or disrupt HAM polypeptide activities if they result in changes to the conserved residues indicated by the "consensus," indicated in FIG. 2A-C. Conversely, if a change is made to a HAM polypeptide resulting in substitution of one or more FIG. 2 consensus sequence residues for the HAM polypeptide residue at that conserved position, it is less likely that such an alteration will affect HAM polypeptide function. In one aspect, the invention provides HAM polypeptides that have from 1-10 amino acid substitutions, insertions, and/or deletions.

Similarly, the polynucleotides of the invention include variants that differ from a native HAM polynucleotide because of one or more deletions, insertions or substitutions, but that encode a biologically active polypeptide.

In addition, "conservatively modified variants" applies to both polypeptides and polynucleotides. With respect to a particular polynucleotide, conservatively modified variants refer to codons in the polynucleotide which encode identical or essentially identical amino acids. Because of the degeneracy of the genetic code, a large number of functionally identical polynucleotides encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such variations are "silent variations," which are one species of conservatively modified variations. Every polynucleotide sequence herein that encodes a polypeptide also describes every possible silent variation of the nucleic acid. One of skill will recognize that each codon in a polynucleotide (except AUG, which is ordinarily the only codon for methionine) can be modified to yield a functionally identical molecule. Accordingly, each silent variation of a nucleic acid that encodes a polypeptide is implicit in each described sequence.

The invention further includes polypeptides of the invention with or without associated native-pattern glycosylation. Polypeptides expressed in yeast or mammalian expression systems (e.g., COS-1 or COS-7 cells) can be similar to or significantly different from a native polypeptide in molecular weight and glycosylation pattern, depending upon the choice of expression system. Expression of any of the polypeptides of the invention in bacterial expression systems, such as *E. coli*, provides non-glycosylated forms of the polypeptides. Further, a given preparation may include multiple differentially glycosylated species of the protein. Glycosyl groups can be removed through conventional methods, in particular those utilizing glycopeptidase. In general, glycosylated polypeptides of the invention can have their carbohydrate moieties removed by being incubated with a molar excess of glycopeptidase (Boehringer Mannheim).

N-glycosylation sites in eukaryotic polypeptides are characterized by an amino acid triplet Asn-X-Y, wherein X is any amino acid except Pro and Y is Ser or Thr. The HAM polypeptides of the invention have a number of putative glycosylations sites. For example, the Asn residue at one or more of the following positions is a potential glycosylation site: 76N, 174N, 198N, 214N, 272N, 326N, 380N, 542N, 590N, 697N, 704N, 763N, 778N, 817N, 831N, 842N, 898N, 942N, 1033N, 1149N, 1157N, 1201N, and 1210N of SEQ ID NO:2. Murine HAM also has putative glycosylation sites at 75N, 173N, 197N, 213N, 271N, 325N, 380N, 541N, 589N, 696N, 703N, 762N, 777N, 816N, 830N, 841N, 897N, 941N, 1032N, 1148N, 1156N, 1200N, and 1209N of SEQ ID NO:19. N-glycosylation sites in the polypeptide extracellular domain can be modified to preclude glycosylation, allowing expression of a reduced carbohydrate analog in mammalian and yeast expression systems. Accordingly, modifications (e.g., treatment with a glycopeptidase) or substitutions or deletions of these residues can modulate the activity of a mature HAM polypeptide of the invention.

Correspondingly, similar polynucleotide constructs that encode various additions or substitutions of amino acid residues or sequences, or deletions of terminal or internal residues or sequences are encompassed by the invention. Appropriate substitutions, additions, or deletions to the nucleotide sequence encoding these triplets (e.g., Asn-X-Y) will result in prevention of attachment of carbohydrate residues at the Asn side chain. Alteration of a single nucleotide, chosen so that Asn is replaced by a different amino acid, for example, is sufficient to inactivate an N-glycosylation site. Alternatively, a Ser or Thr in the triplet can by replaced with another amino acid, such as Ala. Known procedures for inactivating N-glycosylation sites in proteins include those described in U.S. Pat. No. 5,071,972 and EP 276,846. One of skill in the art can identify the codons corresponding to the Asn residues for HAM as described above, as well as the Ser and Thr residues of the Asn-X-Y triplet.

In another example of variants, sequences encoding Cys residues that are not essential for biological activity can be altered to cause the Cys residues to be deleted or replaced with other amino acids, preventing formation of incorrect intramolecular disulfide bridges upon folding or renaturation. A number of putative conserved Cys residues of a HAM polypeptide of the invention are identified in the alignment provided in FIG. 2 and FIG. 4.

Other variants are prepared by modification of adjacent dibasic amino acid residues, to enhance expression in yeast systems in which KEX2 protease activity is present. EP 212, 914 discloses the use of site-specific mutagenesis to inactivate KEX2 protease processing sites in a protein. KEX2 protease processing sites are inactivated by deleting, adding or substituting residues to alter Arg-Arg, Arg-Lys, and Lys-Arg pairs to eliminate the occurrence of these adjacent basic residues. Lys-Lys pairings are considerably less susceptible to KEX2 cleavage, and conversion of Arg-Lys or Lys-Arg to Lys-Lys represents a conservative and preferred approach to inactivating KEX2 sites.

Oligomers

Encompassed by the invention are oligomers and fusion polypeptides, that comprises a HAM polypeptide or a bioactive fragment thereof linked to a polypeptide of interest. In a preferred embodiment, the fusion partner is linked to the C-terminus of the HAM polypeptide or a bioactive fragment thereof. Such oligomers may be in the form of covalently-linked or non-covalently-linked multimers, including dimers, trimers, or higher oligomers. As noted above, preferred polypeptides are soluble and thus these oligomers typically comprise soluble polypeptides. In one aspect of the invention, the oligomers maintain the binding ability of the polypeptide components and provide therefor, bivalent, trivalent, and the like, binding sites.

One embodiment of the invention is directed to oligomers comprising multiple polypeptides joined via covalent or non-covalent interactions between peptide moieties fused to the polypeptides. Such peptide moieties may be peptide linkers (spacers), or peptides that have the property of promoting oligomerization. Examples of peptide linkers include --Gly-Gly--, GGGGS (SEQ ID NO:4) (GGGGS)$_n$ (SEQ ID NO:5), GKSSGSGSESKS (SEQ ID NO:6), GSTSGSGKSSEGKG (SEQ ID NO:7), GSTSGSGKSSEGSGSTKG (SEQ ID NO:8), GSTSGSGKPGSGEGSTKG (SEQ ID NO:9), or EGKSSGSGSESKEF (SEQ ID NO:10). Linking moieties are described, for example, in Huston, J. S., et al., PNAS 85:5879-5883 (1988), Whitlow, M., et al., Protein Engineering 6:989-995 (1993), and Newton, D. L., et al., Biochemistry 35:545-553 (1996). Other suitable peptide linkers are those described in U.S. Pat. Nos. 4,751,180 and 4,935,233, which are hereby incorporated by reference. A polynucleotide encoding a desired peptide linker can be inserted between, and in the same reading frame as, a polynucleotide encoding a HAM polypeptide or bioactive fragment of the invention, using any suitable conventional technique. In particular embodiments, a fusion polypeptide comprises from two to four bioactive fragments of a HAM polypeptide (e.g., a soluble fragment), separated by peptide linkers. In one embodiment, the invention provides a fusion polypeptide having an Fc polypeptide domain and a HAM polypeptide or bioactive fragment (e.g., a fragment as set forth in SEQ ID NO:2 from about amino acid 61 to 1230). Leucine zippers and certain polypeptides derived from antibodies are among the peptides that can promote oligomerization of the polypeptides attached thereto, as described in more detail below.

As one alternative, an oligomer or fusion polypeptide is prepared using polypeptides derived from immunoglobulins. Preparation of fusion polypeptides comprising certain heterologous polypeptides fused to various portions of antibody-derived polypeptides (including the Fc domain) has been described, e.g., by Ashkenazi et al. (*PNAS USA* 88:10535, 1991); Byrn et al. (*Nature* 344:677, 1990); and Hollenbaugh and Aruffo ("Construction of Immunoglobulin Fusion Proteins", in *Current Protocols in Immunology*, Suppl. 4, pages 10.19.1-10.19.11, 1992).

One embodiment of the present invention is directed to a dimer comprising two fusion proteins created by fusing a HAM polypeptide or bioactive fragment of the invention to an Fc polypeptide derived from an antibody. A gene fusion encoding a HAM polypeptide/Fc fusion protein is inserted into an appropriate expression vector. HAM polypeptide/Fc fusion proteins are expressed in host cells transformed with the recombinant expression vector, and allowed to assemble much like antibody molecules, whereupon interchain disulfide bonds form between the Fc moieties to yield divalent molecules.

An Fc polypeptide includes native and mutein forms of polypeptides made up of the Fc region of an antibody comprising any or all of the CH domains of the Fc region. Truncated forms of such polypeptides containing the hinge region that promotes dimerization are also included. Preferred polypeptides comprise an Fc polypeptide derived from a human IgG1 antibody. The Fc polypeptides preferably are linked to the COOH-terminus of a HAM polypeptide or bioactive fragment of the invention.

One suitable Fc polypeptide, described in PCT application WO 93/10151 (hereby incorporated by reference), is a single chain polypeptide extending from the N-terminal hinge region to the native C-terminus of the Fc region of a human IgG1 antibody. Another useful Fc polypeptide is the Fc mutein described in U.S. Pat. No. 5,457,035 and in Baum et al., (*EMBO J.* 13:3992-4001, 1994) incorporated herein by reference. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors.

The above-described fusion proteins comprising Fc moieties (and oligomers formed therefrom) offer the advantage of facile purification by affinity chromatography over Protein A or Protein G columns.

In other embodiments, the polypeptides of the invention may be substituted for the variable portion of an antibody heavy or light chain. If fusion proteins are made with both heavy and light chains of an antibody, it is possible, for example, to form an oligomer with as many as four HAM extracellular regions.

Another method for preparing the oligomers of the invention involves use of a leucine zipper. Leucine zipper domains are peptides that promote oligomerization of the proteins in which they are found. Leucine zippers were originally identified in several DNA-binding proteins (Landschulz et al., *Science* 240:1759, 1988), and have since been found in a variety of different proteins. Among the known leucine zippers are naturally occurring peptides and derivatives thereof that dimerize or trimerize.

The zipper domain (also referred to herein as an oligomerizing, or oligomer-forming, domain) comprises a repetitive heptad repeat, often with four or five leucine residues interspersed with other amino acids. Examples of zipper domains are those found in the yeast transcription factor GCN4 and a heat-stable DNA-binding protein found in rat liver (C/EBP; Landschulz et al., *Science* 243:1681, 1989). Two nuclear transforming proteins, fos and jun, also exhibit zipper domains, as does the gene product of the murine proto-oncogene, c-myc (Landschulz et al., *Science* 240:1759, 1988). The products of the nuclear oncogenes fos and jun comprise zipper domains that preferentially form heterodimer (O'Shea et al., *Science* 245:646, 1989, Turner and Tjian, *Science* 243: 1689, 1989).

The fusogenic proteins of several different viruses, including paramyxovirus, coronavirus, measles virus and many retroviruses, also possess zipper domains (Buckland and Wild, *Nature* 338:547, 1989; Britton, *Nature* 353:394, 1991; Delwart and Mosialos, *AIDS Research and Human Retroviruses* 6:703, 1990). The zipper domains in these fusogenic viral proteins are near the transmembrane region of the proteins; it has been suggested that the zipper domains could contribute to the oligomeric structure of the fusogenic proteins. Oligomerization of fusogenic viral proteins is involved in fusion pore formation (Spruce et al., *Proc. Natl. Acad. Sci. U.S.A.* 88:3523, 1991). Zipper domains have also been reported to play a role in oligomerization of heat-shock transcription factors (Rabindran et al., *Science* 259:230, 1993).

Zipper domains fold as short, parallel coiled coils (O'Shea et al., *Science* 254:539, 1991). The general architecture of the parallel coiled coil has been characterized, with a "knobs-into-holes" packing as proposed by Crick in 1953 (*Acta Crystallogr.* 6:689). The dimer formed by a zipper domain is stabilized by the heptad repeat, designated (abcdefg)$_n$ according to the notation of McLachlan and Stewart (*J. Mol. Biol.* 98:293; 1975), in which residues a and d are generally hydrophobic residues, with d being a leucine, which line up on the same face of a helix. Oppositely-charged residues commonly occur at positions g and e. Thus, in a parallel coiled coil formed from two helical zipper domains, the "knobs" formed by the hydrophobic side chains of the first helix are packed into the "holes" formed between the side chains of the second helix.

The residues at position d (often leucine) contribute large hydrophobic stabilization energies, and are important for oligomer formation (Krystek: et al., *Int. J. Peptide Res.* 38:229, 1991). Lovejoy et al. (*Science* 259:1288, 1993) reported the synthesis of a triple-stranded α-helical bundle in which the helices run up-up-down. Their studies confirmed that hydrophobic stabilization energy provides the main driving force for the formation of coiled coils from helical monomers. These studies also indicate that electrostatic interactions contribute to the stoichiometry and geometry of coiled coils. Additional discussion of the structure of leucine zippers is found in Harbury et al. (*Science* 262:1401, 26 Nov. 1993).

Examples of leucine zipper domains suitable for producing soluble oligomeric proteins include the leucine zipper described in PCT application WO 94/10308 and the leucine zipper derived from lung surfactant protein D (SPD) described in Hoppe et al. (*FEBS Letters* 344:191, 1994), hereby incorporated by reference. The use of a modified leucine zipper that allows for stable trimerization of a heterologous protein fused thereto is described in Fanslow et al. (*Semin. Immunol.* 6:267-278, 1994). Recombinant fusion proteins comprising a bioactive fragment of the invention (e.g., a soluble fragment) fused to a leucine zipper peptide are expressed in suitable host cells, and the soluble oligomer that forms is recovered from the culture supernatant.

Certain leucine zipper moieties form trimers. One example is a leucine zipper derived from lung surfactant protein D (SPD) noted above, as described in Hoppe et al. and in U.S. Pat. No. 5,716,805, hereby incorporated by reference in their entirety. This lung SPD-derived leucine zipper peptide comprises the amino acid sequence: Pro-Asp-Val-Ala-Ser-Leu-Arg-Gln-Gln-Val-Glu-Ala-Leu-Gln-Gly-Gln-Val-Gln-His-Leu-Gln-Ala-Ala-Phe-Ser-Gln-Tyr (SEQ ID NO:11).

Another example of a leucine zipper that promotes trimerization is a peptide comprising the amino acid sequence Arg-Met-Lys-Gln-Ile-Glu-Asp-Lys-Ile-Glu-Glu-Ile-Leu-Ser-Lys-Ile-Tyr-His-Ile-Glu-Asn-Glu-Ile-Ala-Arg-Ile-Lys-Lys-Leu-Ile-Gly-Glu-Arg (SEQ ID NO:12), as described in U.S. Pat. No. 5,716,805. In one alternative embodiment, an N-terminal Asp residue is added; in another, the peptide lacks the N-terminal Arg residue.

Fragments of the foregoing zipper peptides that retain the property of promoting oligomerization may be employed as well. Examples of such fragments include, but are not limited to, peptides lacking one or two of the N-terminal or C-terminal residues presented in the foregoing amino acid sequences. Leucine zippers may be derived from naturally occurring leucine zipper peptides, e.g., via conservative substitution(s) in the native amino acid sequence, wherein the peptide's ability to promote oligomerization is retained. In particular embodiments, leucine residues in a leucine zipper moiety are replaced by isoleucine residues. Such peptides comprising isoleucine may be referred to as isoleucine zippers, but are encompassed by the term "leucine zippers" as employed herein.

Antibodies

The polypeptides, fragments (e.g., soluble or bioactive fragments), variants, fusion proteins, and the like, as set forth above may be employed as "immunogens" in producing antibodies immunoreactive therewith. More specifically, the polypeptides, fragment, variants, fusion proteins, and the like, contain antigenic determinants or epitopes that elicit the formation of antibodies. Suitable antigenic determinants or epitopes may be either linear or conformational (discontinuous). Linear epitopes are composed of a linear series of amino acids linked to one another by covalent bonds, while conformational or discontinuous epitopes are composed of amino acids sections from different regions of the polypeptide chain that are brought into close proximity upon protein folding (C. A. Janeway, Jr. and P. Travers, *Immuno Biology* 3:9 (Garland Publishing Inc., 2nd ed. 1996)). Because folded proteins have complex surfaces, the number of epitopes available is quite numerous; however, due to the conformation of the protein and steric hindrances, the number of antibodies that actually bind to the epitopes is less than the number of available epitopes (C. A. Janeway, Jr. and P. Travers, *Immuno Biology* 2:14 (Garland Publishing Inc., 2nd ed. 1996)). Epitopes may be identified by any number of methods known in the art.

The epitopes derived from the disclosed polypeptides are useful for raising antibodies, including monoclonal antibodies, and can be used as research reagents, in assays, and to purify specific binding antibodies from substances such as polyclonal sera or supernatants from cultured hybridomas. Such epitopes or variants thereof can be produced using techniques well known in the art such as solid-phase synthesis, chemical or enzymatic cleavage of a polypeptide, or using recombinant DNA technology.

The polyclonal and monoclonal antibodies elicited by the disclosed polypeptides, whether the epitopes have been isolated or remain part of the polypeptides, may be prepared by conventional techniques. See, for example, *Monoclonal Antibodies, Hybridomas: A New Dimension in Biological Analy-* ses, Kennet et al. (eds.), Plenum Press, New York (1980); and *Antibodies: A Laboratory Manual*, Harlow and Land (eds.), Cold Spring Harbor Laboratory Press, Cold Spring Harbor, N.Y., (1988).

Hybridoma cell lines that produce monoclonal antibodies specific for the polypeptides of the invention are also contemplated herein, and may be produced and identified by conventional techniques. One method for producing such a hybridoma cell line comprises immunizing an animal with a polypeptide; harvesting spleen cells from the immunized animal; fusing said spleen cells to a myeloma cell line, thereby generating hybridoma cells; and identifying a hybridoma cell line that produces a monoclonal antibody that binds the polypeptide. The monoclonal antibodies may be recovered by conventional techniques.

The monoclonal antibodies of the present invention include chimeric antibodies, e.g., humanized versions of murine monoclonal antibodies. Such humanized antibodies may be prepared by known techniques and offer the advantage of reduced immunogenicity when the antibodies are administered to humans, such as for therapeutic purposes. In one embodiment, a humanized monoclonal antibody comprises the variable region of a murine antibody (or just the antigen-binding site thereof) and a constant region derived from a human antibody. Alternatively, a humanized antibody fragment may comprise the antigen-binding site of a murine monoclonal antibody and a variable region fragment (lacking the antigen-binding site) derived from a human antibody. Procedures for the production of chimeric and further engineered monoclonal antibodies include those described in Riechmann et al. (*Nature* 332:323, 1988), Liu et al. (*PNAS* 84:3439, 1987), Larrick et al. (*Bio/Technology* 7:934, 1989), and Winter and Harris (*TIPS* 14:139, May, 1993). Procedures to generate antibodies transgenically can be found in GB 2,272,440, U.S. Pat. Nos. 5,569,825 and 5,545,806 and related patents claiming priority therefrom, all of which are incorporated by reference herein. Procedures to generate antibodies transgenically can be found in GB 2,272,440, U.S. Pat. Nos. 5,569,825 and 5,545,806 and related patents claiming priority therefrom, all of which are incorporated by reference herein. Preferably, for use in humans, the antibodies are human; techniques for creating such human antibodies are also known and transgenic mice useful for creating such antibodies are commercially available from, for example, Medarex Inc. (Princeton, N.J.) and Abgenix Inc. (Fremont, Calif.).

Antigen-binding fragments of the antibodies, which may be produced by conventional techniques, are also encompassed by the present invention. Examples of such fragments include, but are not limited to, scFv, Fab and $F(ab')_2$ fragments. Antibody fragments and derivatives produced by genetic engineering techniques are also provided.

The antibodies of the invention can be used in assays to detect the presence of the polypeptides or fragments of the invention, either in vitro or in vivo. The antibodies also may be employed in purifying polypeptides or fragments of the invention by immunoaffinity chromatography.

Those antibodies that block binding of the polypeptides of the invention to their binding partners may be used to inhibit a biological activity that results from such binding. Such blocking antibodies may be identified using any suitable assay procedure, such as by testing antibodies for the ability to inhibit binding of a HAM polypeptide or bioactive fragment thereof to certain cells expressing the binding partners of such polypeptide or fragment. Alternatively, blocking antibodies may be identified in assays for the ability to inhibit a biological effect that results from binding of the polypeptides of the invention to target cells. Antibodies may be assayed for the ability to inhibit HAM polypeptide-mediated cellular activities, for example.

Such antibodies may be employed in in vitro procedures, or administered in vivo to inhibit a biological activity mediated by the polypeptide to which the antibody binds. Disorders caused or exacerbated (directly or indirectly) by the interaction of the polypeptides of the invention with cell surface (binding partner) receptor thus may be treated. A therapeutic method involves in vivo administration of a blocking antibody to a mammal in an amount effective in inhibiting a HAM polypeptide-mediated biological activity. Monoclonal antibodies are generally preferred for use in such therapeutic methods. In one embodiment, an antigen-binding antibody fragment is employed. In addition, therapeutics of diagnostic labels may be conjugated to the antibodies of the invention thereby targeting the therapeutic or diagnostic to cells expressing a HAM polypeptide.

Antibodies may be screened for agonistic (i.e., HAM-mimicking) properties. An agonistic antibody includes antibodies that bind to HAM and activate HAM (e.g., by cross-linking the HAM molecule). Such antibodies, upon binding to HAM cognate on a cell surface, induce biological effects (e.g., transduction of biological signals) similar to the biological effects induced when a HAM polypeptide binds to cell surface ligands.

Compositions comprising an antibody that is directed against a HAM polypeptide or fragment thereof and a physiologically acceptable diluent, excipient, or carrier, are provided herein. Suitable components of such compositions are as described here and are similar to those described for compositions containing a HAM polypeptide or fragment thereof. Also provided herein are conjugates comprising a detectable (e.g., diagnostic) or therapeutic agent, attached to the antibody. The conjugates find use in in vitro or in vivo procedures.

Polynucleotides

The invention also provides polynucleotides encoding HAM polypeptides and bioactive fragments thereof. The term "polynucleotide" refers to a polymeric form of nucleotides of at least 10 bases in length. The nucleotides can be ribonucleotides, deoxyribonucleotides, or modified forms of either type of nucleotide. The term includes single and double stranded forms of DNA or RNA. DNA includes, for example, cDNA, genomic DNA (e.g., a sequence containing introns and exons), chemically synthesized DNA, DNA amplified by PCR, and combinations thereof. The polynucleotides of the invention include full-length genes and cDNA molecules as well as a combination of fragments thereof. The polynucleotides of the invention are preferentially derived from human sources, but the invention includes those derived from non-human species, as well.

By "isolated polynucleotide" is meant a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant polynucleotide molecule, which is incorporated into a vector, e.g., an expression vector; into an autonomously replicating plasmid or virus; or into the genomic DNA of a prokaryote or eukaryote, or which exists as a separate molecule (e.g., a cDNA) independent of other sequences.

A polynucleotide of the invention comprises (1) a sequence as set forth in SEQ ID NO:1 or 18; (2) sequences complementary to a sequence as set forth in SEQ ID NO:1 or 18; (3) fragments of SEQ ID NO:1 or 18 or their complements that specifically hybridize to the polynucleotide of (1) or (2) under moderate to highly stringent conditions, wherein the fragments are about 50 to 100 consecutive bases in length, 200 to 300 consecutive bases in length, or 500 to 1000 consecutive bases in length or longer; and (4) sequences of (1), (2), or (3) wherein T can also be U (e.g., RNA sequences). Also encompassed by the invention are homologues of a polynucleotide of the invention. These homologues can be identified in several ways, including isolation of genomic or cDNA molecules from a suitable source, or computer searches of available sequence databases. Oligonucleotides or polynucleotides corresponding to the amino acid sequences described herein can be used as probes or primers for the isolation of polynucleotide homologues or as query sequences for database searches. Degenerate oligonucleotide sequences can be obtained by "back-translation" from the amino acid sequences (e.g., a sequence of SEQ ID NO:2 or 19). The polymerase chain reaction (PCR) procedure can be employed to isolate and amplify a polynucleotide encoding a HAM polypeptide. Fragments of the polynucleotides of the invention are useful as probes and primers to identify or amplify related sequence or obtain full-length sequences of a HAM polynucleotide of the invention. The oligonucleotides can additionally contain recognition sites for restriction endonucleases, to facilitate insertion of the amplified combination of DNA fragments into an expression vector. PCR techniques are described in Saiki et al., Science 239:487 (1988); Recombinant DNA Methodology, Wu et al., eds., Academic Press, Inc., San Diego (1989), pp. 189-196; and PCR Protocols: A Guide to Methods and Applications, Innis et. al., eds., Academic Press, Inc. (1990).

The invention also includes polynucleotides and oligonucleotides that hybridize under reduced stringency conditions, more preferably moderately stringent conditions, and most preferably highly stringent conditions, to polynucleotides encoding HAM polypeptides described herein. The basic parameters affecting the choice of hybridization conditions and guidance for devising suitable conditions are set forth by Sambrook, J., E. F. Fritsch, and T. Maniatis (1989, Molecular Cloning: A Laboratory Manual, Cold Spring Harbor Laboratory Press, Cold Spring Harbor, N.Y., chapters 9 and 11; and Current Protocols in Molecular Biology, 1995, F. M. Ausubel et al., eds., John Wiley & Sons, Inc., sections 2.10 and 6.3-6.4, incorporated herein by reference), and can be readily determined by those having ordinary skill in the art based on, for example, the length and/or base composition of the nucleic acid. One way of achieving moderately stringent conditions involves the use of a prewashing solution containing 5×SSC, 0.5% SDS, 1.0 mM EDTA (pH 8.0), hybridization buffer of about 50% formamide, 6×SSC, and a hybridization temperature of about 55° C. (or other similar hybridization solutions, such as one containing about 50% formamide, with a hybridization temperature of about 42° C.), and washing conditions of about 60° C., in 0.5×SSC, 0.1% SDS. Generally, highly stringent conditions are defined as hybridization conditions as above, but with washing at approximately 68° C., 0.2×SSC, 0.1% SDS. SSPE (1×SSPE is 0.15M NaCl, 10 mM NaH$_2$PO$_4$, and 1.25 mM EDTA, pH 7.4) can be substituted for SSC (1×SSC is 0.15M NaCl and 15 mM sodium citrate) in the hybridization and wash buffers; washes are performed for 15 minutes after hybridization is complete. It should be understood that the wash temperature and wash salt concentration can be adjusted as necessary to achieve a desired degree of stringency by applying the basic principles that govern hybridization reactions and duplex stability, as known to those skilled in the art and described further below (see, e.g., Sambrook et al., 1989). When hybridizing a nucleic acid to a target polynucleotide of unknown sequence, the hybrid length is assumed to be that of the hybridizing nucleic acid. When nucleic acids of known sequence are hybridized, the hybrid length can be determined by aligning the sequences of the nucleic acids and identifying the region or regions of optimal sequence complementarity. The hybridization temperature for hybrids anticipated to be less than 50 base pairs in length should be 5 to 10° C. less than the melting temperature ($T_m$) of the hybrid, where $T_m$ is determined according to the following equations. For hybrids less than 18 base pairs in length, $T_m$ (° C.)=2(# of A+T bases)+4(# of G+C bases). For hybrids above 18 base pairs in length, $T_m$ (° C.)=81.5+16.6(log 10 [Na$^+$])+0.41(% G+C)−(600/N), where N is the number of bases in the hybrid, and [Na$^+$] is the concentration of sodium ions in the hybridization buffer ([Na$^+$] for 1×SSC=0.165M). Preferably, each such hybridizing nucleic acid has a length that is at least 25% (more preferably at least 50%, or at least 60%, or at least 70%, and most preferably at least 80%) of the length of the nucleic acid of the invention to which it hybridizes, and has at least 60% sequence identity (more preferably at least 70%, at least 75%, at least 80%, at least 85%, at least 90%, at least 95%, at least 97.5%, or at least 99%, and most preferably at least 99.5%) with the polynucleotide of the invention to which it hybridizes.

Other embodiments of the invention include polynucleotides having sequences that encode discrete domains of a HAM polypeptide having a sequence as set forth in SEQ ID NO:2 or 19. Computer analysis predicts that the signal peptide of the HAM polypeptides is most likely to be cleaved after residue 60 of SEQ ID NO:2 and after residue 59 of SEQ ID NO:19, though other possible cleavage sites include after amino acids 54, 55, 59, 172, or 173. These cleavage sites predict a mature HAM polypeptide comprising from about amino acid 55 to 1379, from about 56 to 1379, from about 60 to 1379, from about 61 to 1379, or from about 174 to 1379 of SEQ ID NO:2, and from about 55 to 1378, from about 56 to 1378, from about 60 to 1378, from about 61 to 1378, or from about 173 to 1378 of SEQ ID NO:19. The EGF-like domains located, for example, at about amino acids 63-90, 211-243, and 261-280 of SEQ ID NO:2 are likely to be involved in extracellular signaling or cellular guidance. A CUB domain, a KELCH motif, a C-type Lectin or carbohydrate-recognition domain, a putative ligand binding motif of the common gamma cytokine chain, and a Laminin EGF-like domain located at about amino acids 93-208, 581-612, 749-873, 670-686, and 1014-1055 of SEQ ID NO:2, respectively (see FIG. 3). A transmembrane region is present at about amino acids 1231 to 1251, and a cytoplasmic domain at about amino acids 1252 to 1379 of SEQ ID NO:2. Thus, the invention provides polynucleotides encoding these discrete polypeptide fragments, as well as the polypeptide fragments comprising each domain separately or in various combinations. The invention provides polynucleotides comprising from about nucleotide 1-162, from about 1-165, from about 1-177, from about 1-180, or from about 1-522 of SEQ ID NO:1, which encode the signal peptides residing at about amino acids 1-54, 1-55, 1-59, 1-60, or 1-173 of SEQ ID NO:2; from about nucleotides 163-4137, from about 166-4137, from about 178-4137, from about 1814137, or from about 5234137 of SEQ ID NO:1, which encode mature HAM polypeptides comprising, respectively, amino acids 55-1379, 56-1379, 60-1379, 61-1379, or 174-1379 of SEQ ID NO:2; nucleotides 3691-3753 of SEQ ID NO:1, encoding a transmembrane region comprising amino acids 1231-1251 of SEQ ID NO:2; nucleotides 163-3690, 166-3690, 178-3690, 181-3690, or 523-3690 of SEQ ID NO:1, encoding extracellular domains of the HAM polypeptide comprising amino acids 55-1230, 56-1230, 60-1230, 61-1230, or 174-1230, respectively, of SEQ ID NO:2; and nucleotides 3754-4137 of SEQ ID NO:1, encoding a cytoplasmic domain comprising amino acids 1252-1379 of SEQ ID NO:2.

In addition, the invention provides polynucleotides comprising from about nucleotides 1-177 of SEQ ID NO:18, which encode the signal peptide residing at about amino acids 1-59 of SEQ ID NO:19; from about nucleotides 178-4134 of SEQ ID NO:18, which encodes a mature murine HAM polypeptide comprising amino acids 60-1378 of SEQ ID NO:19; and from about nucleotides 178-3687 of SEQ ID NO:18, encoding an extracellular domain of a murine HAM polypeptide comprising amino acids 60-1229 of SEQ ID NO:19.

Polynucleotides of the invention may be used in developing treatments for any disorder mediated (directly or indirectly) by defective, or insufficient amounts of, the genes corresponding to the polynucleotides of the invention. Disclosure herein of sequences corresponding to the polynucleotides of the invention permits the detection of defective genes, and the replacement thereof with normal genes. Defective genes may be detected in in vitro diagnostic assays, and by comparison of the polynucleotide sequences disclosed herein with that of a gene derived from a subject suspected of harboring a defect in the genes.

Expression, isolation and purification of the polypeptides and fragments of the invention may be accomplished by any suitable technique, including the utilization of expression systems such as those known in the art as well as those described herein. In one embodiment, the invention provides an expression vector comprising a polynucleotide encoding a HAM polypeptide of the invention. The polynucleotide of the invention (e.g., a polynucleotide comprising a sequence as set forth in SEQ ID NO:1 or 18) may be operably inserted into, for example, a commercially available expression vector by recombinant techniques known in the art. Typically the polynucleotide will be inserted downstream (or 3') of and operably linked to a control or regulatory sequence. As used herein, a "control sequence" or "regulatory sequence" are used interchangeably to include a promoter, enhancer-promoter combination, or other sequence that effects the expression or transcription of the downstream polynucleotide sequence. A promoter is a transcriptional regulatory element composed of a region of a DNA molecule typically within 100 nucleotide pairs in front of (upstream of) the point at which transcription starts. Another transcriptional regulatory element is an enhancer, which provides specificity in terms of time, location, and expression level. Unlike a promoter, an enhancer can function when located at variable distances from the transcription site, provided a promoter is present. An enhancer can also be located downstream of the transcription initiation site. Other regulatory sequences include transcription termination sequence, internal ribosome entry sites (IRES), and the like.

Typically, to bring a coding sequence under control of a promoter, it is necessary to position the translation initiation site of the translational reading frame of the peptide or polypeptide between one and about fifty nucleotides downstream (3') of the promoter. Such regulatory elements include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors, to name a few.

Expression vectors and methods for their construction are known to those skilled in the art (Ausubel et al., cited herein). Suitable vectors include plasmids, and viral vectors such as herpes viruses, retroviruses, canary poxviruses, adenoviruses and adeno-associated viruses, among others, and derivatives thereof.

A polynucleotide and regulatory sequences are "operably linked" when they are connected in such a way as to permit expression when the coding sequence (e.g., the HAM coding sequence) of the polynucleotide is bound to the regulatory sequences, e.g., within an expression vector. An origin of replication that confers the ability to replicate in the desired host cells, and a selection gene (e.g., kan$^r$, amp$^r$) by which transformants are identified, are generally incorporated into the expression vector.

Expression vectors comprising a polynucleotide of the invention may be used to prepare the polypeptides or fragments of the invention encoded by the polynucleotide. A method for producing polypeptides comprises culturing host cells transformed or transfected with a recombinant expression vector encoding the polypeptide, under conditions that promote expression of the polypeptide, then recovering the expressed polypeptides from the cells or from culture medium in which the host cell is grown. The procedure for purifying the expressed polypeptides will vary according to the type of host cells employed, and whether the polypeptide is membrane-bound or is a secreted soluble form of the polypeptide.

In addition, a sequence encoding an appropriate signal peptide (native or heterologous) can be incorporated into expression vectors. A DNA sequence for a signal peptide may be fused in frame to a polynucleotide sequence of the invention so that the polynucleotide is initially transcribed, and the mRNA translated, into a fusion protein comprising the signal peptide. Signal peptides may be employed that direct transmembrane proteins to the cell surface or different signal peptides may be used that promote the secretion of a soluble form of the protein. Generally, the signal peptide is cleaved during maturation of the protein. A polynucleotide encoding a localization sequence, or signal sequence, can be ligated or fused at the 5' terminus of a polynucleotide encoding a HAM polypeptide such that the signal peptide is located at the amino terminal end of the resulting fusion polynucleotide/polypeptide. In eukaryotes, the signal peptide functions to transport the fusion polypeptide across the endoplasmic reticulum. The secretory protein is then transported through the Golgi apparatus, into secretory vesicles and into the extracellular space or, preferably, the external environment. Signal peptides, which can be utilized according to the invention, include pre-pro peptides, which contain a proteolytic enzyme recognition site.

The localization sequence can be a nuclear localization sequence, an endoplasmic reticulum localization sequence, a peroxisome localization sequence, a mitochondrial localization sequence, or a localized protein. Localization sequences can be targeting sequences that are described, for example, in "Protein Targeting", chapter 35 of Stryer, L., Biochemistry (4th ed.). W. H. Freeman, 1995. Some important localization sequences include those targeting the nucleus (e.g., KKKRK (SEQ ID NO:13)), mitochondrion (MLRTSSLFTR-RVQPSLFRNILRLQST (SEQ ID NO:14)), endoplasmic reticulum (KDEL (SEQ ID NO:15)), peroxisome (SKF), prenylation or insertion into plasma membrane (CAAX (SEQ ID NO:16), CC, CXC, or CCXX (SEQ ID NO:17)), cytoplasmic side of plasma membrane (fusion to SNAP-25), or the Golgi apparatus (fusion to furin). Other examples of heterologous signal peptides that are functional in mammalian host cells include the signal sequence for interleukin-7 (IL-7) described in U.S. Pat. No. 4,965,195; the signal sequence for interleukin-2 receptor described in Cosman et al., Nature 312:768 (1984); the interleukin-4 receptor signal peptide described in EP 367,566; the type I interleukin-1 receptor signal peptide described in U.S. Pat. No. 4,968,607; and the type II interleukin-1 receptor signal peptide described in EP 460,846.

The skilled artisan will also recognize that the position(s) at which the signal peptide is cleaved may differ from that predicted by computer program, and may vary according to such factors as the type of host cells employed in expressing a recombinant polypeptide. A protein preparation may include a mixture of protein molecules having different N-terminal amino acids, resulting from cleavage of the signal peptide at more than one site. Particular embodiments of mature HAM polypeptides provided herein having a native signal sequence include, but are not limited to, polypeptides wherein the N-terminus amino acid is any amino acid between 55 and 61 of SEQ ID NO:2.

Suitable host cells for expression of polypeptides include prokaryotes (e.g., *E. coli*), yeast, plant cells, and insect or higher eukaryotic cells. Most typically, yeast or mammalian cells are used. Appropriate cloning and expression vectors for use with bacterial, fungal, yeast, and mammalian cellular hosts are described, for example, in Pouwels et al. Cloning Vectors: A Laboratory Manual, Elsevier, New York, (1985). Cell-free translation systems could also be employed to produce polypeptides using RNAs derived from DNA constructs disclosed herein.

Suitable prokaryotic host cells for transformation may be gram-negative or gram-positive, and include, for example, *E. coli, Bacillus subtilis, Salmonella typhimurium*, and various other species within the genera *Pseudomonas, Streptomyces*, and *Staphylococcus*. In a prokaryotic host cell, such as *E. coli*, a polypeptide may include an N-terminal methionine (met) residue to facilitate expression of the recombinant polypeptide in the prokaryotic host cell. The N-terminal Met may be cleaved from the expressed recombinant polypeptide.

Expression vectors for use in prokaryotic host cells generally comprise one or more phenotypic selectable marker genes, which may include, for example, a gene encoding a protein that confers antibiotic resistance or that supplies an autotrophic requirement. Useful prokaryotic expression vectors include those derived from commercially available plasmids such as the cloning vector pBR322 (ATCC 37017), with ampicillin and tetracycline resistance genes. Other suitable vectors include, pKK223-3 (Pharmacia Fine Chemicals, Uppsala, Sweden) and pGEM1 (Promega Biotec, Madison, Wis., USA). An appropriate promoter and a polynucleotide sequence encoding the desired polypeptide may be inserted into the vector.

Promoter sequences commonly used for recombinant prokaryotic host cell expression vectors include β-lactamase (penicillinase), lactose promoter system (Chang et al., Nature 275:615, 1978; and Goeddel et al., Nature 281:544, 1979), tryptophan (trp) promoter system (Goeddel et al., Nucl. Acids Res. 8:4057, 1980) and tac promoter (Maniatis et al., Molecular Cloning: A Laboratory Manual, first ed., Cold Spring Harbor Laboratory, p. 412, 1982). A particularly useful prokaryotic host cell expression system employs a phage λPL promoter and a cI857ts thermolabile repressor sequence. Plasmid vectors available from the American Type Culture Collection which incorporate derivatives of the λPL promoter include plasmid pHUB2 (resident in *E. coli* strain JMB9, ATCC 37092) and pPLc28 (resident in *E. coli* RR1, ATCC 53082).

Alternatively, the polypeptides may be expressed in yeast host cells, such as from the *Saccharomyces* genus (e.g., *S. cerevisiae*). Alternatively, *Pichia, Kluyveromyces*, or other yeast genera may be employed. Yeast vectors will often contain an origin of replication sequence from a 2mu yeast plasmid, an autonomously replicating sequence (ARS), a promoter region, sequences for polyadenylation, sequences for transcription termination, and a selectable marker gene. Suitable promoter sequences include those derived from the yeast metallothionein or 3-phosphoglycerate kinase genes (Hitzeman et al., J. Biol. Chem. 255:2073, 1980) or other genes encoding glycolytic enzymes (Hess et al., J. Adv. Enzyme Reg. 7:149, 1968; and Holland et al., Biochem. 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phospho-glucose isomerase, and glucokinase. Other suitable vectors and promoters for use in yeast expression are known in the art (e.g., see in Hitzeman, EPA-73,657; Russell et al., J. Biol. Chem. 258:2674, 1982; and Beier et al., Nature 300:724, 1982).

The yeast α-factor leader sequence may be employed to direct secretion of the polypeptide, and often is inserted between the promoter sequence and the structural gene sequence (e.g., Kurjan et al., Cell 30:933, 1982 and Bitter et al., Proc. Natl. Acad. Sci. USA 81:5330, 1984).

Yeast transformation protocols are known to those of skill in the art, including a protocol involving selection for Trp⁺ transformants in a medium containing yeast nitrogen base, casamino acids, glucose, 10 mg/ml adenine and 20 mg/ml uracil (see, e.g., Hinnen et al., Proc. Natl. Acad. Sci. USA 75:1929, 1978). In other protocols, yeast cells transformed by vectors containing an ADH2 promoter sequence may be grown in a "rich" medium. An example of a rich medium is one consisting of 1% yeast extract, 2% peptone, and 1% glucose supplemented with 80 mg/ml adenine and 80 mg/ml uracil. Derepression of the ADH2 promoter occurs when glucose is exhausted from the medium.

Mammalian or insect host cell culture systems also may be employed to express recombinant polypeptides, such as the baculovirus systems reviewed by Luckow and Summers, Bio/Technology 6:47 (1988). Established cell lines of mammalian origin also may be employed. Examples of suitable mammalian host cell lines include the COS-7 line of monkey kidney cells (ATCC CRL 1651) (Gluzman et al., Cell 23:175, 1981), L cells, C127 cells, 3T3 cells (ATCC CCL 163), Chinese hamster ovary (CHO) cells, HeLa cells, and BHK (ATCC CRL 10) cell lines, and the CV1/EBNA cell line derived from the African green monkey kidney cell line CV1 (ATCC CCL 70) as described by McMahan et al. (EMBO J. 10: 2821, 1991).

Established methods for introducing polynucleotides into mammalian cells have been described (Kaufman, R. J., Large Scale Mammalian Cell Culture, 1990, pp. 15-69). Additional protocols using commercially available reagents, such as Lipofectamine lipid reagent (Gibco/BRL) or Lipofectamine-Plus lipid reagent, can be used to transfect cells (Felgner et al., Proc. Natl. Acad. Sci. USA 84:7413-7417, 1987). In addition, electroporation can be used to transfect mammalian cells using conventional procedures, such as those in Sambrook et al., 1989. Selection of stable transformants can be performed using methods known in the art, such as, for example, resistance to cytotoxic drugs. Kaufman et al., Meth. in Enzymology 185:487-511, 1990, describes several selection schemes, such as dihydrofolate reductase (DHFR) resistance. A suitable host strain for DHFR selection is CHO strain DX-B11, which is deficient in DHFR (Urlaub and Chasin, Proc. Natl.

Acad. Sci. USA 77:4216-4220, 1980). A plasmid expressing the DHFR cDNA can be introduced into strain DX-B11, and only cells that contain the plasmid can grow in the appropriate selective media. Other examples of selectable markers include genes conferring resistance to antibiotics, such as G418 and hygromycin B, which permit selection of cells harboring the vector on the basis of resistance to these agents.

Transcriptional and translational control sequences for mammalian host cell expression vectors can be excised from viral genomes. Commonly used promoter sequences and enhancer sequences are derived from polyoma virus, adenovirus 2, simian virus 40 (SV40), and human cytomegalovirus. Polynucleotide sequences derived from the SV40 viral genome, for example, SV40 origin, early and late promoter, enhancer, splice, and polyadenylation sites can be used to provide other genetic elements for expression of a structural gene sequence in a mammalian host cell. Viral early and late promoters are particularly useful because both are easily obtained from a viral genome as a fragment, which can also contain a viral origin of replication (Fiers et al., Nature 273: 113, 1978; Kaufman, Meth. in Enzymology, 1990). Smaller or larger SV40 fragments can also be used, provided the approximately 250 bp sequence extending from the Hind III site toward the Bgl I site located in the SV40 viral origin of replication site is included.

Additional control sequences shown to improve expression of heterologous genes from mammalian expression vectors include such elements as the expression augmenting sequence element (EASE) derived from CHO cells (Morris et al., Animal Cell Technology, 1997, pp. 529-534 and PCT Application WO 97/25420) and the tripartite leader (TPL) and VA gene RNAs from Adenovirus 2 (Gingeras et al., J. Biol. Chem. 257:13475-13491, 1982). The internal ribosome entry site (IRES) sequences of viral origin allows dicistronic mRNAs to be translated efficiently (Oh and Sarnow, Current Opinion in Genetics and Development 3:295-300, 1993; Ramesh et al., Nucleic Acids Research 24:2697-2700, 1996). Expression of a heterologous cDNA as part of a dicistronic mRNA followed by the gene for a selectable marker (e.g. DHFR) has been shown to improve transfectability of the host and expression of the heterologous polynucleotides (Kaufman, Meth. in Enzymology, 1990). Exemplary expression vectors that employ dicistronic mRNAs are pTR-DC/GFP described by Mosser et al., Biotechniques 22:150-161, 1997, and p2A5I described by Morris et al., Animal Cell Technology, 1997, pp. 529-534.

A useful high expression vector, pCAVNOT, has been described by Mosley et al., Cell 59:335-348, 1989. Other expression vectors for use in mammalian host cells can be constructed as disclosed by Okayama and Berg (Mol. Cell. Biol. 3:280, 1983). A useful system for stable high level expression of mammalian cDNAs in C127 murine mammary epithelial cells can be constructed substantially as described by Cosman et al. (Mol. Immunol. 23:935, 1986). A useful high expression vector, PMLSV N1/N4, described by Cosman et al., Nature 312:768, 1984, has been deposited as ATCC 39890. Additional useful mammalian expression vectors are described in EP-A-0367566, and in WO 91/18982, incorporated by reference herein. In yet another alternative, the vectors can be derived from retroviruses.

Additional useful expression vectors, pFLAG® and pDC311, can also be used. FLAG® technology is centered on the fusion of a low molecular weight (1 kD), hydrophilic, FLAG® marker peptide to the N-terminus of a recombinant protein expressed by pFLAG® expression vectors. pDC311 is another specialized vector used for expressing proteins in CHO cells. pDC311 is characterized by a bicistronic sequence containing the gene of interest and a dihydrofolate reductase (DHFR) gene with an internal ribosome binding site for DHFR translation, an expression augmenting sequence element (EASE), the human CMV promoter, a tripartite leader sequence, and a polyadenylation site.

Other useful fragments of the disclosed polynucleotides include antisense or sense oligonucleotides comprising a single-stranded polynucleotide sequence (either RNA or DNA) capable of binding to target mRNA (sense) or DNA (antisense) sequences. Antisense or sense oligonucleotides, according to the present invention, comprise fragments of the polynucleotide having a sequence as set forth in SEQ ID NO:1 or 18. Such a fragment generally comprises at least about 14 nucleotides, preferably from about 14 to about 30 nucleotides. The ability to derive an antisense or a sense oligonucleotide, based upon a nucleic acid sequence encoding a given protein is described in, for example, Stein and Cohen (Cancer Res. 48:2659, 1988) and van der Krol et al. (BioTechniques 6:958, 1988).

Binding of antisense or sense oligonucleotides to target nucleic acids results in the formation of duplexes that block or inhibit protein expression by one of several means, including enhanced degradation of the mRNA by RNAse H, inhibition of splicing, premature termination of transcription or translation, or by other means. The antisense oligonucleotides thus may be used to block expression of proteins. Antisense or sense oligonucleotides further comprise oligonucleotides having modified sugar-phosphodiester backbones (or other sugar linkages, such as those described in WO91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleic acids.

Other examples of sense or antisense oligonucleotides include those oligonucleotides which are covalently linked to organic moieties, such as those described in WO 90/10448, and other moieties that increases affinity of the oligonucleotide for a target nucleic acid, such as poly-(L)-lysine. Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid by any gene transfer method, including, for example, lipofection, $CaPO_4$-mediated DNA transfection, electroporation, or by using gene transfer vectors such as Epstein-Barr virus or adenovirus.

Sense or antisense oligonucleotides also may be introduced into a cell containing the target nucleic acid by formation of a conjugate with a ligand-binding molecule, as described in WO 91/04753. Suitable ligand binding molecules include, but are not limited to, cell surface receptors, growth factors, other cytokines, or other ligands that bind to cell surface receptors. Preferably, conjugation of the ligand-binding molecule does not substantially interfere with the ability of the ligand-binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid by formation of an oligonucleotide-lipid complex, as described in WO 90/10448. The sense or antisense oligonucleotide-lipid complex is preferably dissociated within the cell by an endogenous lipase.

The polynucleotides of the invention enable the construction of vectors (e.g., expression vectors) comprising a polynucleotide encoding a HAM polypeptide of the invention, or fragment thereof; host cells transfected or transformed with the vectors; methods of producing and purifying biologically active polypeptides and bioactive fragments thereof; the use of the polynucleotides or oligonucleotides thereof as probes to identify nucleic acids encoding related attractin or mahogany family proteins; the use of the polynucleotides or oligonucleotides thereof to correlate the location of genes encoding HAM polypeptides of the invention with chromosome regions associated with human diseases; the use of the polynucleotides or oligonucleotides thereof to identify genes associated with tumors, immune disorders, syndromes or other human conditions; the administration of the disclosed proteins or fragments thereof for the treatment of disorders characterized by a mutation in a gene encoding a HAM polypeptide or by an excess or a deficiency of a HAM polypeptide; and the use of single-stranded sense or antisense oligonucleotides to inhibit expression of polynucleotides encoding a HAM polypeptide. In addition, the invention provides the use of the disclosed polypeptides and soluble fragments thereof as competitive inhibitors of the binding of native HAM polypeptides to their ligands, cognates, or counter-structure binding partners; the use of HAM polypeptides and fragments thereof as unique molecular weight markers or as controls for peptide fragmentation as well as kits comprising these reagents; the use of HAM polypeptides and fragments thereof to generate antibodies; and the use of such antibodies to purify HAM polypeptides; as affinity reagents for the separation of hematopoietic cells expressing the proteins as well as the use of the antibodies in the modulation of HAM polypeptide biological activity. For treatment of humans, typically human HAM polypeptides, fragments and polynucleotides encoding the foregoing are used.

Activity Assays

The purified polypeptides of the invention (including proteins, polypeptides, fragments, variants, oligomers, and other forms) may be tested for the ability to bind a HAM binding partner. Such activities can be measured in any suitable assay, such as a conventional binding or enzymatic assay. To illustrate, in a typical binding assay the polypeptide may be labeled with a detectable reagent (e.g., a radionuclide, chromophore, enzyme that catalyzes a colorimetric or fluorometric reaction, and the like), and then contacted with cells expressing a HAM binding partner on its surface. The cells are washed to remove unbound-labeled polypeptide, and the presence of cell-bound label is determined by a suitable technique. For example, a recombinant expression vector is constructed containing a polynucleotide encoding a HAM polypeptide (or bioactive fragment thereof) fused to an Fc region according to methods well known in the art. Upon expression the polynucleotide encodes, for example, a soluble HAM polypeptide comprising the extracellular portions of the HAM polypeptide, or the extracellular domain and a cytoplasmic domain with the transmembrane region removed. For example, host cells are transfected with the recombinant expression vector comprising a polynucleotide of the invention. After culturing the transfected cells, culture medium containing a HAM or other soluble polypeptide of the invention is collected from the transfected cells and the amount of the polypeptide is quantified using standard methods.

Cells expressing the HAM binding partner are cultured and washed with BM-NFDM, which is binding medium (RPMI 1640 containing 25 mg/ml bovine serum albumin, 2 mg/ml sodium azide, 20 mM Hepes pH 7.2) to which 50 mg/ml nonfat dry milk has been added. The cells then are incubated with various concentrations of, for example, a soluble polypeptide/Fc fusion protein made as set forth above. Cells are washed and incubated with a constant saturating concentration of a $^{125}$I-mouse anti-human IgG in binding medium, with gentle agitation for 1 hour at 37° C. After extensive washing, cells are released via trypsinization.

The mouse anti-human IgG employed above is directed against the Fc region of human IgG and can be obtained from Jackson Immunoresearch Laboratories, Inc., West Grove, Pa. The antibody is radioiodinated using the standard chloramine-T method. The antibody will bind to the Fc portion of any polypeptide/Fc protein that has bound to the cells. In all assays, non-specific binding of $^{125}$I-antibody is assayed in the absence of the Fc fusion protein/Fc, as well as in the presence of the Fc fusion protein and a 200-fold molar excess of unlabeled mouse anti-human IgG antibody.

Cell-bound $^{125}$I-antibody is quantified on a Packard Auto-gamma counter. Affinity calculations (Scatchard, Ann. N.Y. Acad. Sci. 51:660, 1949) are generated on RS/1 (BBN Software, Boston, Mass.) run on a Microvax computer.

To illustrate, the substrate may be labeled with a detectable reagent (e.g., a radionuclide, chromophore, and the like), and then contacted with cells or a sample containing a HAM polypeptide or fragment thereof. The labeled-substrate is typically bound to a microtiter plate or the like. Following incubation of the two components the plate is washed and the amount of label still present on the plate is quantitated compared to a control plate. A reduction in label on the plate is indicative of enzymatic activity.

Another type of suitable binding assay is a competitive binding assay. To illustrate, biological activity of a variant may be determined by assaying for the variant's ability to compete with the native proteins for binding to its binding partner.

Competitive binding assays can be performed by conventional methodology. Reagents that may be employed in competitive binding assays include a radiolabeled soluble HAM polypeptide or intact cells expressing a HAM polypeptide (endogenous or recombinant) on the cell surface. For example, a radiolabeled bioactive fragment of a HAM polypeptide can be used to compete with a soluble variant for binding to a cell surface-binding partner. Instead of intact cells, one could substitute a bioactive fragment of a HAM polypeptide/Fc fusion protein bound to a solid phase through the interaction of Protein A or Protein G (on the solid phase) with the Fc moiety. Chromatography columns that contain Protein A and Protein G include those available from Pharmacia Biotech, Inc., Piscataway, N.J.

Another type of competitive binding assay utilizes a radiolabeled soluble bioactive fragment of a HAM polypeptide, such as a soluble bioactive fragment/Fc fusion protein, and intact cells expressing HAM binding partners. Qualitative results can be obtained by competitive autoradiographic plate binding assays, while Scatchard plots (Scatchard, Ann. N.Y. Acad. Sci. 51:660, 1949) may be utilized to generate quantitative results.

Diagnostic Assays

The polynucleotides and polypeptides provided herein are useful as diagnostic reagents in assays to detect malfunctioning or mutant HAM genes. Samples for diagnosis may be obtained from a subject's tissues, for example, throat swab, blood, serum, urine, saliva, cerebrospinal fluid, feces, tissue biopsy, and so on. Similar samples are taken from normal individuals (from persons not suffering from the disorder or mutation in question), and these normal or standard samples provide a basis for comparison. Alternatively, purified reagents (e.g., HAM polynucleotides, polypeptides, and antibodies) may be used as standards for the diagnostic assays. In some embodiments, fragments of the polynucleotides of the invention are used as probes for Northern or Southern blots or as PCR primers to detect mutated forms of a HAM polypeptide encoded by the target nucleic acid.

Conditions that may be diagnosed include those characterized by an excess or deficiency of a HAM polypeptide, or that are characterized by a mutated form of such a polypeptide. Such conditions include, but are not limited to, absence of the polypeptide in a cell that requires its expression, altered enzymatic activity, altered signalling ability, overexpression or underexpression in a cell that under normal conditions has such an activity.

Particular conditions that may be diagnosed using these assays include but are not limited to: rheumatologic diseases (e.g., rheumatoid arthritis, psoriatic arthritis, seronegative spondyloarthropathies), inflammatory conditions, bone marrow or solid organ transplantation, graft-versus-host disease, allergies (e.g., asthma, allergic rhinitis), neurologic disorders (e.g., Alzheimer's, Parkinson's, dementia, brain cancer, Bell's palsy, post-herpetic neuralgia), cell proliferative disorders including neoplasms or cancer (e.g., lymphoma, B-cell, T-cell and myeloid cell leukemias), infections (e.g., bacterial, parasitic, protozoal and viral infections, including AIDS), chemotherapy or radiation-induced toxicity, cachexia, cardiovascular disorders (e.g., congestive heart failure, myocardial infarction, ischemia/reperfusion injury, arteritis, stroke), gastrointestinal disorders (e.g., inflammatory bowel disease, Crohn's disease, celiac disease), diabetes mellitus, skin diseases (e.g., psoriasis, scleroderma, dermatomyositis), hematologic disorders (e.g., myelodysplastic syndromes, acquired or Fanconi's aplastic anemia), septic shock, liver diseases (e.g., viral hepatitis or alcohol-associated), bone disorders (e.g., osteoporosis, osteopetrosis).

In some embodiments of the invention, the condition being diagnosed is a hematologic disorder, and the tissue sample is blood or a lymph node biopsy.

Screening for Modulators of HAM Polypeptides and Polynucleotides

The HAM polypeptides and polynucleotides disclosed herein find use in screening assays for identifying agents that modulate the expression or activity of the polynucleotides and polypeptides of the invention, respectively. Once identified, agents that modulate expression or activity of a HAM polynucleotides and polypeptides may be administered, for example, to suppress HAM expression in conditions characterized by overproduction of HAM or other attractin/mahogany related proteins. Similarly, agents that stimulate the biological activity or expression of a HAM polypeptide in cultured cells or in subjects may be administered to stimulate activity or expression where a condition is characterized by a deficiency of the normal endogenous activator of HAM.

Methods to identify an agent that modulates the activity or expression of a HAM polypeptide can be carried out using the teachings provided herein. For example, to identify an agent that modulates HAM polypeptide activity a test agent is contacted with a sample containing a HAM polypeptide of the invention. The sample is then assayed to measure HAM activity and the HAM activity in the presence of the test agent is compared to the activity present in a standard (i.e., a control) sample that does not have the agent present. A sample can be, for example, a cell-free sample, a cell-containing sample (e.g., a cell culture), or a tissue sample (e.g., a tissue sample obtained or derived from a subject). A standard sample includes, for example, the sample prior to contact with the test agent or a sample that represents normal activity. Activity can be measured using any of the assay methods identified herein (e.g., competitive binding assays, enzymatic assays, and the like). A change in activity compared to a control or standard sample is indicative of an agent that modulates (e.g., increases or decreases) activity.

Similarly, the invention provides a method for identifying an agent that modulates expression of a HAM polypeptide. Such methods include, for example, contacting a sample comprising a polynucleotide of the invention with a test agent and measuring expression of the polynucleotide compared to a standard or control sample. The level of expression can be determined by methods know in the art, including detecting protein (e.g., by Western Blot), or by detecting the amount of mRNA transcribed (e.g., by PCR). As above, the sample can be a cellular sample, a tissue sample, and the like. A change in expression compared to a control or standard sample is indicative of an agent that modulates (e.g., increases or decreases) expression.

A test agent can include, for example, a protein, a peptide, a peptidomimetic, and antibody, a small molecule, or a polynucleotide (e.g., an antisense or ribozyme). An example of a test agent is a ligand that binds specifically with a HAM polypeptide, or other molecules capable of forming functional heteromers with a HAM polypeptide.

Cells used for these screening assays may include, for example, cells that naturally express a HAM polypeptide, such as glial cells, T-cells, myeloid cells and other hematopoietic cells, or any convenient cell type that has been transformed or transfected with a heterologous nucleic acid that directs the expression of a HAM polypeptide.

In other assays, cells expressing a bioactive fragment of a HAM polypeptide (e.g., a soluble form) may be cultured with the test molecule to determine whether the molecule has the capacity to modulate the amount of the bioactive fragment produced by the cells. The amount of bioactive fragment produced may be measured by any suitable method, including enzyme-linked immunosorbent assay (ELISA), dot blot employing an antibody that binds the bioactive fragment, or a solid phase binding assay.

Methods of Therapy

This invention provides compounds, compositions, and methods for treating a subject, preferably a mammalian subject, and most preferably a human subject, who is suffering from a medical disorder, and in particular a HAM-mediated disorder. Such HAM-mediated disorders include conditions caused (directly or indirectly) or exacerbated by binding between a HAM polypeptide and a binding partner. For purposes of this disclosure, the terms "illness," "disease," "medical condition," "abnormal condition," and the like are used interchangeably with the term "medical disorder." The terms "treat", "treating", and "treatment" used herein include curative, preventative (e.g., prophylactic) and palliative or ameliorative treatment.

The polypeptides and polynucleotides of the invention may be administered therapeutically to a mammalian subject (e.g., bovine, equine, feline, canine, porcine, primates), preferably a human subject, having a disorder involving a malfunctioning HAM gene or polypeptide, including an excess or a deficiency of such a polypeptide, or expression of a deleterious mutant form of the polypeptide. Such disorders include conditions caused (directly or indirectly) or exacerbated by such forms of the polypeptides. Where administration is to a human subject the molecules are preferably based upon a human HAM sequence (e.g., a sequence as set forth in SEQ ID NO:1 or 2).

For these therapeutic methods, agents that modulate activity or expression of a HAM polypeptide or polynucleotide, respectively, may be employed. Such modulating agents are identified by screening, such as by employing the screening methods disclosed herein. Antibodies that bind specifically with the HAM polypeptide or its ligand may modulate the biological activity of the HAM polypeptide.

Disorders and diseases treatable by the methods and compositions of the invention include, but are not limited to: rheumatologic disorders (e.g., rheumatoid arthritis, psoriatic arthritis, seronegative spondyloarthropathies), bone marrow or solid organ transplant, graft-versus-host reaction, inflammatory conditions, autoimmune disorders (e.g., systemic lupus erythematosus, Hashimoto's thyroiditis, Sjogren's syndrome), allergies (e.g., asthma, allergic rhinitis), neurologic disorders (e.g., Alzheimer's, Parkinson's, dementia, brain cancer, Bell's palsy, post-herpetic neuralgia), cancers (e.g., lymphoma, B-cell, T-cell and myeloid cell leukemias), infections (e.g., bacterial, parasitic, protozoal and viral infections, including AIDS), chemotherapy or radiation-induced toxicity, cachexia, cardiovascular disorders (e.g., congestive heart failure, myocardial infarction, ischemia/reperfusion injury, arteritis, stroke), diabetes mellitus, skin diseases (e.g., psoriasis, scleroderma, dermatomyositis), hematologic disorders (e.g., myelodysplastic syndromes, acquired or Fanconi's aplastic anemia), septic shock, liver diseases (e.g., viral hepatitis or alcohol-associated), bone disorders (e.g., osteoporosis, osteopetrosis), and weight-related or energy metabolism disorders including obesity.

For treating any one or more of the above disorders, the therapeutic agent, may be administered in an amount effective to measurably reduce one or more signs or symptoms of the disorder being treated. In addition, such disorders may be treated by administration in vivo or ex vivo of a vector or liposome that delivers a non-defective form of the malfunctioning gene to the cell type in which the malfunction is present.

Therapeutic compositions may comprise a substantially purified HAM polypeptide in any form described herein, such as a native polypeptide, a variant, a derivative, an oligomer, and a bioactive fragment. The composition may comprise a soluble polypeptide or an oligomer comprising a soluble HAM polypeptide. In another embodiment, a composition comprises an antibody directed against at least one HAM polypeptide epitope. In yet another embodiment, a therapeutic agent is attached to the antibody and the antibody is used to target the therapeutic agent to a cell expressing a HAM polypeptide.

Combination therapies also are envisioned, in which another pharmacologically active agent is co-administered with a therapeutic agent of the present invention. Other agents suitable for co-administration include, but are not limited to, cytokines, lymphokines, chemokines, chemotherapy agents, anti-inflammatories, DMARDs, anti-angiogenic agents (e.g., anti-VEGF antibodies), or any other compound effective in treating the target disease or disorder.

Pharmaceutical compositions of the invention furthermore may comprise other components such as a physiologically acceptable diluent, carrier, or excipient, and are formulated according to known methods. They can be combined in admixture, either as the sole active material or with other known active materials suitable for a given indication, with pharmaceutically acceptable diluents (e.g., saline, Tris-HCl, acetate, and phosphate buffered solutions), preservatives (e.g., thimerosal, benzyl alcohol, parabens), emulsifiers, solubilizers, adjuvants and/or carriers. Suitable formulations for pharmaceutical compositions include those described in *Remington's Pharmaceutical Sciences,* 16th ed. 1980, Mack Publishing Company, Easton, Pa.

In addition, such compositions can be complexed with polyethylene glycol (PEG), metal ions, or incorporated into polymeric compounds such as polyacetic acid, polyglycolic acid, hydrogels, dextran, and the like, or incorporated into liposomes, microemulsions, micelles, unilamellar or multilamellar vesicles, erythrocyte ghosts or spheroblasts. Such compositions will influence the physical state, solubility, stability, rate of in vivo release, and rate of in vivo clearance, and are thus chosen according to the intended application.

The compositions of the invention can be administered in any suitable manner, e.g., orally, topically, parenterally, or by inhalation. The term "parenteral" includes injection, e.g., by subcutaneous, intravenous, or intramuscular routes, also including localized administration, e.g., at a site of disease or injury. Sustained release from implants is also contemplated. Suitable dosages will vary, depending upon such factors as the nature of the disorder to be treated, the subject's body weight, age, and general condition, and the route of administration. Preliminary doses can be determined according to animal tests, and the scaling of dosages for human administration is performed according to art-accepted practices.

The dose, route of administration, frequency of administration and duration of an effective regimen of treatment will vary, depending factors such as the particular condition being treated, the severity of the condition, the age, weight, and health of the subject, and the like, and may be adjusted accordingly by the subject's physician.

In one method of treatment, the active agent is a polypeptide, and is administered by injection one to three times a week at a dose ranging from 0.1-100 mg/kg, or more preferably at a dose of 0.4-50 mg/kg. Treatment is continued until a measurable improvement in the subject's condition has been ascertained, which in most cases will require at least two to eight weeks or more of treatment. Maintenance doses may be administered thereafter, and treatment may be resumed if evidence of disease should reappear. Suitable regimens for other routes of administration may be determined according to methods known in the art. Similarly, suitable regimens for administering antibodies, small molecules, antisense or gene therapy reagents may be determined according to methods known in the art.

Included within the scope of the invention are pharmacologically acceptable compositions comprising the described therapeutic agents, including compositions suitable for administration by each of the described routes. Such compositions are formulated in accord with standard practices.

The following examples are provided to further illustrate particular embodiments of the invention, and are not to be construed as limiting the scope of the present invention.

EXAMPLES

Example 1

Identification, Cloning, and Sequencing of HAM

Mouse dendritic cell (DC) cDNA microarrays were used to identify novel DC-related genes. High-density nylon arrays were prepared from inserts from a cDNA library prepared from CD11c$^+$ mouse DCs, which were isolated from the spleens of Flt3L-treated/resting and Flt3L-treated/SEB-stimulated mice. These arrays were then hybridized with labeled first strand cDNAs from mouse DC subsets derived under a number of stimulation conditions. Differentially expressed genes were identified by differential array signals. Changes in signal patterns were identified and the corresponding clones were sequenced and analyzed. One identified clone which contained a sequence that was upregulated in CD8+/CD11b low (see Table immediately below), in vivo DC, was identified by a BLAST search as being most closely related to Attractin, a type I membrane protein with multiple biological functions, including immunoregulatory (promotion of macrophage spreading coupled to T cell adhesion; defective expression in Combined Variable Immunodeficiency), myelination (mutant gene in the Zitter rat), and metabolism (mutant gene in the Mahogany mouse). A BLAST search using the sequence obtained from the DC clone also identified GenBank accession CAC12966, an ORF predicted from a human genomic contig (GenBank AL355530) which appeared to be orthologous to the mouse DC sequence, and homologous to the N-terminus of Attractin. Additional BLAST analyses identified an EST from human brain cDNA (GenBank AB011106) which showed homology with the 3' end of Attractin. Both CAC12966 and AB011106 are incorporated herein by reference.

```
                    Upregulated sequence in CD8+/CD11b low
GGAGCCGGGGGTCCGGGCCCGCTCGGGTGCCCCGCAGCCGGCCTCCCCGGTGCTGTGGAG
 E  P  G  V  R  A  R  S  G  A  P  Q  P  A  S  P  V  L  W  R GGCTCGGCCGGCGGGCGGTGGGGCGCCTCCTCCTGGCTGCTGCTGGACGGGAACAGCTG
 A  R  P  A  G  G  G  A  S  S  W  L  L  L  D  G  N  S  W GCTGCTGTGCTATGGCTTCCTCTACCTGGCGCTCTATGCTCAGGTGTCCCAGTCCAAGCC
 L  L  C  Y  G  F  L  Y  L  A  L  Y  A  Q  V  S  Q  S  K  P CTGCGAGAGGACTGGCTCCTGCTTCTCCGGTCGCTGTGTCAACTCCACCTGCCTGTGCGA
 C  E  R  T  G  S  C  F  S  G  R  C  V  N  S  T  C  L  C  D CCCGGGCTGGGTTGGGGACCAGTGCCAGCACTGCCAGGGCAGGTTCAAGTTAACAGAACC
 P  G  W  V  G  D  Q  C  Q  H  C  Q  G  R  F  K  L  T  E  P TTCTGGATATTTAACAGATGGACCAATTAACTATAAATATAAAACAAAGTGTACATGGCT
 S  G  Y  L  T  D  G  P  I  N  Y  K  Y  K  T  K  C  T  W  L AATTGAAGGCTATCCAAATGCAGTGCTAAGGTTAAGATTCAATCATTTTGCTACAGAATG
 I  E  G  Y  P  N  A  V  L  R  L  R  F  N  H  F  A  T  E  C CAGCTGGGATCATATGTATGTTTATGATGGAGATTCTATATACGCACCTTTAGTAGCTGT
 S  W  D  H  M  Y  V  Y  D  G  D  S  I  Y  A  P  L  V  A  V ACTTAGTGGCTTGATCGTTCCTGAAGTGAGGGGTAACGAGACCGTGCCTGAGGTGGTCAC
 L  S  G  L  I  V  P  E  V  R  G  N  E  T  V  P  E  V  V  T GACGTCTGGCTACGCGCTGCTCCACTTTTTCAGCGATGCTGCATATAACCTAACTGGCTT
 T  S  G  Y  A  L  L  H  F  F  S  D  A  A  Y  N  L  T  G  F CAACATTTTTTATTCGATCAATTCCTGTCCTAACAACTGCTCTGGTCATGAAAGTGC
 N  I  F  Y  S  I  N  S  C  P  N  N  C  S  G  H  E  S
```

A full-length cDNA was amplified in six segments, using PCR primers based on AL355530 and AB011106 sequence. Human ovary cDNA library was used as a template for the PCR. Arrows superimposed on the sequence shown in FIG. 1 depict that position of primers for each fragment.

| Fragment | Size | Strand | Primers | |
|---|---|---|---|---|
| A | 494 bp | sense: | 5'-GGGGAAGATGGAGACTGG | (SEQ ID NO: 20) |
| | | antisense: | 5'-GTACAGCTATTAAAGGTGCATATATTGAATCTCC | (SEQ ID NO: 21) |
| B | 952 bp | sense: | 5'-TTAACAGAACCTTCTGGATATTTAACAGATGGC | (SEQ ID NO: 22) |
| | | antisense: | 5'-CTGAATGTCCCTCCACAGCATACTGCTG | (SEQ ID NO: 23) |
| C | 837 bp | sense: | 5'-GTTCTTGGACATGGTCAGCAGTATGCTGTG | (SEQ ID NO: 24) |
| | | antisense: | 5'-TTGTATTGGCAGTACAGCTGGCACAATCTG | (SEQ ID NO: 25) |
| D | 897 bp | sense: | 5'-GCTGCTTCTGATGACAGATGTTACAGATATGC | (SEQ ID NO: 26) |
| | | antisense: | 5'-CACATCCAGGCTGTTCCAAACACTGTCCAC | (SEQ ID NO: 27) |
| E | 855 bp | sense: | 5'-CCATATGGACAATGTCTAGAGTGGCAAACTGC | (SEQ ID NO: 28) |
| | | antisense: | 5'-GCTGACGTACACATAGAACGTAATGTTAGGATTGC | (SEQ ID NO: 29) |
| F | 650 bp | sense: | 5'-CAATATCTGGGGAAGAGACTTCTATAGTTTCCAAG | (SEQ ID NO: 30) |
| | | antisense: | 5'-GGTTTCCATTTCTCAGACACAAGTTCCTTGACGTGT | (SEQ ID NO: 31) |

Several PCR fragments from each amplification were ligated into a cloning vector for sequencing. Sequencing was conducted using standard methodology.

Example 2

Sequence Analysis

The open reading frame (ORF) of human HAM (SEQ ID NO:1) is predicted to be encoded on 29 exons. Four putative alternatively spliced variants were found during the PCR amplifications including a deletion of exon 7, deletion of exon 10, deletion of exon 19, and a deletion of exon 21. These variants/deletions may occur individually or in combination. In addition, various nucleotide substitutions were identified as follows with reference to SEQ ID NO:1:

| Nucleotide of SEQ ID NO:1 | Change | Type of Change | Result | Amino acid residue of SEQ ID NO:2 |
|---|---|---|---|---|
| 120 | aaC > aaT | Silent | Asn > Asn | 40 |
| 140 | gGc > gAc | | Gly > Asp | 46 |
| 400 | Aga > Gga | | Arg > Gly | 134 |
| 696 | taT > taC | Silent | Tyr > Tyr | 232 |
| 783 | tgT > tgC | Silent | Cys > Cys | 261 |
| 1213 | Cat > Tat | | His > Tyr | 405 |
| 1244 | tCa > tTa | | Ser > Leu | 415 |
| 1334 | cAg > cGg | | Gln > Arg | 445 |
| 1418 | gTg > gCc | | Val > Ala | 473 |
| 1779 | atG > atA | | Met > Ile | 593 |
| 1950 | aaT > aaC | Silent | Asn > Asn | 650 |
| 2084 | aAt > aGt | | Asn > Ser | 695 |
| 2097 | agT > agC | Silent | Ser > Ser | 699 |
| 2275 | Tgt > Cgt | | Cys > Arg | 759 |
| 2510 | cTt > cCt | | Leu > Pro | 837 |
| 2809 | Acc > Gcc | | Thr > Ala | 935 |
| 2843 | aCc > aTc | | Thr > Ile | 948 |
| 2947 | Ctt > TTT | | Leu > Phe | 982 |
| 3005 | aAg > aGg | | Lys > Arg | 1002 |
| 3013 | Gag > Aag | | Glu > Lys | 1005 |
| 3222 | Deleted | Frameshift | premature stop at 1074 | |
| 3226 | Tgt > Cgt | | Cys > Arg | 1076 |
| 3262 | Tgc > Cgc | | Cys > Arg | 1088 |
| 3288 | cgC > cgT | Silent | Arg > Arg | 1097 |
| 3374 | gAt > gGt | | Asp > Gly | 1125 |
| 3376 | Cgc > Tgc | | Arg > Cys | 1126 |
| 3523 | Tct > Cct | | Ser > Pro | 1175 |
| 3621-3626 | Deletion (in-frame) | | | 1207-1209 |

-continued

| Nucleotide of SEQ ID NO:1 | Change | Type of Change | Result | Amino acid residue of SEQ ID NO:2 |
|---|---|---|---|---|
| 3609 | acG > acA | Silent | Thr > Thr | 1203 |
| 3653 | cAg > cGG |  | Gln > Arg | 1218 |
| 3718 | Tgt > Cgt |  | Cys > Arg | 1240 |
| 3750 | gtG > gtA | silent | Val > Val | 1250 |
| 3877 | Aca > Gca |  | Thr > Ala | 1293 |
| 3881 | gAg > gGg |  | Glu > Gly | 1294 |
| 4039 | Cta > Tta | silent | Leu > Leu | 1347 |
| 4116 | tcA > tcG | silent | Ser > Ser | 1372 |

An analysis of the sequence as set forth in SEQ ID NO:2 or 19 identified distinct regions of the HAM polypeptides of the invention. A leader sequence, also called a signal peptide, is present in these polypeptides. For example, the leader sequence present in the full-length human HAM polypeptide of the invention is predicted to include amino acids 1-60 of SEQ ID NO:2 and amino acids 1-59 of SEQ ID NO:19. The signal peptide cleavage site for HAM was predicted using a computer algorithm. However, one of skill in the art will recognize that the cleavage site of the signal sequence may vary depending upon a number of factors including the organism in which the polypeptide is expressed. Accordingly, the N-terminus of a mature form of a HAM polypeptide of the invention may vary by about 2 to 5 amino acids. Thus, a mature form of the human HAM polypeptide of the invention may include at its N-terminus amino acids 55, 56, 57, 58, 59, 60, 61, 62, 63, 64, or 65 of SEQ ID NO:2. Accordingly, a mature form human HAM can include amino acid 55, 56, 57, 58, 59, 60, 61, 62, 63, 64, or 65 to about amino acid 1379 (or, in the case of a soluble polypeptide, to amino acid 1230) of SEQ ID NO:2. The extracellular regions of the human HAM polypeptides are located at about amino acids 61 to 1230 of SEQ ID NO:2. The EGF-like domains, CUB domain, C-type Lectin or carbohydrate-recognition domain (CLECT domain), KELCH motif and Laminin EGF-like domain assignments, as well as those for the transmembrane and cytoplasmic domains are based upon computer algorithms and on previous reports (Gunn et al., Nature 398:152-157, 1999). The extracellular region of human HAM putatively contains three EGF-like domains, a CUB domain, a KELCH motif, a C-type Lectin or carbohydrate-recognition domain, a putative ligand binding motif of the common gamma cytokine chain, and a Laminin EGF-like domain located at about amino acids 63-90, 211-243, 261-280, 93-208, 581-612, 749-873, 670-686, and 1014-1055 of SEQ ID NO:2, respectively (see FIG. 3). The transmembrane region for the human HAM polypeptides are located at about amino acids 1231 to 1251 of SEQ ID NO:2. The intracellular regions are located at about amino acids 1252 to 1379 of SEQ ID NO:2. In addition, the recognized sequences above, the sequence RXXHSAVX-INGXMXIFGG was found to be repeated in the human HAM sequence of the invention (see for example, amino acids 521 to 540 and 581 to 600 of SEQ ID NO:2). A BLAST of this repeated sequence identified a number attractin and mahogany sequences. Accordingly, this repeat sequence is a putative HAM conserved domain. FIG. 3 shows the relative domains and conserved residues of HAM indicative of an attractin or mahogany polypeptide.

Example 3

Tissue Expression of HAM

PCR for the attractin homolog used the following primers, which were designed to amplify an approximately 650 bp fragment from the predicted 3' end of the coding region. The primers were based on the predicted coding region found within the genomic sequence and are identical to sequences found in the AB011106 sequence:

```
sense strand                        (SEQ ID NO: 32)
5'CAATATCTGGGGAAGAGACTTCTATAGTTTCCAAG antisense                           (SEQ ID NO: 33)
5'GGTTTCCATTTCTCAGACACAAGTTCCTTGACGTGT
```

PCR showed a positive signal using these first strand cDNAs as templates in: placenta, liver, kidney, pancreas, spleen, testis, lymph node, heart, skeletal muscle, brain, ovary, small intestine, esophagus, fetal liver, fetal brain, fetal lung, fetal spleen, fetal, thymus, fetal kidney, and fetal skeletal muscle. No PCR product was detectable in stomach, bone marrow, lung, colon, prostate, thymus, leukocyte and skin. Accordingly, HAM may be used as a tissue specific marker.

Example 4

Monoclonal Antibodies that Bind HAM Polypeptides

Substantially purified HAM polypeptides or fragments thereof can be used to generate monoclonal antibodies immunoreactive therewith, using conventional techniques such as those described in U.S. Pat. No. 4,411,993. Briefly, mice are immunized with a HAM polypeptide immunogen emulsified in complete Freund's adjuvant, and injected in amounts ranging from 10-100 µg subcutaneously or intraperitoneally. Ten to twelve days later, the immunized animals are boosted with additional HAM polypeptide, or fragment thereof, emulsified in incomplete Freund's adjuvant. Mice are periodically boosted thereafter on a weekly to bi-weekly immunization schedule. Serum samples are periodically taken by retroorbital bleeding or tail-tip excision to test for HAM antibodies by dot blot assay, ELISA (Enzyme-Linked Immunosorbant Assay), or inhibition of binding of a HAM polypeptide to a HAM polypeptide binding partner.

Following detection of an appropriate antibody titer, positive animals are provided one last intravenous injection of a HAM polypeptide or fragment in saline. Three to four days later, the animals are sacrificed, spleen cells harvested, and spleen cells are fused to a murine myeloma cell line, e.g., NS1 or preferably P3x63Ag8.653 (ATCC CRL 1580). Fusions generate hybridoma cells, which are plated in multiple microtiter plates in a HAT (hypoxanthine, aminopterin and thymidine) selective medium to inhibit proliferation of non-fused cells, myeloma hybrids, and spleen cell hybrids.

The hybridoma cells are screened by ELISA for reactivity against a substantially pure HAM polypeptide by adaptations of the techniques disclosed in Engvall et al., (*Immunochem.* 8:871, 1971) and in U.S. Pat. No. 4,703,004. A preferred screening technique is the antibody capture technique described in Beckmann et al., (*J. Immunol.* 144:4212, 1990). Positive hybridoma cells can be injected intraperitoneally into syngeneic BALB/c mice to produce ascites containing high concentrations of anti-HAM polypeptide monoclonal antibody. Alternatively, hybridoma cells can be grown in vitro in flasks or roller bottles by various techniques. Monoclonal antibodies produced in mouse ascites can be purified by ammonium sulfate precipitation, followed by gel exclusion chromatography. Alternatively, affinity chromatography based upon binding of antibody to Polypeptide A or Polypeptide G can also be used, as can affinity chromatography based upon binding to HAM polypeptide.

Example 5

Chromosome Mapping

Chromosome mapping can be carried out in, for example, one of the following two methods. The gene corresponding to a HAM polypeptide is mapped using PCR-based mapping strategies. Initial human chromosomal assignments are made using HAM-specific PCR primers and a BIOS Somatic Cell Hybrid PCRable DNA kit from BIOS Laboratories (New Haven, Conn.), following the manufacturer's instructions. More detailed mapping is performed using a Genebridge 4 Radiation Hybrid Panel (Research Genetics, Huntsville, Ala.; described in Walter, M A et al., Nature Genetics 7:22-28, 1994). Data from this analysis is then submitted electronically to the MIT Radiation Hybrid Mapper following the instructions contained therein. This analysis yields specific genetic marker names which, when submitted electronically to the NCBI Genemap browser to yield the specific chromosome interval.

Alternatively, database analysis can yield information on the location of the polynucleotide sequence encoding HAM polypeptide. Analysis of human genomic contigs using the Celera human genome database identified the HAM sequence as being located on human chromosome 10q26.

Example 6

Binding Assay

HAM polypeptides or fragments thereof are expressed by recombinant DNA techniques, purified and tested for the ability to bind with various cells of the various lineages (e.g., hematopoietic cells). The binding assays employ HAM polypeptides, including soluble forms of these polypeptides, and oligomers formed as described below.

Oligomers for assays are prepared as follows. Fusion proteins comprising a leucine zipper peptide fused to the COOH-terminus of a HAM polypeptide are constructed as described above. The polypeptide can comprise a soluble form of HAM polypeptide, such as the extracellular region of a HAM polypeptide. An expression construct is prepared, essentially as described in Baum et al. (EMBO J. 13:3992-4001, 1994). The construct, in expression vector pDC409, encodes a leader sequence derived from human cytomegalovirus, followed by the leucine zipper moiety fused to the C-terminus of a soluble HAM polypeptide. Alternatively, a gene fusion encoding a HAM polypeptide/Fc fusion protein is inserted into an appropriate expression vector. Polypeptide/Fc fusion proteins are expressed in host cells transformed with the recombinant expression vector, and allowed to assemble by the formation of interchain disulfide bonds between the Fc moieties, thus yielding dimeric molecules.

The expressed Fc/HAM polypeptide or leucine zipper/HAM polypeptide fusion protein is contacted with a cell suspected of expressing a HAM polypeptide-binding partner. In one embodiment, the activity of the fusion protein is measured by detecting a change in energy metabolism or immune cell activation via any number of indicators. In another embodiment, the activity of the fusion protein is measured by detecting the ability of a cell expressing a native HAM polypeptide to bind to or interact with a cell expressing a HAM polypeptide-binding partner in the presence and absence of the fusion protein. In yet another embodiment, the binding activity of the fusion construct is detected by detecting binding of the fusion protein to a HAM polypeptide cognate using, for example, a labeled anti-IgG antibody.

What is claimed is:

1. A substantially purified polypeptide comprising the amino acid sequence set forth in SEQ ID NO:2.

2. A substantially purified polypeptide, wherein the polypeptide is selected from the group consisting of:
   (a) a polypeptide consisting of amino acids 61 to 1379 of SEQ ID NO:2; and
   (b) a polypeptide consisting of amino acids 61 to 1230 of SEQ ID NO:2.

3. A fusion polypeptide comprising a first polypeptide operably linked to a second polypeptide, wherein the first polypeptide is selected from the group consisting of:
   (a) a polypeptide consisting of amino acids 61 to 1230 of SEQ ID NO:2; and
   (b) a polypeptide consisting of amino acids 61 to 1379 of SEQ ID NO:2.

4. The fusion polypeptide of claim 3, wherein the second polypeptide is an Fc polypeptide.

5. The fusion polypeptide of claim 3, wherein the second polypeptide is a leucine zipper polypeptide.

6. The fusion polypeptide of claim 3, comprising a linker polypeptide separating the first polypeptide and the second polypeptide and operably linked to the first and second polypeptide.

7. An isolated polypeptide comprising an amino acid sequence consisting of SEQ ID NO: 2 with one amino acid substitution selected from the group consisting of: Asp at position 46, Gly at position 134, Tyr at position 405, Leu at position 415, Arg at position 445, Ala at position 473, Ile at position 593, Ser at position 695, Arg at position 759, Pro at position 837, Ala at position 935, Ile at position 948, Phe at position 982, Arg at position 1002, Lys at position 1005, Arg at position 1076, Arg at position 1088, Gly at position 1125, Cys at position 1126, Pro at position 1175, Arg at position 1218, Arg at position 1240, Ala at position 1293, and Gly at position 1294, wherein the polypeptide is capable of inducing monocyte or macrophage activation.

* * * * *

SEQUENCE LISTING

```
<160> NUMBER OF SEQ ID NOS: 33

<210> SEQ ID NO 1
<211> LENGTH: 4140
<212> TYPE: DNA
<213> ORGANISM: homo sapiens
<220> FEATURE:
<221> NAME/KEY: CDS
<222> LOCATION: (1)..(4140)

<400> SEQUENCE: 1 atg gag act ggg ggc cgg gcc cgc act ggt acc ccg cag cca gcg gcc      48
```

```
Met Glu Thr Gly Gly Arg Ala Arg Thr Gly Thr Pro Gln Pro Ala Ala
1               5                   10                  15 ccg ggg gtg tgg agg gct cgg ccg gcg ggc ggc ggc ggg ggc gcc         96
Pro Gly Val Trp Arg Ala Arg Pro Ala Gly Gly Gly Gly Gly Ala
                20                  25                  30 tcc tcc tgg ctg ctg gac ggg aac agc tgg ctg ctg tgc tat ggc ttc    144
Ser Ser Trp Leu Leu Asp Gly Asn Ser Trp Leu Leu Cys Tyr Gly Phe
        35                  40                  45 ctc tac ctg gcg ctc tac gcg cag gtg tcc cag tcc aag ccg tgc gag    192
Leu Tyr Leu Ala Leu Tyr Ala Gln Val Ser Gln Ser Lys Pro Cys Glu
    50                  55                  60 agg acc ggc tcc tgc ttc tcg ggc cgc tgt gtc aac tcc acc tgc ctc    240
Arg Thr Gly Ser Cys Phe Ser Gly Arg Cys Val Asn Ser Thr Cys Leu
65                  70                  75                  80 tgc gac ccg ggc tgg gtg ggg gac cag tgc cag cac tgc cag ggc agg    288
Cys Asp Pro Gly Trp Val Gly Asp Gln Cys Gln His Cys Gln Gly Arg
                85                  90                  95 ttc aag tta aca gaa cct tct gga tat tta aca gat ggc cca att aac    336
Phe Lys Leu Thr Glu Pro Ser Gly Tyr Leu Thr Asp Gly Pro Ile Asn
            100                 105                 110 tat aaa tat aaa act aaa tgt act tgg ctc att gaa ggc tat cca aat    384
Tyr Lys Tyr Lys Thr Lys Cys Thr Trp Leu Ile Glu Gly Tyr Pro Asn
        115                 120                 125 gca gtg tta aga tta aga ttc aat cat ttt gct aca gaa tgt agc tgg    432
Ala Val Leu Arg Leu Arg Phe Asn His Phe Ala Thr Glu Cys Ser Trp
    130                 135                 140 gat cat atg tat gtt tat gat gga gat tca ata tat gca cct tta ata    480
Asp His Met Tyr Val Tyr Asp Gly Asp Ser Ile Tyr Ala Pro Leu Ile
145                 150                 155                 160 gct gta ctt agt ggt ttg ata gtc cct gaa ata agg ggc aat gaa act    528
Ala Val Leu Ser Gly Leu Ile Val Pro Glu Ile Arg Gly Asn Glu Thr
                165                 170                 175 gtg cct gaa gtt gtt act aca tct ggc tat gca ctg tta cat ttt ttt    576
Val Pro Glu Val Val Thr Thr Ser Gly Tyr Ala Leu Leu His Phe Phe
            180                 185                 190 agt gat gct gcg tat aat cta act ggt ttc aac att ttc tat tca atc    624
Ser Asp Ala Ala Tyr Asn Leu Thr Gly Phe Asn Ile Phe Tyr Ser Ile
        195                 200                 205 aat tct tgt cct aac aat tgc tct ggt cat ggg aag tgt aca act agt    672
Asn Ser Cys Pro Asn Asn Cys Ser Gly His Gly Lys Cys Thr Thr Ser
    210                 215                 220 gtc tct gtt cca agt caa gta tat tgt gaa tgt gat aaa tac tgg aag    720
Val Ser Val Pro Ser Gln Val Tyr Cys Glu Cys Asp Lys Tyr Trp Lys
225                 230                 235                 240 ggt gaa gct tgt gat att cct tac tgt aaa gcc aat tgc ggc agt cca    768
Gly Glu Ala Cys Asp Ile Pro Tyr Cys Lys Ala Asn Cys Gly Ser Pro
                245                 250                 255 gat cac ggt tac tgt gac ctg act gga gaa aaa tta tgt gtc tgc aat    816
Asp His Gly Tyr Cys Asp Leu Thr Gly Glu Lys Leu Cys Val Cys Asn
            260                 265                 270 gat agt tgg caa ggt cct gat tgt tct ttg aat gtt ccc tct act gag    864
Asp Ser Trp Gln Gly Pro Asp Cys Ser Leu Asn Val Pro Ser Thr Glu
        275                 280                 285 tct tac tgg att ctg cca aac gtt aaa ccc ttc agt cct tct gta ggt    912
Ser Tyr Trp Ile Leu Pro Asn Val Lys Pro Phe Ser Pro Ser Val Gly
    290                 295                 300 cgg gct tca cat aaa gca gtt tta cac ggg aaa ttt atg tgg gtg att    960
Arg Ala Ser His Lys Ala Val Leu His Gly Lys Phe Met Trp Val Ile
305                 310                 315                 320
```

```
ggt gga tat act ttt aac tac agt tct ttt caa atg gtc cta aat tac     1008
Gly Gly Tyr Thr Phe Asn Tyr Ser Ser Phe Gln Met Val Leu Asn Tyr
            325                 330                 335 aat tta gaa agc agt ata tgg aat gta gga act cca tca agg gga cct     1056
Asn Leu Glu Ser Ser Ile Trp Asn Val Gly Thr Pro Ser Arg Gly Pro
        340                 345                 350 ctc cag aga tat gga cac tct ctt gct tta tat cag gaa aac atc ttt     1104
Leu Gln Arg Tyr Gly His Ser Leu Ala Leu Tyr Gln Glu Asn Ile Phe
            355                 360                 365 atg tat gga ggc aga att gaa aca aat gat ggc aat gtc aca gat gaa     1152
Met Tyr Gly Gly Arg Ile Glu Thr Asn Asp Gly Asn Val Thr Asp Glu
        370                 375                 380 tta tgg gtt ttt aac ata cat agt cag tca tgg agt aca aaa act cct     1200
Leu Trp Val Phe Asn Ile His Ser Gln Ser Trp Ser Thr Lys Thr Pro
385                 390                 395                 400 act gtt ctt gga cat ggt cag cag tat gct gtg gag gga cat tca gca     1248
Thr Val Leu Gly His Gly Gln Gln Tyr Ala Val Glu Gly His Ser Ala
            405                 410                 415 cat att atg gag ttg gat agt aga gat gtt gtc atg atc ata ata ttt     1296
His Ile Met Glu Leu Asp Ser Arg Asp Val Val Met Ile Ile Ile Phe
        420                 425                 430 gga tat tct gca ata tat ggt tat aca agc agc ata cag gaa tac cat     1344
Gly Tyr Ser Ala Ile Tyr Gly Tyr Thr Ser Ser Ile Gln Glu Tyr His
            435                 440                 445 atc tca tca aac act tgg ctt gtt cca gaa act aaa gga gct att gta     1392
Ile Ser Ser Asn Thr Trp Leu Val Pro Glu Thr Lys Gly Ala Ile Val
        450                 455                 460 caa ggt gga tat ggc cat act agt gtg tat gat gaa ata aca aag tcc     1440
Gln Gly Gly Tyr Gly His Thr Ser Val Tyr Asp Glu Ile Thr Lys Ser
465                 470                 475                 480 att tat gtt cat gga ggg tat aaa gca ttg cca ggg aac aaa tat gga     1488
Ile Tyr Val His Gly Gly Tyr Lys Ala Leu Pro Gly Asn Lys Tyr Gly
            485                 490                 495 ttg gtt gat gat ctt tat aaa tat gaa gtt aac act aag act tgg act     1536
Leu Val Asp Asp Leu Tyr Lys Tyr Glu Val Asn Thr Lys Thr Trp Thr
        500                 505                 510 att ttg aaa gaa agt ggg ttt gcc aga tac ctt cat tca gct gtt ctt     1584
Ile Leu Lys Glu Ser Gly Phe Ala Arg Tyr Leu His Ser Ala Val Leu
            515                 520                 525 atc aat gga gct atg ctt att ttt gga gga aat acc cat aat gac act     1632
Ile Asn Gly Ala Met Leu Ile Phe Gly Gly Asn Thr His Asn Asp Thr
        530                 535                 540 tcc ttg agt aac ggt gca aaa tgt ttt tct gcc gat ttc ctg gca tat     1680
Ser Leu Ser Asn Gly Ala Lys Cys Phe Ser Ala Asp Phe Leu Ala Tyr
545                 550                 555                 560 gac ata gct tgt gat gaa tgg aaa ata cta cca aaa cca aat ctt cat     1728
Asp Ile Ala Cys Asp Glu Trp Lys Ile Leu Pro Lys Pro Asn Leu His
            565                 570                 575 aga gat gtc aac aga ttt gga cac tct gca gta gtc att aac ggg tcc     1776
Arg Asp Val Asn Arg Phe Gly His Ser Ala Val Val Ile Asn Gly Ser
        580                 585                 590 atg tat ata ttt ggg gga ttt tct agt gta ctc ctt aat gat atc ctt     1824
Met Tyr Ile Phe Gly Gly Phe Ser Ser Val Leu Leu Asn Asp Ile Leu
            595                 600                 605 gta tac aag cct cca aat tgc aag gct ttc aga gat gaa gaa ctt tgt     1872
Val Tyr Lys Pro Pro Asn Cys Lys Ala Phe Arg Asp Glu Glu Leu Cys
        610                 615                 620 aaa aat gct ggt cca ggg ata aaa tgt gtt tgg aat aaa aat cac tgt     1920
Lys Asn Ala Gly Pro Gly Ile Lys Cys Val Trp Asn Lys Asn His Cys
625                 630                 635                 640
```

-continued

| | | |
|---|---|---|
| gaa tct tgg gaa tct ggg aat act aat aat att ctt aga gca aag tgc<br>Glu Ser Trp Glu Ser Gly Asn Thr Asn Asn Ile Leu Arg Ala Lys Cys<br>                                      645                        650                        655 | 1968 |
| cct cct aaa aca gct gct tct gat gac aga tgt tac aga tat gca gat<br>Pro Pro Lys Thr Ala Ala Ser Asp Asp Arg Cys Tyr Arg Tyr Ala Asp<br>                            660                        665                        670 | 2016 |
| tgt gcc agc tgt act gcc aat aca aat ggg tgc caa tgg tgt gat gac<br>Cys Ala Ser Cys Thr Ala Asn Thr Asn Gly Cys Gln Trp Cys Asp Asp<br>                      675                        680                        685 | 2064 |
| aag aaa tgc att tcg gca aat agt aac tgc agt atg tct gtc aag aac<br>Lys Lys Cys Ile Ser Ala Asn Ser Asn Cys Ser Met Ser Val Lys Asn<br>            690                        695                        700 | 2112 |
| tac acc aaa tgt cat gtg aga aat gag cag att tgt aac aaa ctt acc<br>Tyr Thr Lys Cys His Val Arg Asn Glu Gln Ile Cys Asn Lys Leu Thr<br>705                        710                        715                        720 | 2160 |
| agc tgt aaa agc tgt tca cta aac ttg aat tgc cag tgg gat cag aga<br>Ser Cys Lys Ser Cys Ser Leu Asn Leu Asn Cys Gln Trp Asp Gln Arg<br>                            725                        730                        735 | 2208 |
| cag caa gaa tgc cag gct tta cca gct cat ctt tgt gga gaa gga tgg<br>Gln Gln Glu Cys Gln Ala Leu Pro Ala His Leu Cys Gly Glu Gly Trp<br>            740                        745                        750 | 2256 |
| agt cat att ggg gat gct tgt ctt aga gtc aat tcc agt aga gaa aac<br>Ser His Ile Gly Asp Ala Cys Leu Arg Val Asn Ser Ser Arg Glu Asn<br>                      755                        760                        765 | 2304 |
| tat gac aat gca aaa ctt tat tgc tat aat ctt agt gga aat ctt gct<br>Tyr Asp Asn Ala Lys Leu Tyr Cys Tyr Asn Leu Ser Gly Asn Leu Ala<br>770                        775                        780 | 2352 |
| tca tta aca acc tca aaa gaa gta gaa ttt gtt ctg gat gaa ata cag<br>Ser Leu Thr Thr Ser Lys Glu Val Glu Phe Val Leu Asp Glu Ile Gln<br>785                        790                        795                        800 | 2400 |
| aag tat aca caa cag aaa gta tca cct tgg gta ggc ttg cgc aag atc<br>Lys Tyr Thr Gln Gln Lys Val Ser Pro Trp Val Gly Leu Arg Lys Ile<br>                            805                        810                        815 | 2448 |
| aat ata tcc tat tgg gga tgg gaa gac atg tct cct ttt aca aac aca<br>Asn Ile Ser Tyr Trp Gly Trp Glu Asp Met Ser Pro Phe Thr Asn Thr<br>            820                        825                        830 | 2496 |
| aca cta cag tgg ctt cct ggc gaa ccc aat gat tct ggg ttt tgt gca<br>Thr Leu Gln Trp Leu Pro Gly Glu Pro Asn Asp Ser Gly Phe Cys Ala<br>                      835                        840                        845 | 2544 |
| tat ctg gaa agg gct gca gtg gca ggc tta aaa gct aat cct tgt aca<br>Tyr Leu Glu Arg Ala Ala Val Ala Gly Leu Lys Ala Asn Pro Cys Thr<br>850                        855                        860 | 2592 |
| tct atg gca aat ggc ctt gtc tgt gaa aaa cct gtt gtt agt cca aat<br>Ser Met Ala Asn Gly Leu Val Cys Glu Lys Pro Val Val Ser Pro Asn<br>865                        870                        875                        880 | 2640 |
| caa aat gcg agg ccg tgc aaa aag cca tgc tct ctg agg aca tca tgt<br>Gln Asn Ala Arg Pro Cys Lys Lys Pro Cys Ser Leu Arg Thr Ser Cys<br>                            885                        890                        895 | 2688 |
| tcc aac tgt aca agc aat ggc atg gag tgt atg tgg tgc agc agt acg<br>Ser Asn Cys Thr Ser Asn Gly Met Glu Cys Met Trp Cys Ser Ser Thr<br>            900                        905                        910 | 2736 |
| aaa cga tgt gtt gac tct aat gcc tat atc atc tct ttt cca tat gga<br>Lys Arg Cys Val Asp Ser Asn Ala Tyr Ile Ile Ser Phe Pro Tyr Gly<br>                      915                        920                        925 | 2784 |
| caa tgt cta gag tgg caa act gcc acc tgt tcc cct caa aat tgt tct<br>Gln Cys Leu Glu Trp Gln Thr Ala Thr Cys Ser Pro Gln Asn Cys Ser<br>930                        935                        940 | 2832 |
| gga ttg aga acc tgt gga cag tgt ttg gaa cag cct gga tgt ggc tgg<br>Gly Leu Arg Thr Cys Gly Gln Cys Leu Glu Gln Pro Gly Cys Gly Trp | 2880 |

-continued

```
              945                 950                 955                 960
tgc aat gat cct agt aat aca gga aga gga cat tgc att gaa ggt tct    2928
Cys Asn Asp Pro Ser Asn Thr Gly Arg Gly His Cys Ile Glu Gly Ser
                    965                 970                 975 tca cgg gga cca atg aag ctt att gga atg cac cac aat gag atg gtt    2976
Ser Arg Gly Pro Met Lys Leu Ile Gly Met His His Asn Glu Met Val
                980                 985                 990 ctt gac acc aat ctt tgc ccc aaa  gaa aag aac tat gag  tgg tcc ttt  3024
Leu Asp Thr Asn Leu Cys Pro Lys  Glu Lys Asn Tyr Glu  Trp Ser Phe
                995                  1000                1005 atc cag tgt cca gct tgc cag tgt aat gga cat agc act tgc atc        3069
Ile Gln Cys Pro Ala Cys Gln Cys Asn Gly His Ser Thr Cys Ile
    1010                1015                1020 aat aat aat gtg tgc gaa cag tgt aaa aat ctc acc aca gga aag        3114
Asn Asn Asn Val Cys Glu Gln Cys Lys Asn Leu Thr Thr Gly Lys
    1025                1030                1035 cag tgt caa gat tgt atg cca ggt tat tat gga gat cca acc aat        3159
Gln Cys Gln Asp Cys Met Pro Gly Tyr Tyr Gly Asp Pro Thr Asn
    1040                1045                1050 ggt gga cag tgc aca gct tgt aca tgc agt ggc cat gca aat atc        3204
Gly Gly Gln Cys Thr Ala Cys Thr Cys Ser Gly His Ala Asn Ile
    1055                1060                1065 tgt cat ctg cac aca gga aaa tgt ttc tgc aca act aaa gga ata        3249
Cys His Leu His Thr Gly Lys Cys Phe Cys Thr Thr Lys Gly Ile
    1070                1075                1080 aaa ggt gac caa tgc caa tta tgt gac tct gaa aat cgc tat gtt        3294
Lys Gly Asp Gln Cys Gln Leu Cys Asp Ser Glu Asn Arg Tyr Val
    1085                1090                1095 ggt aat cca ctt aga gga aca tgt tat tac agc ctt ttg att gat        3339
Gly Asn Pro Leu Arg Gly Thr Cys Tyr Tyr Ser Leu Leu Ile Asp
    1100                1105                1110 tat caa ttt acc ttc agc tta tta cag gaa gat gat cgc cac cat        3384
Tyr Gln Phe Thr Phe Ser Leu Leu Gln Glu Asp Asp Arg His His
    1115                1120                1125 act gcc ata aac ttt ata gca aac cca gaa cag tcg aac aaa aat        3429
Thr Ala Ile Asn Phe Ile Ala Asn Pro Glu Gln Ser Asn Lys Asn
    1130                1135                1140 ctg gat ata tca att aat gca tca aac aac ttt aat ctc aac att        3474
Leu Asp Ile Ser Ile Asn Ala Ser Asn Asn Phe Asn Leu Asn Ile
    1145                1150                1155 acg tgg tct gtc ggt tca aca gct gga aca ata tct ggg gaa gag        3519
Thr Trp Ser Val Gly Ser Thr Ala Gly Thr Ile Ser Gly Glu Glu
    1160                1165                1170 act tct ata gtt tcc aag aat aat ata aag gaa tac aga gat agt        3564
Thr Ser Ile Val Ser Lys Asn Asn Ile Lys Glu Tyr Arg Asp Ser
    1175                1180                1185 ttt tcc tat gaa aaa ttt aac ttt aga agc aat cct aac att acg        3609
Phe Ser Tyr Glu Lys Phe Asn Phe Arg Ser Asn Pro Asn Ile Thr
    1190                1195                1200 ttc tat gtg tac gtc agc aac ttt tcc tgg cct att aaa ata cag        3654
Phe Tyr Val Tyr Val Ser Asn Phe Ser Trp Pro Ile Lys Ile Gln
    1205                1210                1215 att gca ttc tca caa cac aat aca atc atg gac ctt gtg cag ttt        3699
Ile Ala Phe Ser Gln His Asn Thr Ile Met Asp Leu Val Gln Phe
    1220                1225                1230 ttt gtc acc ttc ttc agt tgt ttc cta tcc tta ttg ctg gtg gct        3744
Phe Val Thr Phe Phe Ser Cys Phe Leu Ser Leu Leu Leu Val Ala
    1235                1240                1245 gct gtg gta tgg aag atc aaa caa act tgt tgg gct tct cga cgg        3789
```

-continued

```
Ala Val Val Trp Lys Ile Lys Gln Thr Cys Trp Ala Ser Arg Arg
    1250                1255                1260 aga gag caa ctg ctt cga gaa cga cag cag atg gcc agc cgt ccc     3834
Arg Glu Gln Leu Leu Arg Glu Arg Gln Gln Met Ala Ser Arg Pro
1265                1270                1275 ttt gct tct gtt gat gta gct ctg gaa gtg gga gct gaa caa aca     3879
Phe Ala Ser Val Asp Val Ala Leu Glu Val Gly Ala Glu Gln Thr
        1280                1285                1290 gag ttt ctg cga ggg cca tta gag ggg gca ccc aag cca att gcc     3924
Glu Phe Leu Arg Gly Pro Leu Glu Gly Ala Pro Lys Pro Ile Ala
    1295                1300                1305 att gaa cca tgt gct ggg aac aga gct gct gtt ctg act gtg ttt     3969
Ile Glu Pro Cys Ala Gly Asn Arg Ala Ala Val Leu Thr Val Phe
1310                1315                1320 ctt tgt cta cca cga gga tca tca ggt gcc cct ccc cct ggg cag     4014
Leu Cys Leu Pro Arg Gly Ser Ser Gly Ala Pro Pro Pro Gly Gln
        1325                1330                1335 tca ggc ctt gca att gcc agt gcc cta ata gat att tca caa cag     4059
Ser Gly Leu Ala Ile Ala Ser Ala Leu Ile Asp Ile Ser Gln Gln
    1340                1345                1350 aaa gct tca gat agt aaa gat aag act tct gga gtc cgg aat cga     4104
Lys Ala Ser Asp Ser Lys Asp Lys Thr Ser Gly Val Arg Asn Arg
1355                1360                1365 aaa cac ctt tca aca cgt caa gga act tgt gtc tga                 4140
Lys His Leu Ser Thr Arg Gln Gly Thr Cys Val
        1370                1375
```

<210> SEQ ID NO 2
<211> LENGTH: 1379
<212> TYPE: PRT
<213> ORGANISM: homo sapiens

<400> SEQUENCE: 2

```
Met Glu Thr Gly Gly Arg Ala Arg Thr Gly Thr Pro Gln Pro Ala Ala
1               5                   10                  15

Pro Gly Val Trp Arg Ala Arg Pro Ala Gly Gly Gly Gly Gly Gly Ala
            20                  25                  30

Ser Ser Trp Leu Leu Asp Gly Asn Ser Trp Leu Leu Cys Tyr Gly Phe
        35                  40                  45

Leu Tyr Leu Ala Leu Tyr Ala Gln Val Ser Gln Ser Lys Pro Cys Glu
    50                  55                  60

Arg Thr Gly Ser Cys Phe Ser Gly Arg Cys Val Asn Ser Thr Cys Leu
65                  70                  75                  80

Cys Asp Pro Gly Trp Val Gly Asp Gln Cys Gln His Cys Gln Gly Arg
                85                  90                  95

Phe Lys Leu Thr Glu Pro Ser Gly Tyr Leu Thr Asp Gly Pro Ile Asn
            100                 105                 110

Tyr Lys Tyr Lys Thr Lys Cys Thr Trp Leu Ile Glu Gly Tyr Pro Asn
        115                 120                 125

Ala Val Leu Arg Leu Arg Phe Asn His Phe Ala Thr Glu Cys Ser Trp
    130                 135                 140

Asp His Met Tyr Val Tyr Asp Gly Asp Ser Ile Tyr Ala Pro Leu Ile
145                 150                 155                 160

Ala Val Leu Ser Gly Leu Ile Val Pro Glu Ile Arg Gly Asn Glu Thr
                165                 170                 175

Val Pro Glu Val Val Thr Thr Ser Gly Tyr Ala Leu Leu His Phe Phe
            180                 185                 190
```

-continued

```
Ser Asp Ala Ala Tyr Asn Leu Thr Gly Phe Asn Ile Phe Tyr Ser Ile
        195                 200                 205
Asn Ser Cys Pro Asn Asn Cys Ser Gly His Gly Lys Cys Thr Thr Ser
    210                 215                 220
Val Ser Val Pro Ser Gln Val Tyr Cys Glu Cys Asp Lys Tyr Trp Lys
225                 230                 235                 240
Gly Glu Ala Cys Asp Ile Pro Tyr Cys Lys Ala Asn Cys Gly Ser Pro
            245                 250                 255
Asp His Gly Tyr Cys Asp Leu Thr Gly Glu Lys Leu Cys Val Cys Asn
        260                 265                 270
Asp Ser Trp Gln Gly Pro Asp Cys Ser Leu Asn Val Pro Ser Thr Glu
    275                 280                 285
Ser Tyr Trp Ile Leu Pro Asn Val Lys Pro Phe Ser Pro Ser Val Gly
    290                 295                 300
Arg Ala Ser His Lys Ala Val Leu His Gly Lys Phe Met Trp Val Ile
305                 310                 315                 320
Gly Gly Tyr Thr Phe Asn Tyr Ser Ser Phe Gln Met Val Leu Asn Tyr
            325                 330                 335
Asn Leu Glu Ser Ser Ile Trp Asn Val Gly Thr Pro Ser Arg Gly Pro
        340                 345                 350
Leu Gln Arg Tyr Gly His Ser Leu Ala Leu Tyr Gln Glu Asn Ile Phe
    355                 360                 365
Met Tyr Gly Gly Arg Ile Glu Thr Asn Asp Gly Asn Val Thr Asp Glu
    370                 375                 380
Leu Trp Val Phe Asn Ile His Ser Gln Ser Trp Ser Thr Lys Thr Pro
385                 390                 395                 400
Thr Val Leu Gly His Gly Gln Gln Tyr Ala Val Glu Gly His Ser Ala
            405                 410                 415
His Ile Met Glu Leu Asp Ser Arg Asp Val Val Met Ile Ile Ile Phe
        420                 425                 430
Gly Tyr Ser Ala Ile Tyr Gly Tyr Thr Ser Ser Ile Gln Glu Tyr His
    435                 440                 445
Ile Ser Ser Asn Thr Trp Leu Val Pro Glu Thr Lys Gly Ala Ile Val
    450                 455                 460
Gln Gly Gly Tyr Gly His Thr Ser Val Tyr Asp Glu Ile Thr Lys Ser
465                 470                 475                 480
Ile Tyr Val His Gly Gly Tyr Lys Ala Leu Pro Gly Asn Lys Tyr Gly
            485                 490                 495
Leu Val Asp Asp Leu Tyr Lys Tyr Glu Val Asn Thr Lys Thr Trp Thr
        500                 505                 510
Ile Leu Lys Glu Ser Gly Phe Ala Arg Tyr Leu His Ser Ala Val Leu
    515                 520                 525
Ile Asn Gly Ala Met Leu Ile Phe Gly Gly Asn Thr His Asn Asp Thr
    530                 535                 540
Ser Leu Ser Asn Gly Ala Lys Cys Phe Ser Ala Asp Phe Leu Ala Tyr
545                 550                 555                 560
Asp Ile Ala Cys Asp Glu Trp Lys Ile Leu Pro Lys Pro Asn Leu His
            565                 570                 575
Arg Asp Val Asn Arg Phe Gly His Ser Ala Val Val Ile Asn Gly Ser
        580                 585                 590
Met Tyr Ile Phe Gly Gly Phe Ser Ser Val Leu Leu Asn Asp Ile Leu
    595                 600                 605
Val Tyr Lys Pro Pro Asn Cys Lys Ala Phe Arg Asp Glu Glu Leu Cys
```

-continued

```
            610                 615                 620
Lys Asn Ala Gly Pro Gly Ile Lys Cys Val Trp Asn Lys Asn His Cys
625                 630                 635                 640

Glu Ser Trp Glu Ser Gly Asn Thr Asn Asn Ile Leu Arg Ala Lys Cys
                    645                 650                 655

Pro Pro Lys Thr Ala Ala Ser Asp Asp Arg Cys Tyr Arg Tyr Ala Asp
                    660                 665                 670

Cys Ala Ser Cys Thr Ala Asn Thr Asn Gly Cys Gln Trp Cys Asp Asp
                675                 680                 685

Lys Lys Cys Ile Ser Ala Asn Ser Asn Cys Ser Met Ser Val Lys Asn
            690                 695                 700

Tyr Thr Lys Cys His Val Arg Asn Glu Gln Ile Cys Asn Lys Leu Thr
705                 710                 715                 720

Ser Cys Lys Ser Cys Ser Leu Asn Leu Asn Cys Gln Trp Asp Gln Arg
                    725                 730                 735

Gln Gln Glu Cys Gln Ala Leu Pro Ala His Leu Cys Gly Glu Gly Trp
                    740                 745                 750

Ser His Ile Gly Asp Ala Cys Leu Arg Val Asn Ser Ser Arg Glu Asn
                755                 760                 765

Tyr Asp Asn Ala Lys Leu Tyr Cys Tyr Asn Leu Ser Gly Asn Leu Ala
            770                 775                 780

Ser Leu Thr Thr Ser Lys Glu Val Glu Phe Val Leu Asp Glu Ile Gln
785                 790                 795                 800

Lys Tyr Thr Gln Gln Lys Val Ser Pro Trp Val Gly Leu Arg Lys Ile
                    805                 810                 815

Asn Ile Ser Tyr Trp Gly Trp Glu Asp Met Ser Pro Phe Thr Asn Thr
                    820                 825                 830

Thr Leu Gln Trp Leu Pro Gly Glu Pro Asn Asp Ser Gly Phe Cys Ala
                835                 840                 845

Tyr Leu Glu Arg Ala Ala Val Ala Gly Leu Lys Ala Asn Pro Cys Thr
            850                 855                 860

Ser Met Ala Asn Gly Leu Val Cys Glu Lys Pro Val Val Ser Pro Asn
865                 870                 875                 880

Gln Asn Ala Arg Pro Cys Lys Lys Pro Cys Ser Leu Arg Thr Ser Cys
                    885                 890                 895

Ser Asn Cys Thr Ser Asn Gly Met Glu Cys Met Trp Cys Ser Ser Thr
                    900                 905                 910

Lys Arg Cys Val Asp Ser Asn Ala Tyr Ile Ile Ser Phe Pro Tyr Gly
                915                 920                 925

Gln Cys Leu Glu Trp Gln Thr Ala Thr Cys Ser Pro Gln Asn Cys Ser
            930                 935                 940

Gly Leu Arg Thr Cys Gly Gln Cys Leu Glu Gln Pro Gly Cys Gly Trp
945                 950                 955                 960

Cys Asn Asp Pro Ser Asn Thr Gly Arg Gly His Cys Ile Glu Gly Ser
                    965                 970                 975

Ser Arg Gly Pro Met Lys Leu Ile Gly Met His His Asn Glu Met Val
                980                 985                 990

Leu Asp Thr Asn Leu Cys Pro Lys Glu Lys Asn Tyr Glu Trp Ser Phe
                995                 1000                1005

Ile Gln Cys Pro Ala Cys Gln Cys Asn Gly His Ser Thr Cys Ile
            1010                1015                1020

Asn Asn Asn Val Cys Glu Gln Cys Lys Asn Leu Thr Thr Gly Lys
            1025                1030                1035
```

```
Gln Cys Gln Asp Cys Met Pro Gly Tyr Tyr Gly Asp Pro Thr Asn
    1040                1045                1050

Gly Gly Gln Cys Thr Ala Cys Thr Cys Ser Gly His Ala Asn Ile
    1055                1060                1065

Cys His Leu His Thr Gly Lys Cys Phe Cys Thr Thr Lys Gly Ile
    1070                1075                1080

Lys Gly Asp Gln Cys Gln Leu Cys Asp Ser Glu Asn Arg Tyr Val
    1085                1090                1095

Gly Asn Pro Leu Arg Gly Thr Cys Tyr Tyr Ser Leu Leu Ile Asp
    1100                1105                1110

Tyr Gln Phe Thr Phe Ser Leu Leu Gln Glu Asp Asp Arg His His
    1115                1120                1125

Thr Ala Ile Asn Phe Ile Ala Asn Pro Glu Gln Ser Asn Lys Asn
    1130                1135                1140

Leu Asp Ile Ser Ile Asn Ala Ser Asn Asn Phe Asn Leu Asn Ile
    1145                1150                1155

Thr Trp Ser Val Gly Ser Thr Ala Gly Thr Ile Ser Gly Glu Glu
    1160                1165                1170

Thr Ser Ile Val Ser Lys Asn Asn Ile Lys Glu Tyr Arg Asp Ser
    1175                1180                1185

Phe Ser Tyr Glu Lys Phe Asn Phe Arg Ser Asn Pro Asn Ile Thr
    1190                1195                1200

Phe Tyr Val Tyr Val Ser Asn Phe Ser Trp Pro Ile Lys Ile Gln
    1205                1210                1215

Ile Ala Phe Ser Gln His Asn Thr Ile Met Asp Leu Val Gln Phe
    1220                1225                1230

Phe Val Thr Phe Phe Ser Cys Phe Leu Ser Leu Leu Leu Val Ala
    1235                1240                1245

Ala Val Val Trp Lys Ile Lys Gln Thr Cys Trp Ala Ser Arg Arg
    1250                1255                1260

Arg Glu Gln Leu Leu Arg Glu Arg Gln Gln Met Ala Ser Arg Pro
    1265                1270                1275

Phe Ala Ser Val Asp Val Ala Leu Glu Val Gly Ala Glu Gln Thr
    1280                1285                1290

Glu Phe Leu Arg Gly Pro Leu Glu Gly Ala Pro Lys Pro Ile Ala
    1295                1300                1305

Ile Glu Pro Cys Ala Gly Asn Arg Ala Ala Val Leu Thr Val Phe
    1310                1315                1320

Leu Cys Leu Pro Arg Gly Ser Ser Gly Ala Pro Pro Gly Gln
    1325                1330                1335

Ser Gly Leu Ala Ile Ala Ser Ala Leu Ile Asp Ile Ser Gln Gln
    1340                1345                1350

Lys Ala Ser Asp Ser Lys Asp Lys Thr Ser Gly Val Arg Asn Arg
    1355                1360                1365

Lys His Leu Ser Thr Arg Gln Gly Thr Cys Val
    1370                1375

<210> SEQ ID NO 3
<211> LENGTH: 8
<212> TYPE: PRT
<213> ORGANISM: Artificial Sequence
<220> FEATURE:
<223> OTHER INFORMATION: FLAG peptide sequence

<400> SEQUENCE: 3
```

```
Asp Tyr Lys Asp Asp Asp Lys
1               5

<210> SEQ ID NO 4
<211> LENGTH: 5
<212> TYPE: PRT
<213> ORGANISM: Artificial Sequence
<220> FEATURE:
<223> OTHER INFORMATION: Peptide Linker

<400> SEQUENCE: 4

Gly Gly Gly Gly Ser
1               5

<210> SEQ ID NO 5
<211> LENGTH: 6
<212> TYPE: PRT
<213> ORGANISM: Artificial Sequence
<220> FEATURE:
<223> OTHER INFORMATION: Peptide Linker
<220> FEATURE:
<221> NAME/KEY: MISC_FEATURE
<222> LOCATION: (6)..(6)
<223> OTHER INFORMATION: X is one or more repeats of GGGGS

<400> SEQUENCE: 5

Gly Gly Gly Gly Ser Xaa
1               5

<210> SEQ ID NO 6
<211> LENGTH: 12
<212> TYPE: PRT
<213> ORGANISM: Artificial Sequence
<220> FEATURE:
<223> OTHER INFORMATION: Peptide Linker

<400> SEQUENCE: 6

Gly Lys Ser Ser Gly Ser Gly Ser Glu Ser Lys Ser
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Peptide Linker

<400> SEQUENCE: 7

Gly Ser Thr Ser Gly Ser Gly Lys Ser Ser Glu Gly Lys Gly
1               5                   10

<210> SEQ ID NO 8
<211> LENGTH: 18
<212> TYPE: PRT
<213> ORGANISM: Artificial Sequence
<220> FEATURE:
<223> OTHER INFORMATION: Peptide Linker

<400> SEQUENCE: 8

Gly Ser Thr Ser Gly Ser Gly Lys Ser Ser Glu Gly Ser Gly Ser Thr
1               5                   10                  15

Lys Gly

<210> SEQ ID NO 9
<211> LENGTH: 18
<212> TYPE: PRT
```

```
<213> ORGANISM: Artificial Sequence
<220> FEATURE:
<223> OTHER INFORMATION: Peptide Linker

<400> SEQUENCE: 9

Gly Ser Thr Ser Gly Ser Gly Lys Pro Gly Ser Gly Glu Gly Ser Thr
1               5                   10                  15

Lys Gly

<210> SEQ ID NO 10
<211> LENGTH: 14
<212> TYPE: PRT
<213> ORGANISM: Artificial Sequence
<220> FEATURE:
<223> OTHER INFORMATION: Peptide Linker

<400> SEQUENCE: 10

Glu Gly Lys Ser Ser Gly Ser Gly Ser Glu Ser Lys Glu Phe
1               5                   10

<210> SEQ ID NO 11
<211> LENGTH: 27
<212> TYPE: PRT
<213> ORGANISM: Artificial Sequence
<220> FEATURE:
<223> OTHER INFORMATION: Leucine Zipper Peptide

<400> SEQUENCE: 11

Pro Asp Val Ala Ser Leu Arg Gln Gln Val Glu Ala Leu Gln Gly Gln
1               5                   10                  15

Val Gln His Leu Gln Ala Ala Phe Ser Gln Tyr
            20                  25

<210> SEQ ID NO 12
<211> LENGTH: 33
<212> TYPE: PRT
<213> ORGANISM: Artificial Sequence
<220> FEATURE:
<223> OTHER INFORMATION: Leucine Zipper Peptide

<400> SEQUENCE: 12

Arg Met Lys Gly Ile Glu Asp Lys Ile Glu Glu Ile Leu Ser Lys Phe
1               5                   10                  15

Tyr His Ile Glu Asn Glu Ile Ala Arg Ile Lys Lys Leu Ile Gly Glu
            20                  25                  30

Arg

<210> SEQ ID NO 13
<211> LENGTH: 5
<212> TYPE: PRT
<213> ORGANISM: Artificial Sequence
<220> FEATURE:
<223> OTHER INFORMATION: Peptide Localization Sequence

<400> SEQUENCE: 13

Lys Lys Lys Arg Lys
1               5

<210> SEQ ID NO 14
<211> LENGTH: 26
<212> TYPE: PRT
<213> ORGANISM: Artificial Sequence
<220> FEATURE:
<223> OTHER INFORMATION: Peptide Localization Sequence
```

-continued

```
<400> SEQUENCE: 14

Met Leu Arg Thr Ser Ser Leu Phe Thr Arg Arg Val Gln Pro Ser Leu
1               5                   10                  15

Phe Arg Asn Ile Leu Arg Leu Gln Ser Thr
            20                  25

<210> SEQ ID NO 15
<211> LENGTH: 4
<212> TYPE: PRT
<213> ORGANISM: Artificial Sequence
<220> FEATURE:
<223> OTHER INFORMATION: Peptide Localization Sequence

<400> SEQUENCE: 15

Lys Asp Glu Leu
1

<210> SEQ ID NO 16
<211> LENGTH: 4
<212> TYPE: PRT
<213> ORGANISM: Artificial Sequence
<220> FEATURE:
<223> OTHER INFORMATION: Peptide Localization Sequence
<220> FEATURE:
<221> NAME/KEY: misc_feature
<222> LOCATION: (4)..(4)
<223> OTHER INFORMATION: X is any amino acid

<400> SEQUENCE: 16

Cys Ala Ala Xaa
1

<210> SEQ ID NO 17
<211> LENGTH: 4
<212> TYPE: PRT
<213> ORGANISM: Artificial Sequence
<220> FEATURE:
<223> OTHER INFORMATION: Peptide Localization Sequence
<220> FEATURE:
<221> NAME/KEY: Misc_feature
<222> LOCATION: (3)..(4)
<223> OTHER INFORMATION: X is any amino acid

<400> SEQUENCE: 17

Cys Cys Xaa Xaa
1

<210> SEQ ID NO 18
<211> LENGTH: 4134
<212> TYPE: DNA
<213> ORGANISM: homo sapiens
<220> FEATURE:
<221> NAME/KEY: CDS
<222> LOCATION: (1)..(4134)

<400> SEQUENCE: 18 atg gag ccg ggg gtc cgg gcc cgc tcg ggt gcc ccg cag ccg gcc tcc    48
Met Glu Pro Gly Val Arg Ala Arg Ser Gly Ala Pro Gln Pro Ala Ser
1               5                   10                  15 ccg gtg ctg tgg agg gct cgg ccg gcg ggc ggt ggg ggc gcc tcc tcc    96
Pro Val Leu Trp Arg Ala Arg Pro Ala Gly Gly Gly Gly Ala Ser Ser
            20                  25                  30 tgg ctg ctg ctg gac ggg aac agc tgg ctg ctg tgc tat ggc ttc ctc   144
Trp Leu Leu Leu Asp Gly Asn Ser Trp Leu Leu Cys Tyr Gly Phe Leu
        35                  40                  45 tac ctg gcg ctc tat gct cag gtg tcc cag tcc aag ccc tgc gag agg   192
```

```
                Tyr Leu Ala Leu Tyr Ala Gln Val Ser Gln Ser Lys Pro Cys Glu Arg
                     50                  55                  60 act ggc tcc tgc ttc tcc ggt cgc tgt gtc aac tcc acc tgc ctg tgc         240
Thr Gly Ser Cys Phe Ser Gly Arg Cys Val Asn Ser Thr Cys Leu Cys
 65                  70                  75                  80 gac ccg ggc tgg gtt ggg gac cag tgc cag cac tgc cag ggc agg ttc         288
Asp Pro Gly Trp Val Gly Asp Gln Cys Gln His Cys Gln Gly Arg Phe
                 85                  90                  95 aag tta aca gaa cct tct gga tat tta aca gat gga cca att aac tat         336
Lys Leu Thr Glu Pro Ser Gly Tyr Leu Thr Asp Gly Pro Ile Asn Tyr
                100                 105                 110 aaa tat aaa aca aag tgt aca tgg cta att gaa ggc tat cca aat gca         384
Lys Tyr Lys Thr Lys Cys Thr Trp Leu Ile Glu Gly Tyr Pro Asn Ala
                115                 120                 125 gtg cta agg tta aga ttc aat cat ttt gct aca gaa tgc agc tgg gat         432
Val Leu Arg Leu Arg Phe Asn His Phe Ala Thr Glu Cys Ser Trp Asp
        130                 135                 140 cat atg tat gtt tat gat gga gat tct ata tac gca cct tta gta gct         480
His Met Tyr Val Tyr Asp Gly Asp Ser Ile Tyr Ala Pro Leu Val Ala
145                 150                 155                 160 gta ctt agt ggc ttg atc gtt cct gaa gtg agg ggt aac gag acc gtg         528
Val Leu Ser Gly Leu Ile Val Pro Glu Val Arg Gly Asn Glu Thr Val
                165                 170                 175 cct gag gtg gtc acg acg tct ggc tac gcg ctc ctc cac ttt ttc agc         576
Pro Glu Val Val Thr Thr Ser Gly Tyr Ala Leu Leu His Phe Phe Ser
                180                 185                 190 gat gct gca tat aac cta act ggc ttc aac att ttt tat tcg atc aat         624
Asp Ala Ala Tyr Asn Leu Thr Gly Phe Asn Ile Phe Tyr Ser Ile Asn
                195                 200                 205 tcc tgt cct aac aac tgc tct ggt cat gga aag tgt aca acc agt gtc         672
Ser Cys Pro Asn Asn Cys Ser Gly His Gly Lys Cys Thr Thr Ser Val
        210                 215                 220 tct gtt gca agt caa gtg tat tgt gaa tgc gac aaa tac tgg aaa ggg         720
Ser Val Ala Ser Gln Val Tyr Cys Glu Cys Asp Lys Tyr Trp Lys Gly
225                 230                 235                 240 gaa gca tgt gac att cct tac tgt aaa gcc aat tgt ggg agt cca gat         768
Glu Ala Cys Asp Ile Pro Tyr Cys Lys Ala Asn Cys Gly Ser Pro Asp
                245                 250                 255 cat ggc tac tgt gac cta aca gga gag aaa ctc tgt gtc tgc aac gat         816
His Gly Tyr Cys Asp Leu Thr Gly Glu Lys Leu Cys Val Cys Asn Asp
                260                 265                 270 agt tgg caa ggc cca gat tgt tct ctg aat gtc cct tct act gag tct         864
Ser Trp Gln Gly Pro Asp Cys Ser Leu Asn Val Pro Ser Thr Glu Ser
        275                 280                 285 tac tgg att ttg cca aat gtt aaa ccc ttc agc cct tcc gta ggt cgg         912
Tyr Trp Ile Leu Pro Asn Val Lys Pro Phe Ser Pro Ser Val Gly Arg
        290                 295                 300 gcc tca cat aaa gca gtt tta cat ggg aaa ttc atg tgg gtg att gga         960
Ala Ser His Lys Ala Val Leu His Gly Lys Phe Met Trp Val Ile Gly
305                 310                 315                 320 gga tat act ttt aac tac agt tct ttt caa atg gtt ctg aat tac aat        1008
Gly Tyr Thr Phe Asn Tyr Ser Ser Phe Gln Met Val Leu Asn Tyr Asn
                325                 330                 335 tta gaa agc agt ata tgg aat gta ggt gct gta tca agg ggc cct ctt        1056
Leu Glu Ser Ser Ile Trp Asn Val Gly Ala Val Ser Arg Gly Pro Leu
                340                 345                 350 cag aga tac gga cat tct ctt gcc ctc tat cag gaa aac atc ttt atg        1104
Gln Arg Tyr Gly His Ser Leu Ala Leu Tyr Gln Glu Asn Ile Phe Met
        355                 360                 365
```

```
tac gga ggc aga atg gag acc agt gat ggc aac gtc acc gat gaa tta    1152
Tyr Gly Gly Arg Met Glu Thr Ser Asp Gly Asn Val Thr Asp Glu Leu
    370                 375                 380 tgg gtg ttt aac gta cgc agt caa tca tgg agc acg aaa acc ccc act    1200
Trp Val Phe Asn Val Arg Ser Gln Ser Trp Ser Thr Lys Thr Pro Thr
385                 390                 395                 400 gtc ctt ggc cac agt cag cag tac gct gtg gag gga cac tcg gca cac    1248
Val Leu Gly His Ser Gln Gln Tyr Ala Val Glu Gly His Ser Ala His
            405                 410                 415 atc atg gag ctg gac agt aga gac gtg gtc atg att gtc ata ttt gga    1296
Ile Met Glu Leu Asp Ser Arg Asp Val Val Met Ile Val Ile Phe Gly
        420                 425                 430 tat tct gca ata tat ggc tat acc agc agc ata cag gaa tac cat atc    1344
Tyr Ser Ala Ile Tyr Gly Tyr Thr Ser Ser Ile Gln Glu Tyr His Ile
    435                 440                 445 tcc tca aac act tgg cta gtt cca gaa acg aaa gga gcc att gtg caa    1392
Ser Ser Asn Thr Trp Leu Val Pro Glu Thr Lys Gly Ala Ile Val Gln
450                 455                 460 ggt gga tat ggc cac aca agt gtg tat gac gaa gtg acc aag tcc atc    1440
Gly Gly Tyr Gly His Thr Ser Val Tyr Asp Glu Val Thr Lys Ser Ile
465                 470                 475                 480 tat gtt cac gga ggc tac aaa gca ttg cct ggc aat aag tac ggg ctg    1488
Tyr Val His Gly Gly Tyr Lys Ala Leu Pro Gly Asn Lys Tyr Gly Leu
            485                 490                 495 gtg gac gac ctc tat aag tac gaa gtc aac acc agg act tgg act att    1536
Val Asp Asp Leu Tyr Lys Tyr Glu Val Asn Thr Arg Thr Trp Thr Ile
        500                 505                 510 ttg aaa gaa agt ggg ttt gcc aga tac ctt cac tca gct gtt ctt atc    1584
Leu Lys Glu Ser Gly Phe Ala Arg Tyr Leu His Ser Ala Val Leu Ile
    515                 520                 525 aat gga gct atg ctt att ttt gga gga aat acc cat aat gat act tcc    1632
Asn Gly Ala Met Leu Ile Phe Gly Gly Asn Thr His Asn Asp Thr Ser
530                 535                 540 ctg agt aac ggt gca aaa tgt ttt tct gcc gat ttc ctg gca tat gac    1680
Leu Ser Asn Gly Ala Lys Cys Phe Ser Ala Asp Phe Leu Ala Tyr Asp
545                 550                 555                 560 ata gct tgt gac gaa tgg aag aca ttg cct aaa cca aat ctc cat aga    1728
Ile Ala Cys Asp Glu Trp Lys Thr Leu Pro Lys Pro Asn Leu His Arg
            565                 570                 575 gac gtc aac cga ttt ggg cat tct gca gtc gtc atc aat ggg tca atg    1776
Asp Val Asn Arg Phe Gly His Ser Ala Val Val Ile Asn Gly Ser Met
        580                 585                 590 tat ata ttt ggt gga ttt tct agt gta ctc ctt aat gat atc ctt gtg    1824
Tyr Ile Phe Gly Gly Phe Ser Ser Val Leu Leu Asn Asp Ile Leu Val
    595                 600                 605 tat aaa ccc cca aat tgc aaa gct ttc cga gat gaa gaa ctg tgc aga    1872
Tyr Lys Pro Pro Asn Cys Lys Ala Phe Arg Asp Glu Glu Leu Cys Arg
610                 615                 620 aac gct ggt cca ggg ata aaa tgt gtt tgg aat aag aat cac tgt gaa    1920
Asn Ala Gly Pro Gly Ile Lys Cys Val Trp Asn Lys Asn His Cys Glu
625                 630                 635                 640 tct tgg gag tct ggg aat aca aat aat att ctc aga gcc aag tgc cct    1968
Ser Trp Glu Ser Gly Asn Thr Asn Asn Ile Leu Arg Ala Lys Cys Pro
            645                 650                 655 ccc aag aca gct gct acc gat gac aga tgt tac aga tat gct gac tgt    2016
Pro Lys Thr Ala Ala Thr Asp Asp Arg Cys Tyr Arg Tyr Ala Asp Cys
        660                 665                 670 gcc agc tgc aca gcc aac acg aac ggg tgc cag tgg tgt gac gac aag    2064
Ala Ser Cys Thr Ala Asn Thr Asn Gly Cys Gln Trp Cys Asp Asp Lys
    675                 680                 685
```

```
aaa tgc atc tca gcc agc agc aac tgc agc acg tct gtc aga aac tac      2112
Lys Cys Ile Ser Ala Ser Ser Asn Cys Ser Thr Ser Val Arg Asn Tyr
        690                 695                 700 act aaa tgt cat ata aga aat gag cag att tgt aac aaa ctt aca agc      2160
Thr Lys Cys His Ile Arg Asn Glu Gln Ile Cys Asn Lys Leu Thr Ser
705                 710                 715                 720 tgt aaa agc tgt tca ctc aac ttg aat tgc cag tgg gat cag cgg cag      2208
Cys Lys Ser Cys Ser Leu Asn Leu Asn Cys Gln Trp Asp Gln Arg Gln
                725                 730                 735 cag gaa tgt cag gct ttg cca gct cac ctt tgt gga gaa ggc tgg aat      2256
Gln Glu Cys Gln Ala Leu Pro Ala His Leu Cys Gly Glu Gly Trp Asn
            740                 745                 750 cat gtt ggg gac gct tgt ctt cga atc aat tcc agt cga gaa agc tat      2304
His Val Gly Asp Ala Cys Leu Arg Ile Asn Ser Ser Arg Glu Ser Tyr
        755                 760                 765 gat aat gcc aaa ctt tat tgc tat aac ctc agt gga aat ctc gcc tcc      2352
Asp Asn Ala Lys Leu Tyr Cys Tyr Asn Leu Ser Gly Asn Leu Ala Ser
770                 775                 780 ctg acc acg tcc aag gag gtg gag ttt gtg ttg gat gaa ata cag aag      2400
Leu Thr Thr Ser Lys Glu Val Glu Phe Val Leu Asp Glu Ile Gln Lys
785                 790                 795                 800 ttc aca cag cag aaa gtg tca ccg tgg gta ggc cta cgc aag atc aac      2448
Phe Thr Gln Gln Lys Val Ser Pro Trp Val Gly Leu Arg Lys Ile Asn
                805                 810                 815 ata tcc tac tgg gga tgg gag gac atg tct cct ttc aca aat aca agc      2496
Ile Ser Tyr Trp Gly Trp Glu Asp Met Ser Pro Phe Thr Asn Thr Ser
            820                 825                 830 ctg cag tgg ctt cct ggt gag cca aat gac tct gga ttc tgt gcc tac      2544
Leu Gln Trp Leu Pro Gly Glu Pro Asn Asp Ser Gly Phe Cys Ala Tyr
        835                 840                 845 tta gaa agg gct gca gtg gca ggg tta aaa gca aac cct tgc aca tcc      2592
Leu Glu Arg Ala Ala Val Ala Gly Leu Lys Ala Asn Pro Cys Thr Ser
850                 855                 860 atg gca gat gga ctc gtt tgt gaa aag cct gta gta agc cca aat cag      2640
Met Ala Asp Gly Leu Val Cys Glu Lys Pro Val Val Ser Pro Asn Gln
865                 870                 875                 880 aac gcg agg ccg tgc aag aag ccg tgc tcc ctg agg acc tcc tgc gcc      2688
Asn Ala Arg Pro Cys Lys Lys Pro Cys Ser Leu Arg Thr Ser Cys Ala
                885                 890                 895 aac tgc acg agc agc ggc atg gag tgc atg tgg tgc agc agc acg aag      2736
Asn Cys Thr Ser Ser Gly Met Glu Cys Met Trp Cys Ser Ser Thr Lys
            900                 905                 910 cgc tgt gtg gac tcc aac gct tac atc atc tcc ttt ccc tac gga cag      2784
Arg Cys Val Asp Ser Asn Ala Tyr Ile Ile Ser Phe Pro Tyr Gly Gln
        915                 920                 925 tgc ctg gag tgg cag act gcc acc tgc tcg cct caa aat tgt tct ggg      2832
Cys Leu Glu Trp Gln Thr Ala Thr Cys Ser Pro Gln Asn Cys Ser Gly
930                 935                 940 tta aga acc tgt gga cag tgc ttg gag cag cca ggg tgt ggc tgg tgc      2880
Leu Arg Thr Cys Gly Gln Cys Leu Glu Gln Pro Gly Cys Gly Trp Cys
945                 950                 955                 960 aac gat cct agt aac aca gga aga ggc tat tgc atc gaa ggg tct tcc      2928
Asn Asp Pro Ser Asn Thr Gly Arg Gly Tyr Cys Ile Glu Gly Ser Ser
                965                 970                 975 cgg ggc cca atg aaa ctc gtg ggg gtc cac aac agt gac gtg gtt ctt      2976
Arg Gly Pro Met Lys Leu Val Gly Val His Asn Ser Asp Val Val Leu
            980                 985                 990 gac acc agc ctc tgc ccc aag gag     aag aac tac gag tgg    tct ttt atc   3024
Asp Thr Ser Leu Cys Pro Lys Glu     Lys Asn Tyr Glu Trp    Ser Phe Ile
```

-continued

```
               995                 1000                 1005
cag tgt cca gct tgc cag tgt aat gga cac agc acg tgc atc aac         3069
Gln Cys Pro Ala Cys Gln Cys Asn Gly His Ser Thr Cys Ile Asn
    1010                1015                1020 aac aac gtc tgt gag cag tgt aag aat ctc acc act ggg cga cag         3114
Asn Asn Val Cys Glu Gln Cys Lys Asn Leu Thr Thr Gly Arg Gln
    1025                1030                1035 tgt cag gaa tgc atg cca ggg tac tat gga gac cca acc aac ggt         3159
Cys Gln Glu Cys Met Pro Gly Tyr Tyr Gly Asp Pro Thr Asn Gly
    1040                1045                1050 ggg cag tgc aca gct tgc acg tgc ggc ggc cat gcg aac gtc tgt         3204
Gly Gln Cys Thr Ala Cys Thr Cys Gly Gly His Ala Asn Val Cys
    1055                1060                1065 cac ctg cac acg gga aag tgt ttt tgc aca acc aag ggg atc aag         3249
His Leu His Thr Gly Lys Cys Phe Cys Thr Thr Lys Gly Ile Lys
    1070                1075                1080 ggt gac cag tgc cag cta tgt gac tct gaa aat cgc tat gtt ggt         3294
Gly Asp Gln Cys Gln Leu Cys Asp Ser Glu Asn Arg Tyr Val Gly
    1085                1090                1095 aat cca ctt agg ggg aca tgc tat tac agt ctt ctg att gac tac         3339
Asn Pro Leu Arg Gly Thr Cys Tyr Tyr Ser Leu Leu Ile Asp Tyr
    1100                1105                1110 cag ttt acc ttc agc ttg ctg cag gaa gat gac cgg cac cac act         3384
Gln Phe Thr Phe Ser Leu Leu Gln Glu Asp Asp Arg His His Thr
    1115                1120                1125 gcc atc aac ttc atc gcc aac cca gag cag tca aac aaa aac ttg         3429
Ala Ile Asn Phe Ile Ala Asn Pro Glu Gln Ser Asn Lys Asn Leu
    1130                1135                1140 gac att tcg att aat gct tcc aac aac ttt aat ctc aac att acg         3474
Asp Ile Ser Ile Asn Ala Ser Asn Asn Phe Asn Leu Asn Ile Thr
    1145                1150                1155 tgg tca gtt ggc tca aca ggt gga acc ata tct ggg gaa gag act         3519
Trp Ser Val Gly Ser Thr Gly Gly Thr Ile Ser Gly Glu Glu Thr
    1160                1165                1170 cct ata gtt tct aag aca aat ata aag gaa tac aga gac agc ttt         3564
Pro Ile Val Ser Lys Thr Asn Ile Lys Glu Tyr Arg Asp Ser Phe
    1175                1180                1185 tcc tat gaa aaa ttt aac ttc aga agc aat cct aat atc aca ttt         3609
Ser Tyr Glu Lys Phe Asn Phe Arg Ser Asn Pro Asn Ile Thr Phe
    1190                1195                1200 tat gtg tat gtc agc aac ttc tcc tgg cct att aaa ata cag att         3654
Tyr Val Tyr Val Ser Asn Phe Ser Trp Pro Ile Lys Ile Gln Ile
    1205                1210                1215 gcg ttt tca caa cac aac acg atc atg gat ctc gtg cag ttc ttt         3699
Ala Phe Ser Gln His Asn Thr Ile Met Asp Leu Val Gln Phe Phe
    1220                1225                1230 gtc acc ttc ttc agt tgt ttt tta tct tta ctg ctg gtg gct gct         3744
Val Thr Phe Phe Ser Cys Phe Leu Ser Leu Leu Leu Val Ala Ala
    1235                1240                1245 gtg gtc tgg aag atc aaa caa act tgc tgg gct tct cgt cgg agg         3789
Val Val Trp Lys Ile Lys Gln Thr Cys Trp Ala Ser Arg Arg Arg
    1250                1255                1260 gag caa ctg ctt cga gaa cga cag cag atg gcc agc cgt ccc ttt         3834
Glu Gln Leu Leu Arg Glu Arg Gln Gln Met Ala Ser Arg Pro Phe
    1265                1270                1275 gct tct gtt gat gta gcc ctg gaa gta gga gct gaa cag aca gac         3879
Ala Ser Val Asp Val Ala Leu Glu Val Gly Ala Glu Gln Thr Asp
    1280                1285                1290 ttt ctg cga ggg cca tta gag ggt gcc cct aag cca ata gcc atc         3924
Phe Leu Arg Gly Pro Leu Glu Gly Ala Pro Lys Pro Ile Ala Ile
```

```
                Phe Leu Arg Gly Pro Leu Glu Gly Ala Pro Lys Pro Ile Ala Ile
                    1295                1300                1305 gaa ccc tgc gct ggg aac aga gct gct gtc ctg act gtg ttt ctc              3969
Glu Pro Cys Ala Gly Asn Arg Ala Ala Val Leu Thr Val Phe Leu
            1310                1315                1320 tgt cta ccg aga gga tct tca ggc gcc cca ccc cct ggg cag tca              4014
Cys Leu Pro Arg Gly Ser Ser Gly Ala Pro Pro Pro Gly Gln Ser
        1325                1330                1335 ggc ctt gct atc gcc agt gcc ctg ata gac atc tca cag cag aag              4059
Gly Leu Ala Ile Ala Ser Ala Leu Ile Asp Ile Ser Gln Gln Lys
    1340                1345                1350 cct tct gat aat aaa gac aag act tct gga gtc cgc aat cgg aag              4104
Pro Ser Asp Asn Lys Asp Lys Thr Ser Gly Val Arg Asn Arg Lys
1355                1360                1365 cac ctc tcc aca cgt caa gga act tgt gtc                                  4134
His Leu Ser Thr Arg Gln Gly Thr Cys Val
    1370                1375

<210> SEQ ID NO 19
<211> LENGTH: 1378
<212> TYPE: PRT
<213> ORGANISM: homo sapiens

<400> SEQUENCE: 19

Met Glu Pro Gly Val Arg Ala Arg Ser Gly Ala Pro Gln Pro Ala Ser
1               5                   10                  15

Pro Val Leu Trp Arg Ala Arg Pro Ala Gly Gly Gly Ala Ser Ser
                20                  25                  30

Trp Leu Leu Leu Asp Gly Asn Ser Trp Leu Leu Cys Tyr Gly Phe Leu
            35                  40                  45

Tyr Leu Ala Leu Tyr Ala Gln Val Ser Gln Ser Lys Pro Cys Glu Arg
        50                  55                  60

Thr Gly Ser Cys Phe Ser Gly Arg Cys Val Asn Ser Thr Cys Leu Cys
65                  70                  75                  80

Asp Pro Gly Trp Val Gly Asp Gln Cys Gln His Cys Gln Gly Arg Phe
                85                  90                  95

Lys Leu Thr Glu Pro Ser Gly Tyr Leu Thr Asp Gly Pro Ile Asn Tyr
                100                 105                 110

Lys Tyr Lys Thr Lys Cys Thr Trp Leu Ile Glu Gly Tyr Pro Asn Ala
            115                 120                 125

Val Leu Arg Leu Arg Phe Asn His Phe Ala Thr Glu Cys Ser Trp Asp
        130                 135                 140

His Met Tyr Val Tyr Asp Gly Asp Ser Ile Tyr Ala Pro Leu Val Ala
145                 150                 155                 160

Val Leu Ser Gly Leu Ile Val Pro Glu Val Arg Gly Asn Glu Thr Val
                165                 170                 175

Pro Glu Val Val Thr Thr Ser Gly Tyr Ala Leu Leu His Phe Phe Ser
            180                 185                 190

Asp Ala Ala Tyr Asn Leu Thr Gly Phe Asn Ile Phe Tyr Ser Ile Asn
        195                 200                 205

Ser Cys Pro Asn Asn Cys Ser Gly His Gly Lys Cys Thr Thr Ser Val
    210                 215                 220

Ser Val Ala Ser Gln Val Tyr Cys Glu Cys Asp Lys Tyr Trp Lys Gly
225                 230                 235                 240

Glu Ala Cys Asp Ile Pro Tyr Cys Lys Ala Asn Cys Gly Ser Pro Asp
                245                 250                 255
```

```
His Gly Tyr Cys Asp Leu Thr Gly Glu Lys Leu Cys Val Cys Asn Asp
            260                 265                 270

Ser Trp Gln Gly Pro Asp Cys Ser Leu Asn Val Pro Ser Thr Glu Ser
        275                 280                 285

Tyr Trp Ile Leu Pro Asn Val Lys Pro Phe Ser Pro Ser Val Gly Arg
    290                 295                 300

Ala Ser His Lys Ala Val Leu His Gly Lys Phe Met Trp Val Ile Gly
305                 310                 315                 320

Gly Tyr Thr Phe Asn Tyr Ser Ser Phe Gln Met Val Leu Asn Tyr Asn
                325                 330                 335

Leu Glu Ser Ser Ile Trp Asn Val Gly Ala Val Ser Arg Gly Pro Leu
            340                 345                 350

Gln Arg Tyr Gly His Ser Leu Ala Leu Tyr Gln Glu Asn Ile Phe Met
        355                 360                 365

Tyr Gly Gly Arg Met Glu Thr Ser Asp Gly Asn Val Thr Asp Glu Leu
    370                 375                 380

Trp Val Phe Asn Val Arg Ser Gln Ser Trp Ser Thr Lys Thr Pro Thr
385                 390                 395                 400

Val Leu Gly His Ser Gln Gln Tyr Ala Val Glu Gly His Ser Ala His
                405                 410                 415

Ile Met Glu Leu Asp Ser Arg Asp Val Val Met Ile Val Ile Phe Gly
            420                 425                 430

Tyr Ser Ala Ile Tyr Gly Tyr Thr Ser Ser Ile Gln Glu Tyr His Ile
        435                 440                 445

Ser Ser Asn Thr Trp Leu Val Pro Glu Thr Lys Gly Ala Ile Val Gln
    450                 455                 460

Gly Gly Tyr Gly His Thr Ser Val Tyr Asp Glu Val Thr Lys Ser Ile
465                 470                 475                 480

Tyr Val His Gly Gly Tyr Lys Ala Leu Pro Gly Asn Lys Tyr Gly Leu
                485                 490                 495

Val Asp Asp Leu Tyr Lys Tyr Glu Val Asn Thr Arg Thr Trp Thr Ile
            500                 505                 510

Leu Lys Glu Ser Gly Phe Ala Arg Tyr Leu His Ser Ala Val Leu Ile
        515                 520                 525

Asn Gly Ala Met Leu Ile Phe Gly Gly Asn Thr His Asn Asp Thr Ser
    530                 535                 540

Leu Ser Asn Gly Ala Lys Cys Phe Ser Ala Asp Phe Leu Ala Tyr Asp
545                 550                 555                 560

Ile Ala Cys Asp Glu Trp Lys Thr Leu Pro Lys Pro Asn Leu His Arg
                565                 570                 575

Asp Val Asn Arg Phe Gly His Ser Ala Val Val Ile Asn Gly Ser Met
            580                 585                 590

Tyr Ile Phe Gly Gly Phe Ser Ser Val Leu Leu Asn Asp Ile Leu Val
        595                 600                 605

Tyr Lys Pro Pro Asn Cys Lys Ala Phe Arg Asp Glu Leu Cys Arg
    610                 615                 620

Asn Ala Gly Pro Gly Ile Lys Cys Val Trp Asn Lys Asn His Cys Glu
625                 630                 635                 640

Ser Trp Glu Ser Gly Asn Thr Asn Asn Ile Leu Arg Ala Lys Cys Pro
                645                 650                 655

Pro Lys Thr Ala Ala Thr Asp Asp Arg Cys Tyr Arg Tyr Ala Asp Cys
            660                 665                 670

Ala Ser Cys Thr Ala Asn Thr Asn Gly Cys Gln Trp Cys Asp Asp Lys
```

-continued

```
            675                 680                 685
Lys Cys Ile Ser Ala Ser Ser Asn Cys Ser Thr Ser Val Arg Asn Tyr
690                 695                 700

Thr Lys Cys His Ile Arg Asn Glu Gln Ile Cys Asn Lys Leu Thr Ser
705                 710                 715                 720

Cys Lys Ser Cys Ser Leu Asn Leu Asn Cys Gln Trp Asp Gln Arg Gln
                725                 730                 735

Gln Glu Cys Gln Ala Leu Pro Ala His Leu Cys Gly Glu Gly Trp Asn
                740                 745                 750

His Val Gly Asp Ala Cys Leu Arg Ile Asn Ser Ser Arg Glu Ser Tyr
                755                 760                 765

Asp Asn Ala Lys Leu Tyr Cys Tyr Asn Leu Ser Gly Asn Leu Ala Ser
770                 775                 780

Leu Thr Thr Ser Lys Glu Val Glu Phe Val Leu Asp Glu Ile Gln Lys
785                 790                 795                 800

Phe Thr Gln Gln Lys Val Ser Pro Trp Val Gly Leu Arg Lys Ile Asn
                805                 810                 815

Ile Ser Tyr Trp Gly Trp Glu Asp Met Ser Pro Phe Thr Asn Thr Ser
                820                 825                 830

Leu Gln Trp Leu Pro Gly Glu Pro Asn Asp Ser Gly Phe Cys Ala Tyr
                835                 840                 845

Leu Glu Arg Ala Ala Val Ala Gly Leu Lys Ala Asn Pro Cys Thr Ser
850                 855                 860

Met Ala Asp Gly Leu Val Cys Glu Lys Pro Val Val Ser Pro Asn Gln
865                 870                 875                 880

Asn Ala Arg Pro Cys Lys Lys Pro Cys Ser Leu Arg Thr Ser Cys Ala
                885                 890                 895

Asn Cys Thr Ser Ser Gly Met Glu Cys Met Trp Cys Ser Ser Thr Lys
                900                 905                 910

Arg Cys Val Asp Ser Asn Ala Tyr Ile Ile Ser Phe Pro Tyr Gly Gln
                915                 920                 925

Cys Leu Glu Trp Gln Thr Ala Thr Cys Ser Pro Gln Asn Cys Ser Gly
930                 935                 940

Leu Arg Thr Cys Gly Gln Cys Leu Glu Gln Pro Gly Cys Gly Trp Cys
945                 950                 955                 960

Asn Asp Pro Ser Asn Thr Gly Arg Gly Tyr Cys Ile Glu Gly Ser Ser
                965                 970                 975

Arg Gly Pro Met Lys Leu Val Gly Val His Asn Ser Asp Val Val Leu
                980                 985                 990

Asp Thr Ser Leu Cys Pro Lys Glu Lys Asn Tyr Glu Trp Ser Phe Ile
                995                 1000                1005

Gln Cys Pro Ala Cys Gln Cys Asn Gly His Ser Thr Cys Ile Asn
        1010                1015                1020

Asn Asn Val Cys Glu Gln Cys Lys Asn Leu Thr Thr Gly Arg Gln
        1025                1030                1035

Cys Gln Glu Cys Met Pro Gly Tyr Tyr Gly Asp Pro Thr Asn Gly
        1040                1045                1050

Gly Gln Cys Thr Ala Cys Thr Cys Gly Gly His Ala Asn Val Cys
        1055                1060                1065

His Leu His Thr Gly Lys Cys Phe Cys Thr Thr Lys Gly Ile Lys
        1070                1075                1080

Gly Asp Gln Cys Gln Leu Cys Asp Ser Glu Asn Arg Tyr Val Gly
        1085                1090                1095
```

-continued

```
Asn Pro Leu Arg Gly Thr Cys Tyr Tyr Ser Leu Leu Ile Asp Tyr
    1100                1105                1110

Gln Phe Thr Phe Ser Leu Leu Gln Glu Asp Arg His His Thr
    1115                1120                1125

Ala Ile Asn Phe Ile Ala Asn Pro Glu Gln Ser Asn Lys Asn Leu
    1130                1135                1140

Asp Ile Ser Ile Asn Ala Ser Asn Asn Phe Asn Leu Asn Ile Thr
    1145                1150                1155

Trp Ser Val Gly Ser Thr Gly Gly Thr Ile Ser Gly Glu Glu Thr
    1160                1165                1170

Pro Ile Val Ser Lys Thr Asn Ile Lys Glu Tyr Arg Asp Ser Phe
    1175                1180                1185

Ser Tyr Glu Lys Phe Asn Phe Arg Ser Asn Pro Asn Ile Thr Phe
    1190                1195                1200

Tyr Val Tyr Val Ser Asn Phe Ser Trp Pro Ile Lys Ile Gln Ile
    1205                1210                1215

Ala Phe Ser Gln His Asn Thr Ile Met Asp Leu Val Gln Phe Phe
    1220                1225                1230

Val Thr Phe Phe Ser Cys Phe Leu Ser Leu Leu Leu Val Ala Ala
    1235                1240                1245

Val Val Trp Lys Ile Lys Gln Thr Cys Trp Ala Ser Arg Arg Arg
    1250                1255                1260

Glu Gln Leu Leu Arg Glu Arg Gln Gln Met Ala Ser Arg Pro Phe
    1265                1270                1275

Ala Ser Val Asp Val Ala Leu Glu Val Gly Ala Glu Gln Thr Asp
    1280                1285                1290

Phe Leu Arg Gly Pro Leu Glu Gly Ala Pro Lys Pro Ile Ala Ile
    1295                1300                1305

Glu Pro Cys Ala Gly Asn Arg Ala Ala Val Leu Thr Val Phe Leu
    1310                1315                1320

Cys Leu Pro Arg Gly Ser Ser Gly Ala Pro Pro Gly Gln Ser
    1325                1330                1335

Gly Leu Ala Ile Ala Ser Ala Leu Ile Asp Ile Ser Gln Gln Lys
    1340                1345                1350

Pro Ser Asp Asn Lys Asp Lys Thr Ser Gly Val Arg Asn Arg Lys
    1355                1360                1365

His Leu Ser Thr Arg Gln Gly Thr Cys Val
    1370                1375

<210> SEQ ID NO 20
<211> LENGTH: 18
<212> TYPE: DNA
<213> ORGANISM: Artificial Sequence
<220> FEATURE:
<223> OTHER INFORMATION: PCR Primer; sense strand

<400> SEQUENCE: 20
ggggaagatg gagactgg                                                 18

<210> SEQ ID NO 21
<211> LENGTH: 34
<212> TYPE: DNA
<213> ORGANISM: Artificial Sequence
<220> FEATURE:
<223> OTHER INFORMATION: PCR Primer; Antisense strand

<400> SEQUENCE: 21
```
gtacagctat taaaggtgca tatattgaat ctcc                            34

<210> SEQ ID NO 22
<211> LENGTH: 33
<212> TYPE: DNA
<213> ORGANISM: Artificial Sequence
<220> FEATURE:
<223> OTHER INFORMATION: PCR Primer; sense strand

<400> SEQUENCE: 22
ttaacagaac cttctggata tttaacagat ggc                             33

<210> SEQ ID NO 23
<211> LENGTH: 28
<212> TYPE: DNA
<213> ORGANISM: Artificial Sequence
<220> FEATURE:
<223> OTHER INFORMATION: PCR Primer; Antisense strand

<400> SEQUENCE: 23
ctgaatgtcc ctccacagca tactgctg                                   28

<210> SEQ ID NO 24
<211> LENGTH: 30
<212> TYPE: DNA
<213> ORGANISM: Artificial Sequence
<220> FEATURE:
<223> OTHER INFORMATION: PCR Primer; sense strand

<400> SEQUENCE: 24
gttcttggac atggtcagca gtatgctgtg                                 30

<210> SEQ ID NO 25
<211> LENGTH: 30
<212> TYPE: DNA
<213> ORGANISM: Artificial Sequence
<220> FEATURE:
<223> OTHER INFORMATION: PCR Primer; Antisense strand

<400> SEQUENCE: 25
ttgtattggc agtacagctg gcacaatctg                                 30

<210> SEQ ID NO 26
<211> LENGTH: 32
<212> TYPE: DNA
<213> ORGANISM: Artificial Sequence
<220> FEATURE:
<223> OTHER INFORMATION: PCR Primer; sense strand

<400> SEQUENCE: 26
gctgcttctg atgacagatg ttacagatat gc                              32

<210> SEQ ID NO 27
<211> LENGTH: 30
<212> TYPE: DNA
<213> ORGANISM: Artificial Sequence
<220> FEATURE:
<223> OTHER INFORMATION: PCR Primer; Antisense strand

<400> SEQUENCE: 27
cacatccagg ctgttccaaa cactgtccac                                 30

<210> SEQ ID NO 28
<211> LENGTH: 32
<212> TYPE: DNA

<213> ORGANISM: Artificial Sequence
<220> FEATURE:
<223> OTHER INFORMATION: PCR Primer; sense strand

<400> SEQUENCE: 28
ccatatggac aatgtctaga gtggcaaact gc                                    32

<210> SEQ ID NO 29
<211> LENGTH: 35
<212> TYPE: DNA
<213> ORGANISM: Artificial Sequence
<220> FEATURE:
<223> OTHER INFORMATION: PCR Primer; Antisense strand

<400> SEQUENCE: 29
gctgacgtac acatagaacg taatgttagg attgc                                 35

<210> SEQ ID NO 30
<211> LENGTH: 35
<212> TYPE: DNA
<213> ORGANISM: Artificial Sequence
<220> FEATURE:
<223> OTHER INFORMATION: PCR Primer; sense strand

<400> SEQUENCE: 30
caatatctgg ggaagagact tctatagttt ccaag                                 35

<210> SEQ ID NO 31
<211> LENGTH: 36
<212> TYPE: DNA
<213> ORGANISM: Artificial Sequence
<220> FEATURE:
<223> OTHER INFORMATION: PCR Primer; Antisense strand

<400> SEQUENCE: 31
ggtttccatt tctcagacac aagttccttg acgtgt                                36

<210> SEQ ID NO 32
<211> LENGTH: 35
<212> TYPE: DNA
<213> ORGANISM: Artificial Sequence
<220> FEATURE:
<223> OTHER INFORMATION: PCR Primer; sense strand

<400> SEQUENCE: 32
caatatctgg ggaagagact tctatagttt ccaag                                 35

<210> SEQ ID NO 33
<211> LENGTH: 36
<212> TYPE: DNA
<213> ORGANISM: Artificial Sequence
<220> FEATURE:
<223> OTHER INFORMATION: PCR Primer; Antisense strand

<400> SEQUENCE: 33
ggtttccatt tctcagacac aagttccttg acgtgt                                36